(12) United States Patent
Connors et al.

(10) Patent No.: US 7,540,876 B2
(45) Date of Patent: Jun. 2, 2009

(54) PRESSURE ATTENUATION DEVICE

(75) Inventors: Kevin Gerald Connors, Wellesley, MA (US); John Randall Liddicoat, Brooklyn Park, MN (US)

(73) Assignee: AttenueX Technologies, Inc., Newton, MA (US)

( * ) Notice: Subject to any disclaimer, the term of this patent is extended or adjusted under 35 U.S.C. 154(b) by 157 days.

(21) Appl. No.: 11/527,333

(22) Filed: Sep. 26, 2006

(65) Prior Publication Data
US 2007/0156167 A1    Jul. 5, 2007

Related U.S. Application Data

(63) Continuation-in-part of application No. 11/314,601, filed on Dec. 20, 2005, now Pat. No. 7,374,532, which is a continuation of application No. 10/618,571, filed on Jul. 11, 2003, now Pat. No. 6,976,951, which is a continuation of application No. 10/391,446, filed on Mar. 17, 2003, now Pat. No. 6,976,950, and a continuation-in-part of application No. 09/723,309, filed on Nov. 27, 2000, now Pat. No. 6,682,473.

(60) Provisional application No. 60/721,834, filed on Sep. 26, 2005, provisional application No. 60/415,949, filed on Oct. 3, 2002, provisional application No. 60/197,095, filed on Apr. 14, 2000.

(51) Int. Cl.
*A61M 29/00* (2006.01)

(52) U.S. Cl. ..................................... 606/194; 128/897

(58) Field of Classification Search ............. 600/16–18, 600/480, 485–488, 508; 604/891.1; 606/194; 128/897–899
See application file for complete search history.

(56) References Cited

U.S. PATENT DOCUMENTS 2,849,011 A    8/1958    Oddo (Continued)

FOREIGN PATENT DOCUMENTS

FR    2774579    8/1999

(Continued)

OTHER PUBLICATIONS

A New Technique for Dynamic Analysis of Bladder Compliance, Robert F. Gilmore et al., *The Journal of Urology*, vol. 150, pp. 1200-1203, Oct. 1993.

(Continued)

*Primary Examiner*—John P Lacyk
(74) *Attorney, Agent, or Firm*—Knobbe, Martens, Olson & Bear, LLP

(57) ABSTRACT

An implantable blood pressure regulator is provided. The blood pressure regulator includes at least one connection zone and an attenuation zone. The connection zone is suitable for connection to a body conduit, such as a blood vessel. The attenuation zone is movable from a first state to a second state in response to a physiological pressure spikes. The movement from the first state to the second state lowers a level of pressure or dampens a pressure spike in the body conduit.

24 Claims, 66 Drawing Sheets

U.S. PATENT DOCUMENTS

| | | | |
|---|---|---|---|
| 3,841,304 A | 10/1974 | Jones | |
| 4,044,401 A | 8/1977 | Guiset | |
| 4,246,893 A | 1/1981 | Berson | |
| 4,311,146 A | 1/1982 | Wonder | |
| 4,341,218 A | 7/1982 | Ü | |
| 4,346,712 A | 8/1982 | Handa et al. | |
| 4,364,392 A | 12/1982 | Strother et al. | |
| 4,416,267 A | 11/1983 | Garren et al. | |
| 4,441,495 A | 4/1984 | Hicswa | |
| 4,517,979 A | 5/1985 | Pecenka | |
| 4,545,367 A | 10/1985 | Tucci | |
| 4,607,618 A | 8/1986 | Angelchik | |
| 4,694,827 A | 9/1987 | Weiner et al. | |
| 4,723,547 A | 2/1988 | Kullas et al. | |
| 4,773,393 A | 9/1988 | Haber et al. | |
| 4,802,479 A | 2/1989 | Haber et al. | |
| 4,819,637 A | 4/1989 | Dormandy, Jr. et al. | |
| 4,832,680 A | 5/1989 | Haber et al. | |
| 4,850,963 A | 7/1989 | Sparks et al. | |
| 4,899,747 A | 2/1990 | Garren et al. | |
| 4,925,446 A | 5/1990 | Garay et al. | |
| 4,929,214 A | 5/1990 | Liebeman | |
| 4,930,535 A | 6/1990 | Rinehold | |
| 5,084,061 A | 1/1992 | Gau et al. | |
| 5,144,708 A | 9/1992 | Pekar | |
| 5,181,921 A | 1/1993 | Makita et al. | |
| 5,222,970 A | 6/1993 | Reeves | |
| 5,248,275 A | 9/1993 | McGrath et al. | |
| 5,304,123 A | 4/1994 | Atala et al. | |
| 5,308,327 A | 5/1994 | Heaven et al. | |
| 5,411,475 A | 5/1995 | Atala et al. | |
| 5,433,216 A | 7/1995 | Sugrue et al. | |
| 5,437,603 A | 8/1995 | Cerny et al. | |
| 5,479,945 A | 1/1996 | Simon | |
| 5,501,669 A | 3/1996 | Conway et al. | |
| 5,564,143 A | 10/1996 | Pekar et al. | |
| 5,588,556 A | 12/1996 | Sancoff et al. | |
| 5,603,685 A | 2/1997 | Tutrone, Jr. | |
| 5,617,876 A | 4/1997 | van Duyl | |
| 5,779,672 A | 7/1998 | Dormandy, Jr. | |
| 5,830,228 A | 11/1998 | Knapp et al. | |
| 5,830,780 A | 11/1998 | Dennison et al. | |
| 5,868,141 A | 2/1999 | Ellias | |
| 5,964,806 A | 10/1999 | Cook et al. | |
| 5,992,419 A | 11/1999 | Sterzer et al. | |
| 5,992,700 A | 11/1999 | McGothlin | |
| 6,021,781 A | 2/2000 | Thompson et al. | |
| 6,027,442 A | 2/2000 | Von Iderstein | |
| 6,045,498 A | 4/2000 | Burton et al. | |
| 6,102,848 A | 8/2000 | Porter | |
| 6,119,697 A | 9/2000 | Engel et al. | |
| 6,127,010 A | 10/2000 | Rudy | |
| 6,293,923 B1 | 9/2001 | Yachia et al. | |
| 6,398,718 B1 | 6/2002 | Yachia et al. | |
| 6,682,473 B1 | 1/2004 | Matsuura et al. | |
| 6,746,421 B2 | 6/2004 | Yachia et al. | |
| 6,976,950 B2 | 12/2005 | Connors et al. | |
| 6,976,951 B2 | 12/2005 | Connors et al. | |
| 6,988,983 B2 | 1/2006 | Connors et al. | |
| 7,074,178 B2 | 7/2006 | Connors et al. | |
| 7,374,532 B2 | 5/2008 | Conners et al. | |
| 7,470,228 B2 | 12/2008 | Connors et al. | |
| 2002/0082551 A1 | 6/2002 | Yachia et al. | |
| 2002/0165427 A1 | 11/2002 | Yachia et al. | |
| 2004/0111006 A1 | 6/2004 | Alferness et al. | |
| 2005/0187427 A1 | 8/2005 | Connors et al. | |
| 2006/0100478 A1 | 5/2006 | Connors et al. | |

FOREIGN PATENT DOCUMENTS

| | | |
|---|---|---|
| GB | 2023405 | 1/1980 |
| WO | WO 90/13321 | 11/1990 |
| WO | WO 99/24106 | 5/1999 |
| WO | WO 00/54701 | 9/2000 |
| WO | WO 00/54702 | 9/2000 |
| WO | WO 01/78576 | 10/2001 |

OTHER PUBLICATIONS

The Effect of Urinary Bladder Shape on its Mechanics During Filling, Margot S. Damasar et al., *Pergamon*, vol. 6, pp. 725-732, 1995.

Difference in Bladder Compliance with Time and Associations of Bladder Management with Compliance in Spinal Cord Injured Patients, Kyle J. Weld et al., *The Journal of Urology*, vol. 163, pp. 1228-1233, Apr. 2000.

Visco-elastic Properties of Isolated Detrusor Smooth Muscle, A. Wagg et al., *Scandinavian Journel of Urology Nephoral*, Suppl. 201, pp. 12-18, 1999.

Urge Incontinence and the Unstable Bladder, *Practical Urogynecology*, Chapter 8—Incontinence and the Unstable Bladder, pp. 191-214, Oct. 1, 1993.

Decreased Elastin Gene Expression In Noncompliant Human Bladder Tissue: A Competitive Reverse Transcriptase-Polymerase Chain Reaction Analysis, Bob Djavan et al., *Journal of Urology*, vol. 160, pp. 1658-1662, Nov. 1998.

Molecular, Cellular and Experimental Morphology, Narinder Dass et al., *Journal of Anatomy*, vol. 195, Part 3, pp. 447-453, Oct. 1999.

Design of Miniaturized Ultrasonic Bladder Volume Monitor and Subsequent Preliminary Evaluation on 41 Enuretic Patients, *IEEE Transactions on Rehabilitation Engineering*, vol. 6, No. 1, pp. 66-74, Mar. 1998.

Temporal Expression of Elastic Fiber Components in Bladder Development, H.P. Koo et al., *Connective Tissue Research*, vol. 3701-20, pp. 1-11, 1998.

Voiding Dysfunction in Ileal Neobladder, Naohito Mikuma et al., *The Journal of Urology*, vol. 158 pp. 1365-1367, Oct. 1997.

Interstital Cystitus: Bladder Training with Intravesical Oxybutynin, George A. Barballas et al., *The Journal of Urology*, vol. 163, pp. 1818-1822, Jun. 2000.

Noninvasuve Evaluation of Bladder Compliance in Children Using Ultrasound Estimated Bladder Weight, Osamu Ukimura et al., *The Journal of Urology*, vol. 160 pp. 1459-1462, Oct. 1998.

Surgical Complications of Bladder Augmentation: Comparison Between Various Enterocystoplasties in 133 Patients, Bijan Shekarriz et al., *Elsevier Science Inc.*, Pediatric Urology 55, pp. 123-128, 2000.

Elastic Fibers and Their Role in Bladder Extracellular Matrix, Joel Rosenbloom et al., *Muscle Matrix and Bladder Function*, vol. 385, pp. 161-184, 1995.

Effect of Spinal Versus General Anesthesia on Bladder Compliance and Intraabdominal Pressure During Transurethral Procedures, David Olsfanger et al., *Journal of Clinical Anesthesia*, vol. 11, pp. 328-331, 1999.

Structure of the Lymphatic Microcirculation in the Human Urinary Bladder with Different Intraluminal Pressure and Distension, R. Scelsi et al., *Lymphologyu*, pp. 60-66, 1996.

Abstract, Surgical treatment for stress urinary incontinence associated with valsalva induced detrusor instability., S.R. Serets et al. *Website PubMed*, Mar. 2000.

Abstract, Identifying patients who require urodynamic testing before surgery for stress incontinence based on questionnaire information and surgical history., G.E. Lemack et al., *Website PubMed*, Apr. 2000.

Abstract, Ambulatory urodynamics: do they help clinical management?, E. Gorton et al., *Website PubMed*, Mar. 2000.

Abstract, The effect of bladder filling on changes in ultrasonography parameters of the lower urinary tract in women with urinary stress incontinence., A. Martan et al., *Website PubMed*, Jan. 2000.

Abstract, Urodynamic protocol and central review of data for clinical trails in lower urinary tract dysfunction., P. Lewis et al., *Website PubMed*, Mar. 2000.

Abstract, New data on the diagnosis and treatment of urinary stress incontinence in women., J. Colin et al., *Website PubMed*, Feb. 2000.

Abstract, Office evaluation of the patient with an overactive urinary bladder., J. Kowalcyzk, *Website PubMed*, Mar. 2000.

Abstract, Surgical and medical treatment options for urge incontinence., J.M. Lonsway, *Website PubMed*, Mar. 2000.

Abstract, Experimental development of a fixed volume, gravity draining, prosthetic urinary bladder., M.J. Gleeson et al., *Website PubMed*, Jul. 1990.

Abstract, Urodynamics of normal and disordered miction., U. Jonas, *Website PubMed*, Oct. 1979.

Abstract, Whole bladder mechanics during filling., M.S. Damaser, *Website PubMed*, Oct. 1999.

Abstract, A mathematical micturition model to restore simple flow recordings in healthy and symptomatic individuals and enhance uroflow interpretation., F.A. Valentini et al., *Website PubMed*, 2000.

Abstract, Barometers and bladders: a primer on pressures., D.A. Bloom et al., *Website PubMed*, Mar. 2000.

Die Detrusormyektomie (Autoaugmentation) in der Behandlung der Hyperreflexiven Low-compliance-Blasé, M. Stohrer et al., *Der Urologe [A]*, pp. 30-37, 1999.

Effect of aging on bladder function and the response to outlet obstruction in female rats, A.D. Kohan et al., *Urol Res*. 2000, 28: pp. 33-37.

Fluid Transients in Systems by Wylie et al., Prentice Hall (1993) pp. 59-70.

2005/0187427 (U.S. Appl. No. 10/391,448) and it prosecution history including the Office Actions mailed Jan. 10, 2007 and Aug. 23, 2007, and the Amendment filed Jun. 11, 2007.

2006/0100478 (U.S. Appl. No. 11/314,601) and its prosecution history including the Office Action mailed Jun. 5, 2006 and the Amendment filed Oct. 5, 2006.

PCT Search Report and Written Opinion dated Aug. 16, 2007 in 6 pages.

Supplementary European Search Report for European Application No. 03770516.7 dated Aug. 6, 2007 in 3 pages.

Extended European Search Report for European Application No. 07015011.5 dated Sep. 4, 2007 in 6 pages.

Boston Scientific Target Detachable Silicone Balloon, Product Information (Part No. ES-05827 Rev. A); published by Boston Scientific and Target Therapeutics at Fremont, CA or Natick,MA; relevant pages consist of the entire document (total of 24 pages); print-out in 2 pages from the USPTO's Trademark Electronic Search System identifying the date of first used in commerce of on or about Aug. 1998.

European Search Report for European Patent Application No. EP 01 92 7115 dated Nov. 2, 2004 in 3 pages.

| Population Group | Prevalence 2002 | Mortality 2002 | Hospital Discharges 2002 | Cost 2005 |
|---|---|---|---|---|
| Total population | 65,000,000 (32.3%) | 49,707 | 535,000 | $59.7 billion |
| Total males | 29,400,000 (31.5%) | 20,512 (41.3%) | 224,000 | – |
| Total females | 35,600,000 (32.8%) | 29,195 (58.7%) | 312,000 | – |
| White males | 30.6% | 14,713 | – | – |
| White females | 31.0% | 22,329 | – | – |
| Black males | 41.8% | 5,268 | – | – |
| Black females | 45.4% | 6,311 | – | – |
| Mexican-American males | 27.8% | – | – | – |
| Mexican-American females | 28.7% | – | – | – |
| Hispanic or Latino** | 18.2% | – | – | – |
| Asian** | 16.7% | – | – | – |
| American Indians or Alaska Natives** | 21.2% | – | – | – |

Note: (–) = data not available.

\* These percentages represent the portion of total mortality that is males vs. females Sources: Prevalence: NHANES (1999-2002), Hypertension, 2004;44:398-404) and NHLBI: data are age adjusted for age 20 and older. Rates are for non-Hispanics** NHIS (2002). CDC/NCHS; data are for Americans age 18 and older. Mortality: CDC/NCHS; data for white and black males and females include Hispanics Hospital discharges: CDC/NCHS; data include people both living and dead. Cost: NHLBI; data include direct and indirect costs for 2005.

*FIG. 1A*

Hypertension

Cardiac Output

- Hypervolemia
  - renal artery stenosis
  - renal disease
  - hyperaldosteronism
  - hypersection of ADH
  - aortic coarctation
  - pregnancy (preeclamosia)
- Stress
- Pheochromocytoma
  - increased catecholamines

Systematic Vascular Resistance

- Idiopathic
  - primary or essential hypertension
- Stress
  - sympathetic activation
- Atherasclerosis
- Renal artery disease
  - increased catectiolamines
- Thyroid dysfunction
- Diabetes
- Cerebral ischemia (Cushing)

*FIG. 1C*

Abbreviations:
LV Press, left ventricular pressure
a, a-wave; c, c-wave; v-wave
ECG, electrocardiogram
LVEDV, left ventricular end-diastolic volume
LVESV, left ventricular end-systolic volume

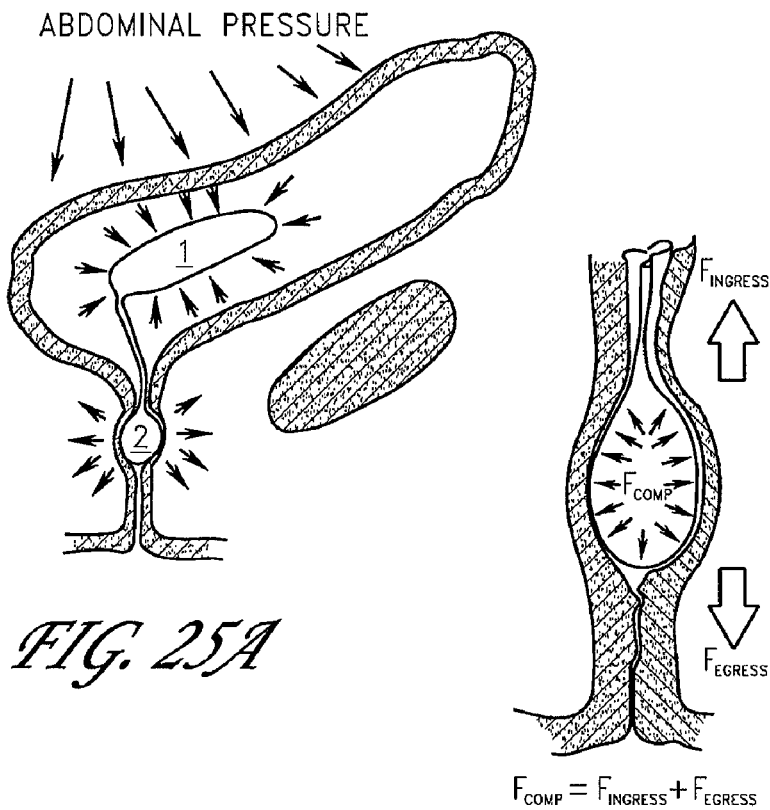
*FIG. 25A*
$F_{COMP} = F_{INGRESS} + F_{EGRESS}$
*FIG. 25B*
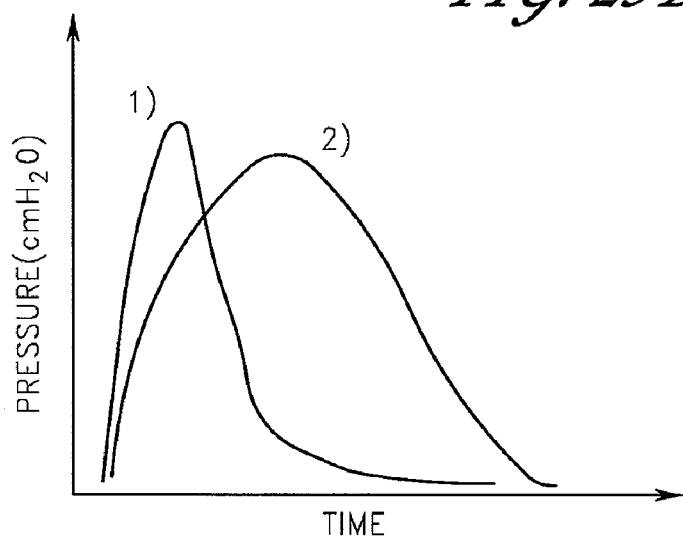
1) INTRA-VESSICAL PRESSURE: RAPID RISE TIME, RAPID DECAY...
2) SECONDARY BALLOON PRESSURE: RAPID RISE TIME, DELAYED DECAY TIME...
*FIG. 25C*

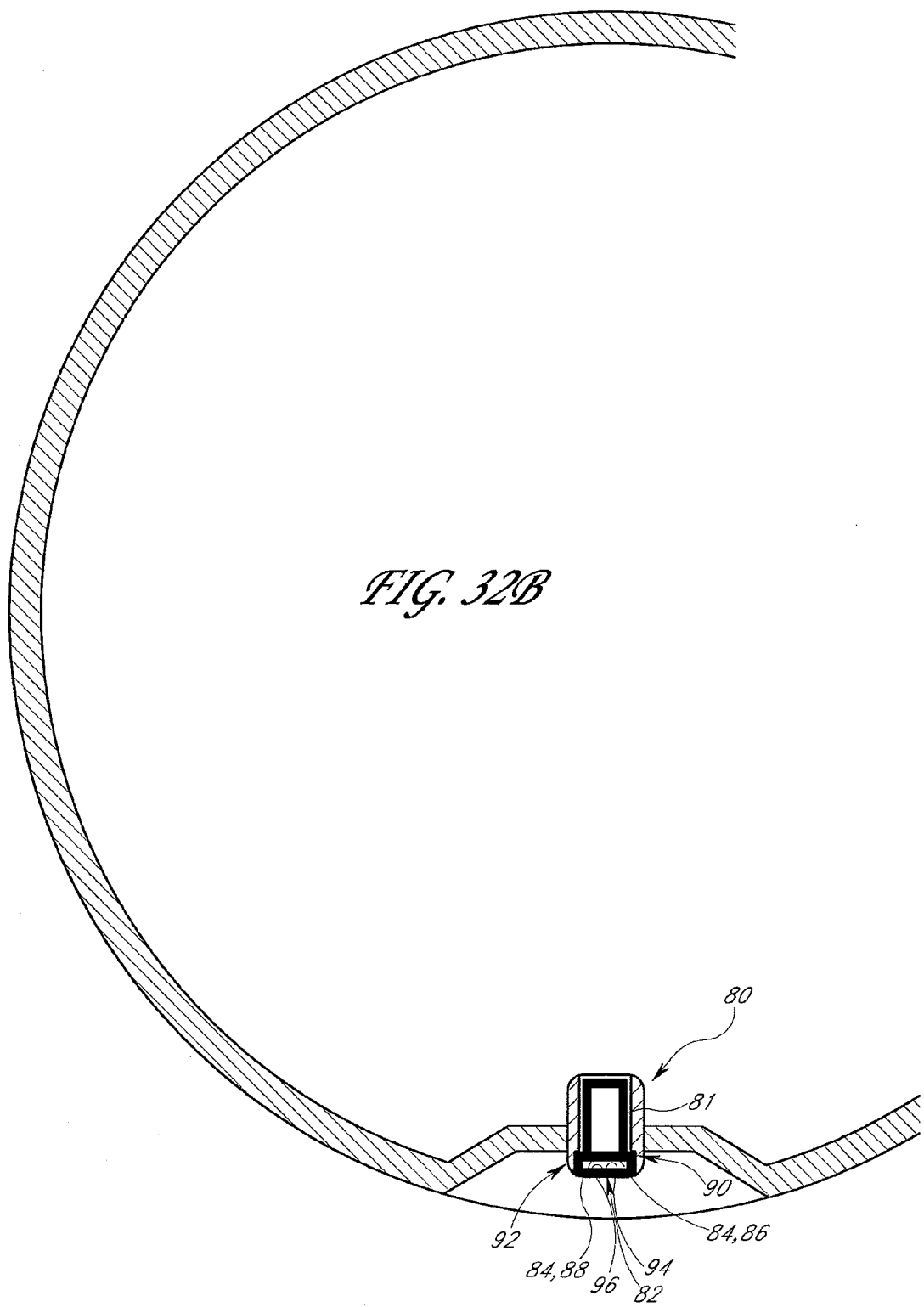

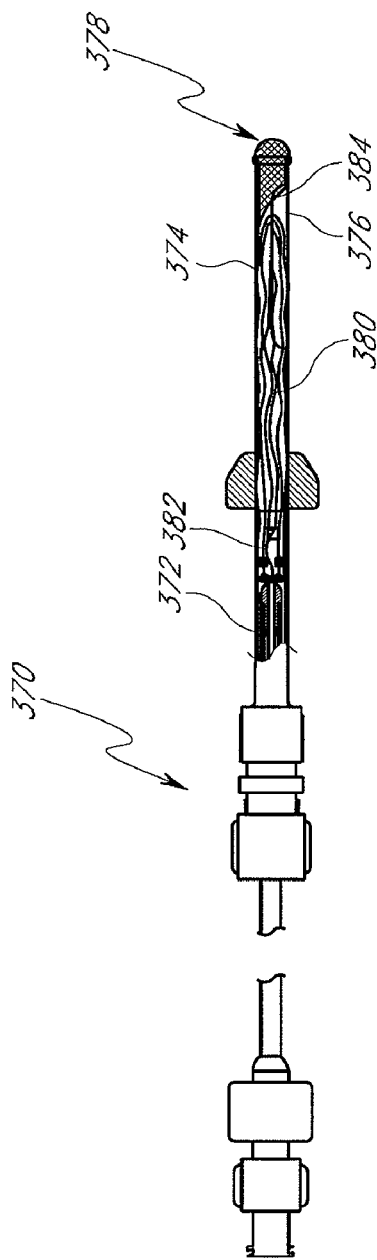
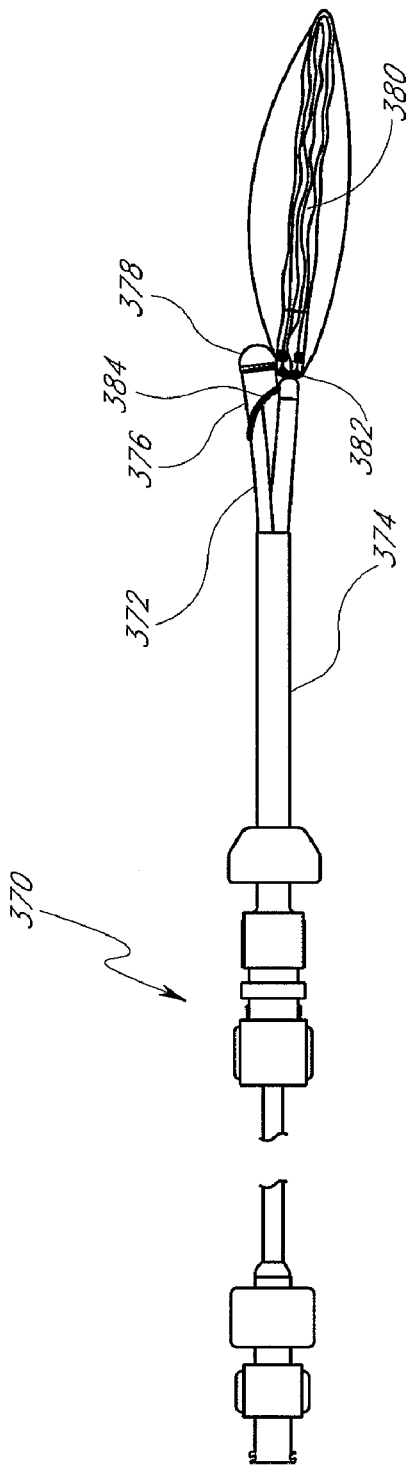

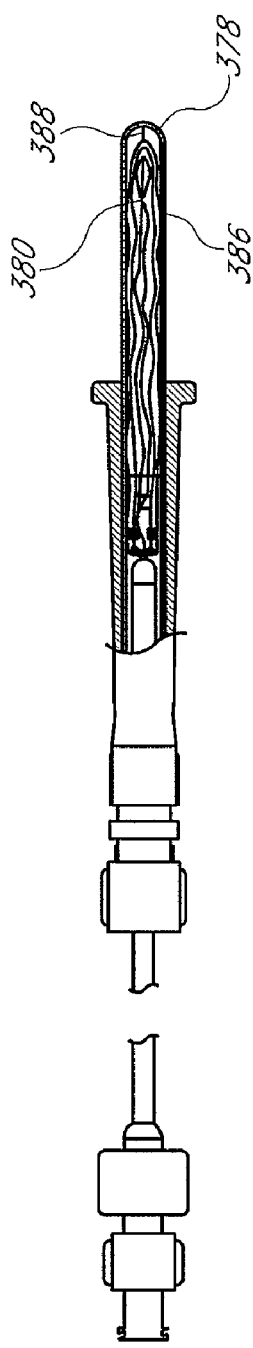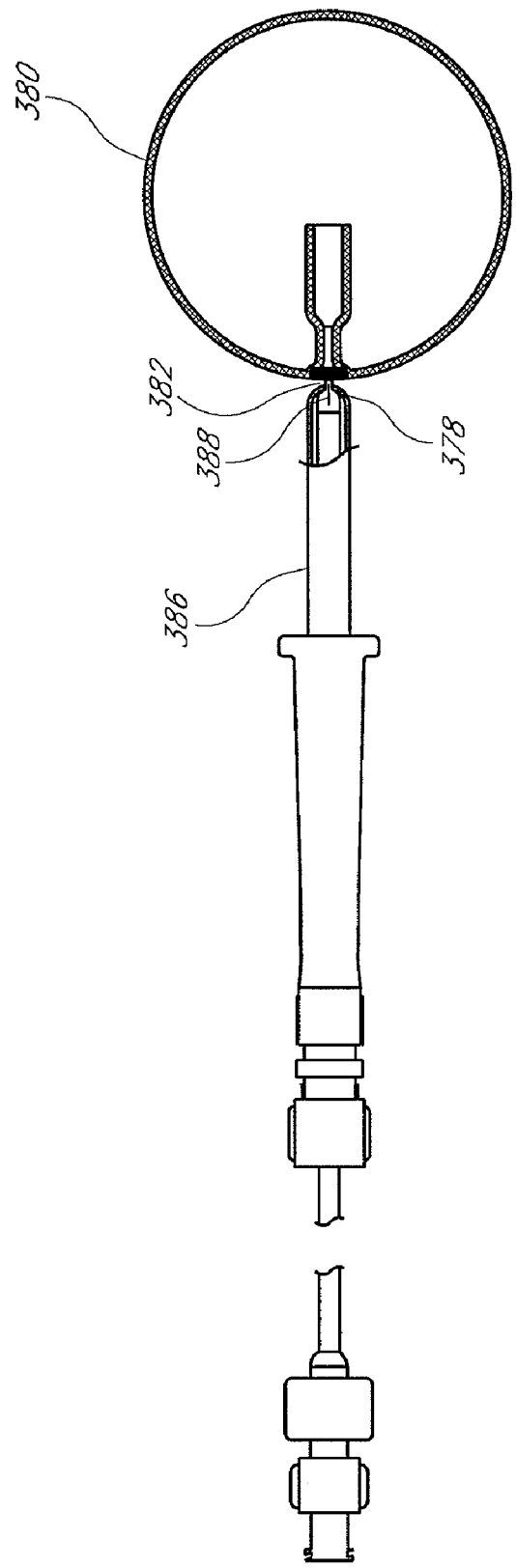
FIG. 35A
FIG. 35B

PRESSURE ATTENUATION DEVICE

CROSS-REFERENCE TO RELATED APPLICATIONS

This application claims priority to U.S. Provisional Patent Application Ser. No. 60/721,834, filed Sep. 26, 2005 and is a continuation-in-part of U.S. patent application Ser. No. 11/314,601, filed Dec. 20, 2005, now U.S. Pat. No. 7,374,532 which is a continuation of U.S. patent application Ser. No. 10/618,571, filed Jul. 11, 2003, now U.S. Pat. No. 6,976,951, which is a continuation of U.S. patent application Ser. No. 10/391,446, filed Mar. 17, 2003, now U.S. Pat. No. 6,976,950, which claims priority to U.S. Provisional Patent Application Ser. No. 60/415,949, filed Oct. 3, 2002. U.S. Pat. No. 6,976,950 also is a continuation-in-part of U.S. patent application Ser. No. 09/723,309, filed on Nov. 27, 2000, now U.S. Pat. No. 6,682,473, which claims priority to U.S. Provisional Patent Application Ser. No. 60/197,095, filed Apr. 14, 2000. The disclosures of the aforementioned applications are hereby incorporated in their entirety herein by reference.

BACKGROUND OF THE INVENTION

1. Field of the Invention

The application relates generally to methods and apparatus for attenuating and/or baffling transient pressure waves in relatively incompressible materials in organs and systems of the human body, including, but not limited to the following systems: cardiovascular, pulmonary, renal/urological, gastrointestinal, hepatic/biliary, gynecological, central nervous, musculoskeletal, otorhinolaryngical and ophthalmic.

The present application also relates generally to the fields of end-stage heart failure and noncompliant vasculature, and in particular to the treatment of disorders caused by fluctuations of intravascular pressure. In one aspect, methods and devices are provided for the treatment of hypertension and its adverse sequelae.

2. Description of the Related Art

Pressure waves are known to propagate through incompressible fluids in various organs of the body. Such pressure waves can be cyclical and part of normal body function, such as in the cardiovascular system, or more random, such as arise in response to environmental stimuli.

In the cardiovascular system, the beating of the heart cyclically pumps blood through the vasculature. This process normally generates pressure waves in the vascular system. Hypertension (high blood pressure), a malady from which many adults suffer, is associated with cardiovascular disease and stroke. Though there are many causes of hypertension, primary (or essential) hypertension is responsible for about 95% of the cases. High systolic blood pressure, i.e., the pressure in the vasculature associated with the expelling of blood from the heart into the aorta, has become the predominant concern in hypertensive patients. The determinants of systolic blood pressure are blood flow, arterial compliance, and arterial wave propagation. Aging results in arterial stiffening which decreases arterial compliance and increases systolic hypertension. As discussed further below reducing hypertension is desirable.

Pressure waves also may be caused by a number of events, e.g., events within the body, such as breathing in the lungs, peristalsis actions in the GI tract, movement of the muscles of the body, or events such as coughing, laughing, external trauma to the body, and movement of the body relative to gravity. As the elasticity of the surrounding tissues and organs, sometimes referred to as compliance, decreases, the propagation of these undesirable pressure waves increases. These undesirable pressure waves have many undesirable effects ranging from discomfort, to stress on the organs and tissue, to fluid leakage such as urinary incontinence, to renal failure, stroke, heart attack and blindness.

Pressure accumulators and wave diffusers are types of devices that can modulate pressure waves in various nonanalogous settings. Accumulator technology is well known and used in hydraulic systems in aircraft, manufacturing equipment, and water supply and distribution since the 1940s. Common types of accumulators include bladder accumulators, piston accumulators, non-separator (air over fluid), and weight loaded type accumulators.

Wave diffusers also affect the transmission of pressure waves in incompressible systems in various settings. The function of such diffusers is to interrupt the progress of a pressure wave and distribute the energy of the wave in so many directions so as to destroy the integrity of a uniform wavefront and its resultant effects. Wave diffusers may be used to protect a specified area from the impact of a wavefront.

Currently, the most common approach to treating hypertension is drug therapy. These drugs include oral medications (systemic) and drugs delivered directly into the bloodstream. These drugs may suffer from side effects, lack of effectiveness and high morbidity. Oral medications typically do not allow immediate relief of symptoms and include side effects such as dry mouth and constipation. Drugs delivered directly into the bloodstream often require continuous or intermittent catheterization for introduction of the therapeutic agents at the clinically appropriate time.

In light of the foregoing, a number of attempts have been made to combat these disorders. These attempts have included pharmaceuticals, meditation and relaxation, and neurostimulation. However, these prior art approaches do not address the reduction in dynamic compliance, e.g., in the vasculature, which results in increased blood pressure and the associated cardiovascular disorders.

SUMMARY OF THE INVENTION

There is provided in accordance with various aspects of the present invention devices and methods of treating a patient with cardiovascular disease, in particular hypertension.

There is provided in one aspect a device for treating hypertension and other cardiovacular maladies. The device comprises a pressure attenuator that can mitigate or attenuate peak pressures. Such a device acting as a pressure attenuator may be used to decrease systolic blood pressure. This may decrease or eliminate the need for antihypertensive medications.

There is provided in accordance with another aspect of the present invention, a device for treating altered vascular compliance and, comprising an attenuation device having an expanded volume within the range of from about 1 cc to about 400 cc. It may also include a valve for permitting filling of the attenuation device through a delivery system.

In another aspect, an implantable blood pressure regulator is provided. The blood pressure regulator includes at least one connection zone and an attenuation zone. The connection zone is suitable for connection to a body conduit, such as a blood vessel. The attenuation zone is movable from a first state to a second state in response to a physiological pressure spike. The movement from the first state to the second state lowers a level of pressure in the body conduit.

In another aspect, a method is provided for treating a patient. The method includes providing a variable volume structure and placing the variable volume structure in pressure communication with the patients' vasculature. The volume of the structure is reduced from a first volume to a second volume in response to a pressure spike in the vessel to reduce the magnitude of the pressure spike.

In another aspect, a method is provided for treating a patient. The method includes providing a conduit having first and second ends and an attenuation zone disposed therebetween. The attenuation zone is configured to expand from a first volume to a second volume in response to a pressure spike in the vessel. At least one of the first and second ends of the conduit is coupled with the patient's vasculature.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 1A illustrates an estimate of the number of adult American that suffer from hypertension.

FIG. 1C illustrates some of the cardiovascular maladies associated with hypertension.

FIG. 1D illustrates pressure in a patient's vasculature in response to a heart cycle.

FIG. 25A is a cross-sectional schematic view as in FIG. 25, illustrating the compression of the primary attenuation device in response to elevated abdominal pressure, and the corresponding expansion of the secondary inflatable component.

FIG. 25B is an enlarged fragmentary schematic view of the inflatable component in FIG. 25A.

FIG. 25C is a pressure curve showing the intravesical pressure compared to the secondary balloon pressure.

FIG. 32B is a close-up view of the duckbill valve in FIG. 32A.

FIG. 34A is an elevated side view of one embodiment of a delivery system for the attenuation device in accordance with one aspect of the present invention.

FIG. 34B is an elevated side view of one embodiment of a delivery system for the attenuation device with the attenuation device exposed and ejected.

FIG. 35A is an elevated side view of one embodiment of a delivery system for the attenuation device in accordance with one aspect of the present invention.

FIG. 35B is an elevated side view of the inflatable attenuation device in FIG. 35A with the sheath slid proximally and the attenuation device exposed.

DETAILED DESCRIPTION OF THE PREFERRED EMBODIMENT

Figure 1B:
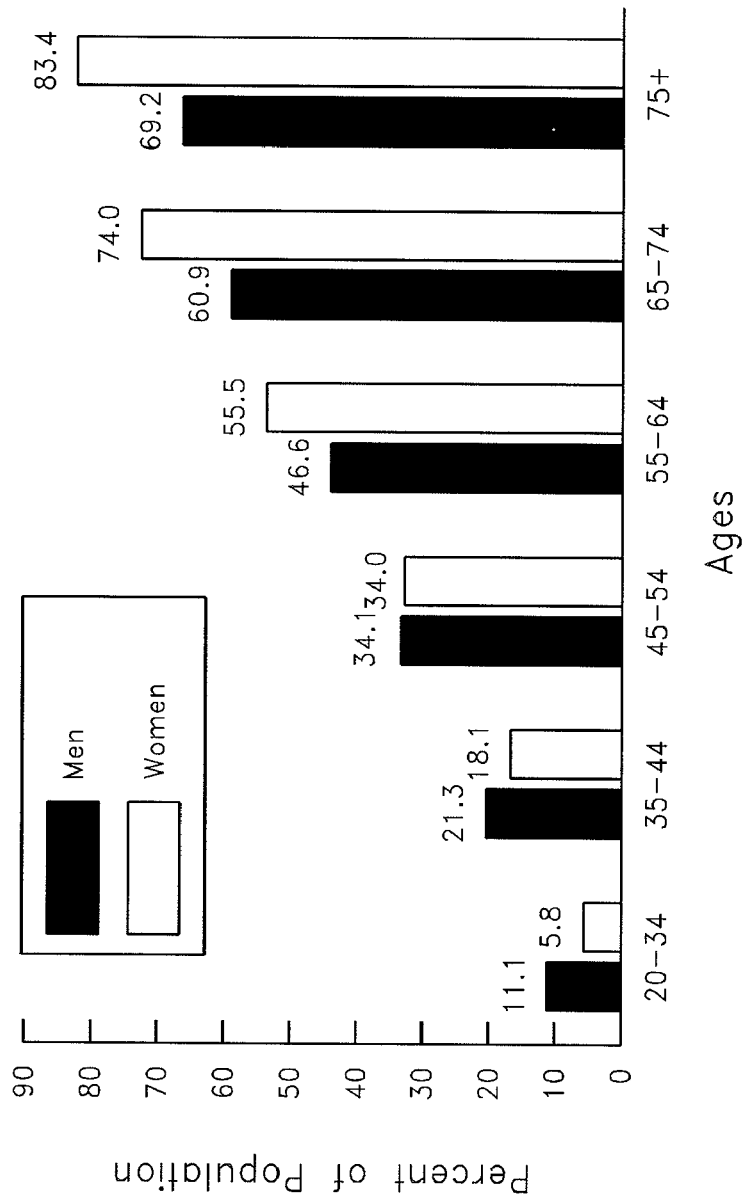
FIG. 1B illustrates an estimate of the increase in frequency of hypertension with age.
Figure 10:
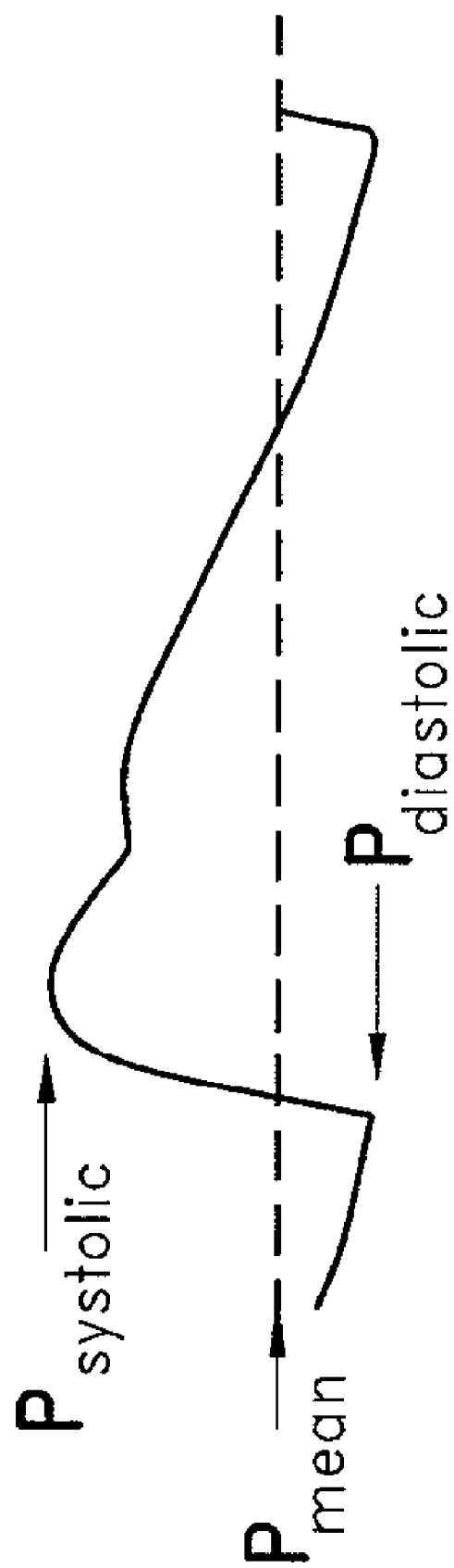
FIG. 10 is a schematic illustration as in FIG. 9, with the attenuation device inflated.

Embodiments of the present invention are directed to methods and apparatus for measuring and/or attenuating and/or baffling transient and or cyclical pressure waves in relatively incompressible materials in organs of the body. Illustrative embodiments of the present invention discussed herein relate generally to the fields of cardiovascular medicine, congestive heart failure, and hypertension. Some embodiments useful in these fields are discussed hereinbelow, e.g., in connection with FIGS. 17A-17F, 29A-29N, and 50A-51B. However, as will be readily understood by those skilled in the art, and as described below, the present invention is not limited to the fields of cardiovascular medicine, congestive heart failure, or hypertension and apparatus of embodiments of the present invention may be used in other lumens and organs of the body as well to attenuate and/or baffle pressure transients or reversibly occupy intraorgan space. For example, as discussed in various aspects below, such technology also can be applied in the fields of urology and gynecology, e.g., in the treatment of disorders of the urinary tract exacerbated by sudden fluctuations in intravesical pressure.

As discussed above, certain embodiments of the present invention can be deployed to dampen or regulate pressure in the cardiovascular system. The cardiovascular system consists of the heart and the vasculature. The vasculature includes a network of blood vessels that include arteries and veins. The arteries, which generally convey oxygenated blood away from the heart, are sometimes collectively referred to as the arterial system. The veins, which generally convey oxygen poor blood back to the heart, are sometimes collectively referred to as the venous system. The heart acts as a pump propelling blood into the arterial system. The heart propels the blood with each heartbeat. A heartbeat can be described as having two phases: systole, i.e. when the heart contracts; and diastole, i.e. when the heart relaxes. The left ventricle of the heart ejects blood during systole and fills with blood during diastole. The left ventricle ejects the blood into the aorta, the largest of the arteries, which acts as a conduit to carry the blood. The aorta in turn gives rise to arterial branches, which further serve as conduits for blood flow.

As the blood is ejected from the heart a pressure wave is generated within the aorta. The peak of this pressure wave is referred to as the systolic blood pressure. As the heart relaxes, a one-way valve (the aortic valve) prevents blood in the aorta from rushing back into the heart. The lowest blood pressure reached in the aorta, during the heartbeat cycle, is referred to as the diastolic blood pressure. The difference between the systolic blood pressure and the diastolic blood pressure is referred to as the pulse pressure. Understandably, there is a normal range for these pressures. An elevation of the systolic and/or the diastolic pressures above these normal ranges is referred to as hypertension.

Hypertension is a common problem that is associated with cardiovascular disease and stroke. Though there are many causes of hypertension, primary (or essential) hypertension is responsible for about 95% of the cases. Systolic blood pressure has become the predominant concern in hypertensive patients. The determinants of systolic blood pressure are blood flow, arterial compliance, and arterial wave propagation. Aging results in arterial stiffening which causes decreased arterial compliance and subsequent systolic hypertension. As discussed further below, pressure attenuators could be used to mitigate peak pressures in a patient's vasculature. A variety of embodiments of medical devices that can act as a pressure attenuators, e.g., to modulate high systolic blood pressure are discussed below. These devices may decrease or obviate the need for antihypertensive medications.

Five Points about Hypertension

Hypertension, which can be defined as systolic blood pressure over 140 units or diastolic blood pressure over 90, is a common problem in Americans. FIG. 1A illustrates that this problem affects roughly 65 million American adults.

Hypertension increases in frequency with age, as illustrated in FIG. 1B.

Hypertension is bad for patients. Hypertension is a primary risk factor for cardiovascular (CV) disease and reduction of blood pressure (BP) reduces the risk of adverse cardiac events and strokes. The relationship between BP and CV disease risk is continuous, and independent of other risk factors.

Hypertension is undertreated. Some have estimated that of those with high blood pressure, 30% are unaware they have it, 34% are on medication and have it controlled, 25% are on medication but don't have their high BP under control, 11% are not on medication.

High Systolic BP has become a predominant concern in hypertension. Idiopathic hypertension has been estimated to be responsible for 90 to 95% of patients with hypertension.

Traditionally, the severity of hypertension was classified principally on the basis of diastolic blood pressure (DBP) which was considered to be the best predictor of risk. FIG. 1D illustrates the relationship between DBP and SBP. However, large cross-sectional studies have shown that end-organ damage in hypertensive people is more strongly associated with systolic BP (SBP) than DBP and recent prospective epidemiologic studies have directed attention to SBP as a better prognostic guide than DBP in predicting cardiovascular and all-cause mortality. In fact, DBP decreases with age. Thus, isolated systolic hypertension (ISH) becomes the predominant form of hypertension in persons >60 years of age. The relative rise in SBP and fall in DBP results in a widening of the pulse pressure ((PP); PP=SBP−DBP). Recent data have underlined the importance of pulse pressure (PP) as an independent CV risk factor in persons over the age of 50 years. In a meta-analysis of outcome trials in patients with ISH, the benefit of treatment was overwhelmingly due to the reduction in SBP rather than DBP. Also, clinical trials and epidemiologic studies have shown that control of SBP is more difficult to achieve than control of DBP.

Determinants of SBP and PP

The level of SBP results from the interaction of three principal factors: 1) characteristics of left ventricular ejection (stroke volume); 2) the cushioning (dampening or compliance) function of the large arteries (the inverse of arterial stiffness); and 3) the propagative and reflective properties of the arterial tree (i.e., intensity of wave reflections and timing of incident and reflected pressure waves).

Figure 1E:
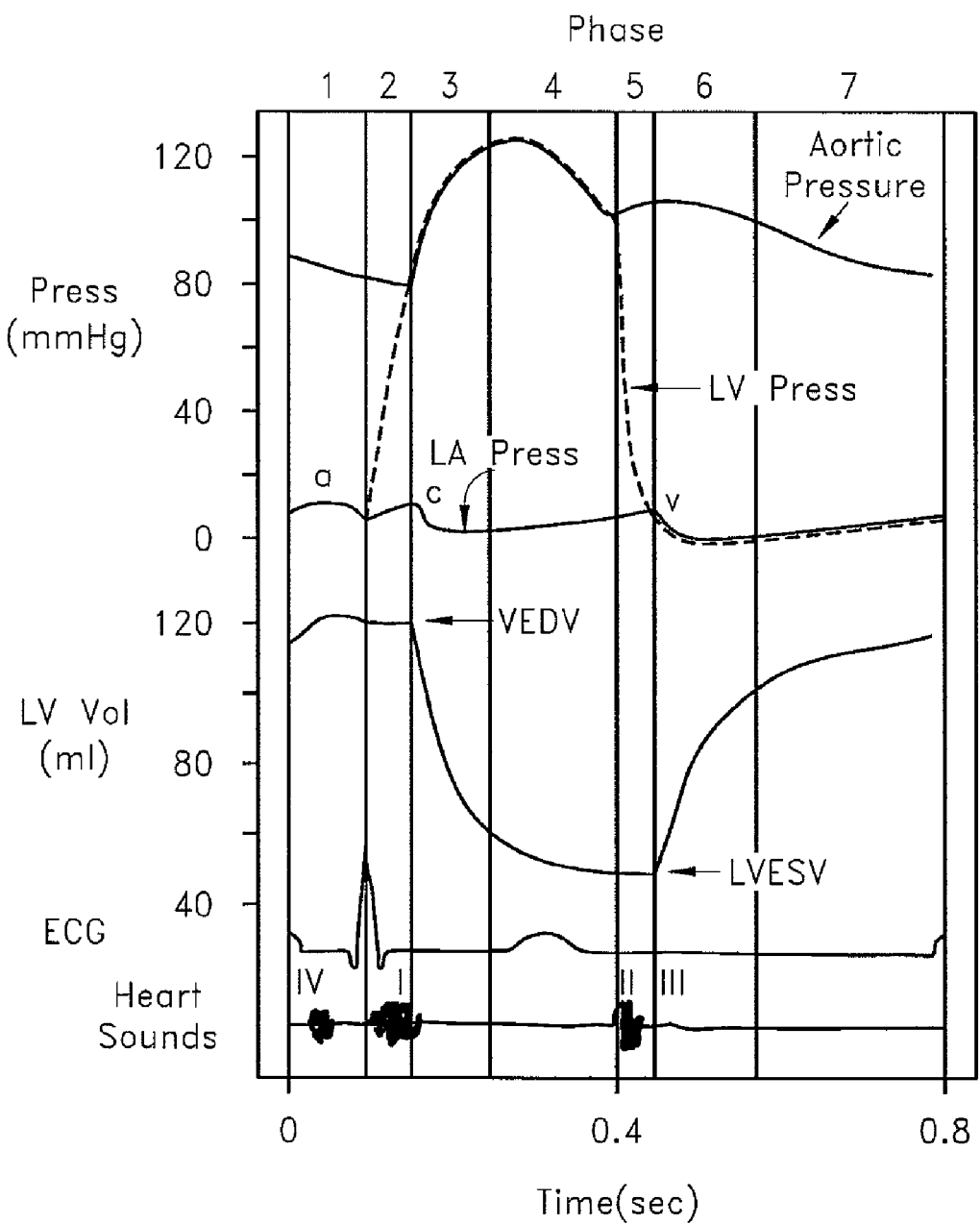
FIG. 1E illustrates blood pressure, left ventricle volumetric output, and ECG output over a heart cycle.

A major role of large arteries is to dampen the pressure oscillations resulting from cyclic LV ejection of discrete volumes of blood, which transforms highly pulsatile flow and pressure into a pattern of more continuous flow in peripheral tissues and organs. During systole, roughly 40% to 50% of stroke volume is forwarded, directly to peripheral tissues, whereas the remainder is stored in the distended aorta and central arteries. Approximately 10% of the energy produced by the heart is diverted for the distension of arteries and "stored" in the walls. During diastole, most of the stored energy causes the aorta to recoil, squeezing the stored blood forward into the peripheral tissues, thereby favoring more continuous flow to the peripheral tissues. For the dampening function to be efficient, the energy necessary for arterial distension and recoil should be as low as possible. That is, for a given stroke volume, the SBP and PP should be as low as possible. See FIG. 1E.

Figure 1F:
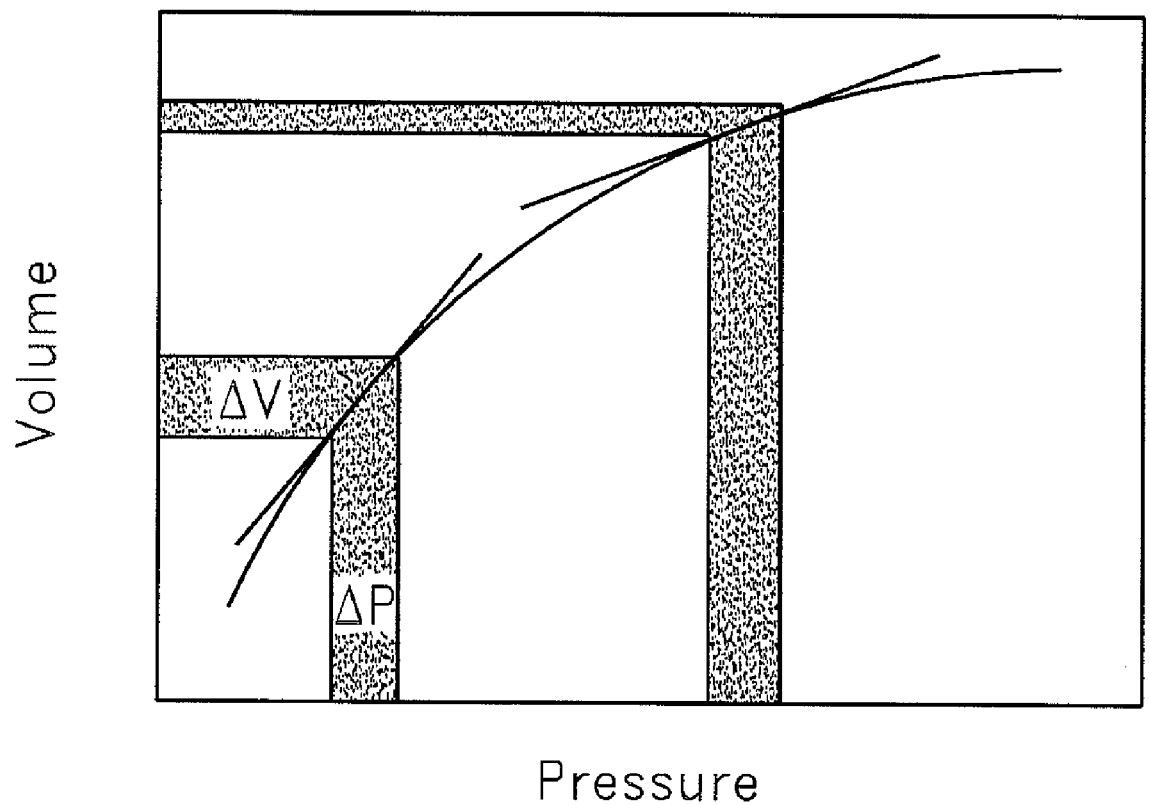
FIG. 1F illustrates a compliance curve for biological tissue such as an artery.

The relationship between distending pressure and the corresponding volume change is described in terms of distensibility (or compliance) or stiffness (or elastance). Stiffness is measured as the change transmural pressure for a given change in volume of the vasculature and is expressed as dP/dV (i.e., elastance, where elastance represents the slope of the pressure-volume relationship at a specified point on the pressure-volume curve). The pressure-volume relationship is nonlinear: distensibility decreases and stiffness increases incrementally at higher BP. That is as the vessel becomes distended, changes in volume yield larger changes in pressure. FIG. 1F illustrates a compliance curve for a biological tissue such as an artery. At low pressures and volumes, compliance (slope of tangent line) is much greater than at high pressures and volume. The change in volume for a given change in pressure is greater at higher compliance. See FIG. 1F.

Figure 1G:
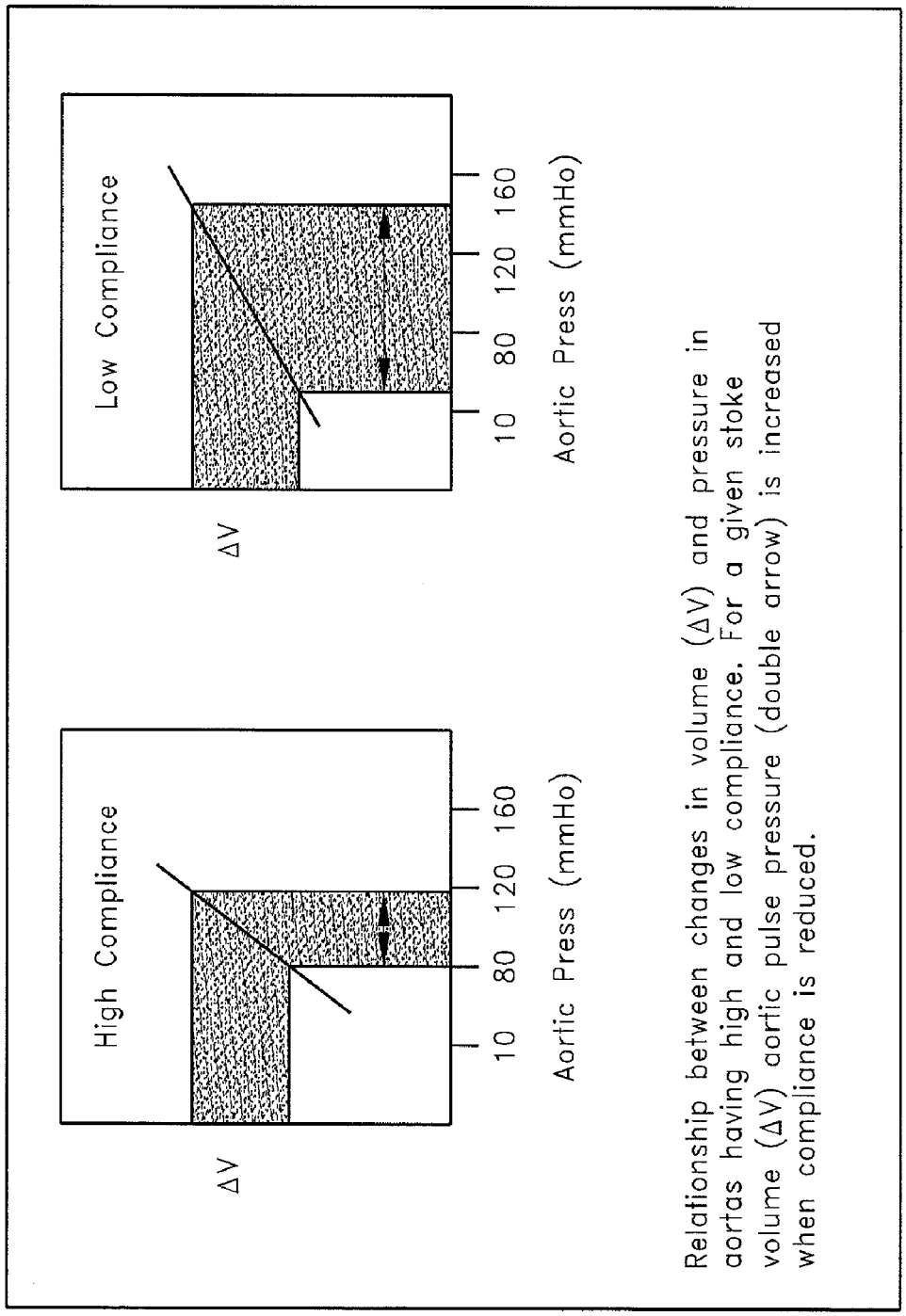
FIG. 1G illustrates a relationship between changes in volume and pressure in aortas having high and low compliance.

A reliable evaluation of arterial stiffness in clinical practice is based on measurement of pulse wave velocity (PWV) along a given large artery. PWV is inversely related to distensibility and directly related to arterial stiffness. The cushioning function is altered by stiffening (decreased distensibility) of arterial walls with increased SBP and decreased DBP resulting in high PP as the principal consequence. See FIG. 1G.

Arterial stiffening influences SBP and PP by a direct and an indirect mechanism. The direct mechanism involves the generation of a higher systolic pressure wave by the left ventricle, which ejects blood into a stiff arterial system with decreased diastolic recoil and reduced diastolic pressure. The indirect mechanism acts via the influence of increased arterial stiffness on PWV and the timing of incident and reflected pressure waves. The interaction of incident and reflected pressure waves is the determinant of the final amplitude and shape of the measured pulse pressure wave at any point along the arterial tree. With increased arterial stiffening and increased PWV, reflected waves tend to return earlier to the central arteries, usually during late systole rather than early diastole. The result is an augmentation of aortic and left ventricle pressures during systole, with reduced aortic pressure during diastole. By favoring early wave reflections, arterial stiffening contributes to the development of left ventricle hypertrophy and decreased subendocardial blood flow.

Arterial stiffening is primarily observed with aging and is responsible for age-associated increase in SBP. Arterial stiffness is increased in isolated systolic hypertension in elderly individuals, in sustained systolic-diastolic hypertension in middle-aged persons, in patients with type-2 diabetes and in patients with end-stage renal disease (ESRD). Arterial stiffening (PWV) and increased wave reflection (augmentation index) are independent predictors of all-cause and CV mortality in patients with essential hypertension, in elderly persons, in diabetic patients, and in ESRD patients. In one technique, augmentation index is measured as the difference between early and late pressure peaks divided by pulse pressure.

Pathophysiologic Approach to Reduction of SBP and PP

Medical treatment of hypertension in younger or middle-aged individuals usually results in roughly proportional declines in SBP and DBP. However, in the case of isolated systolic hypertension, the therapeutic goal is to obtain a preferential decrease of systolic BP while maintaining unchanged diastolic BP. In the broad population, however, drug treatment of hypertension more frequently results in adequate control of DBP than of SBP. Further, patient noncompliance with medical treatment of hypertension remains high because of the lack of symptoms in most hypertensive patients. In total, some estimate that more than 70% of patients with hypertension are not being properly treated for their high blood pressure and, therefore, face significantly higher increased risk for advanced heart and kidney disease and the occurrence of strokes.

Considering the different mechanisms associated with increased SBP, a rational therapeutic approach would reduce vascular, e.g., arterial stiffness and wave reflection as well as overall BP. A pressure attenuator in or in proximity to the arterial system may do just that.

Another environment in which attenuation of pressure can be beneficial is the bladder and related body structures. In particular, certain embodiments of the present invention can be used to dampen transient intravesical pressure including pressure spikes experienced by the urinary tract. During a high frequency transient pressure event, the bladder becomes a relatively non-compliant environment due to a number of factors including the pelvic skeletal structure, the compressive loads of contracting tissues bounding the bladder or the decreased compliance of the musculature, nerve or connective tissue of the bladder. The factors contributing to the reduced compliance of the bladder are aging, anatomic abnormalities or trauma to the structures of the pelvis and abdomen.

Urine is primarily composed of water and is virtually incompressible in the typical pressure ranges present within the human bladder. The relationship between the maximum urethral pressure and the intravesical pressure for normal voiding of the bladder is well defined. With reference to FIG. 1, relaxation of the urethra occurs before the detrusor muscle contracts to cause the intravesical pressure 320 to exceed the urethral pressure 322 during normal voiding.

Figure 2A:
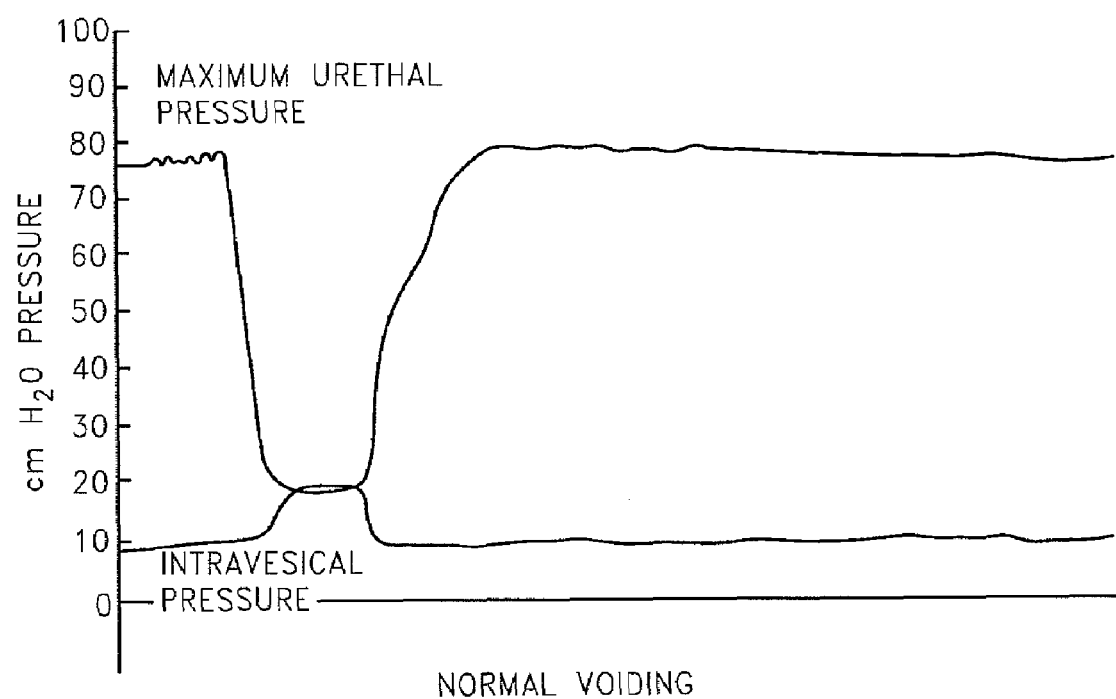
FIG. 2A illustrates intravesical exceeding maximum urethral pressure during normal voiding.
Figure 2B:
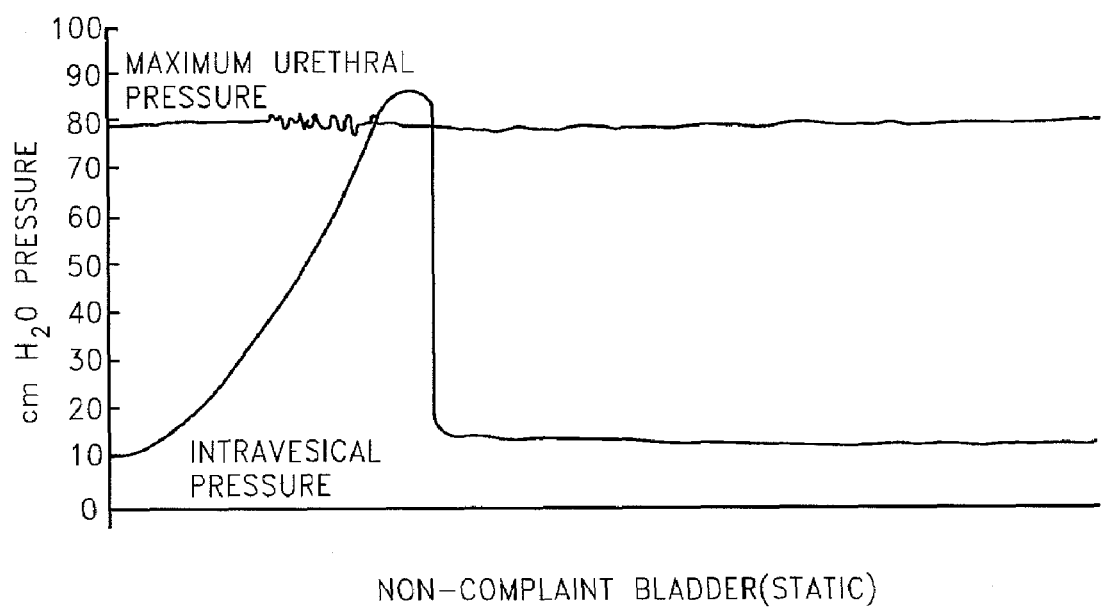
FIG. 2B illustrates the intravesical pressure exceeding the maximum urethral pressure in a noncompliant bladder.

The bladder serves two mechanical functions: 1) low-pressure storage and 2) high-pressure voiding. During the storage or filling phase, the bladder receives an influx of urine from the kidneys. Compliance of the bladder is defined as the ratio of the change in volume to the change in pressure, and the static compliance of the bladder is measured during a typical urodynamic evaluation. The static compliance index is measured by filling the bladder to cystometric capacity and allowing the pressures to equilibrate for a time period of approximately sixty seconds. The static compliance index is calculated by dividing the bladder capacity by the Detrusor pressure at the end of filling. A normal bladder will typically exhibit static compliance between 15 and 30 ml/cm $H_2O$. A low static compliance bladder typically will have a compliance index of less than 10 ml/cm $H_2O$. With reference to FIG. 2 which illustrates different pressures for a non-compliant bladder, a low static compliance bladder typically is poorly distensible and has a high end-filling pressure. The intravesical pressure 320 must increase to higher levels to exceed the maximum urethral pressure 324. The steady state compliance of the bladder is used to diagnose patients with naturopathic problems such as damage to the lower motor neurons, upper motor neurons, or multiple sclerosis. In addition, the steady state compliance of the bladder is also used, in some cases, to attempt to diagnose problem of incontinence, including urgency, frequency and cystitis.

In general, intravesical pressure spikes result from volumetric tissue displacement in response to gravity, muscular activity or rapid acceleration. The lack of compliance of the bladder and the urine contained in the bladder with respect to events of high frequency, result in minimal fluidic pressure attenuation of the higher frequency pressure wave(s) and results in high intravesical pressures that are directly transmitted to the bladder neck and urethra, which may or may not cause detrusor contractions. Under these conditions, the urethra may act as a volumetric pressure relief mechanism allowing a proportional volume of fluid to escape the bladder, to lower the intravesical pressure to a tolerable level. The urethra has a maximum urethral pressure value, and when the intravesical pressure exceeds the maximum urethral pressure, fluid will escape the bladder. Under these conditions, nerve receptors in the bladder and/or bladder neck and/or trigone trigger a detrusor contraction that may lead to matriculation (frequency) or may subside without matriculation (urgency) or may lead to the intravesical pressure exceeding the maximum urethral pressure resulting in fluid escaping the bladder (incontinence). Under these conditions, waves hitting and/or expanding the bladder wall, may cause a patient with cystitis to exhibit significant pain.

Incontinence is common in males who have undergone radical prostatectomy, particularly where the sphincter has been compromised. In these patients, attenuation in the bladder reduces the intravesical peak pressures, resulting in less urine leakage. The attenuation requirements in these patients can include short duration pressure changes—such as, for example, 50 to 400 ms—and long duration pressure changes—such as, for example, greater than 500 ms—depending on the magnitude of damage to the urinary sphincter.

The inventors of the present application have recognized that for the vast majority of patients suffering from problems of urinary tract disorders such as frequency, urgency, stress and urge incontinence and cystitis, the cause and/or contributor to the bladder dysfunction is a reduction of overall dynamic bladder compliance rather than steady state bladder compliance. These patients may often have bladders that are compliant in steady state conditions, but have become non dynamically compliant when subjected to external pressure events having a short duration of, for example, less than 5 seconds or in some cases less than 2 seconds or even less than 0.5 seconds. Reduction in dynamic compliance of the bladder is often caused by some of the same conditions as reduction of steady state compliance including aging, use, distention, childbirth and trauma. The anatomical structure of the bladder in relation to the diaphragm, stomach, and uterus (for women) causes external pressure to be exerted on the bladder during talking, walking, laughing, sitting, moving, turning, and rolling over.

Figure 3:
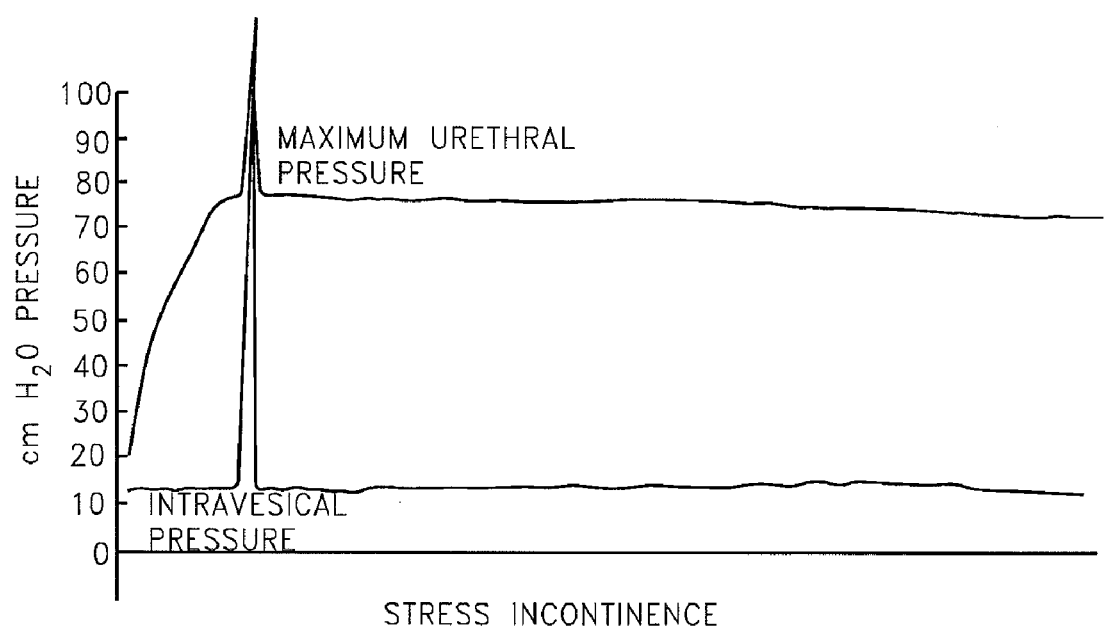
FIG. 3 illustrates an intravesical pressure spike exceeding the maximum urethral pressure during stress incontinence.

The relationship between intravesical pressure 320 and the maximum urethral pressure 324 for a patient suffering from stress incontinence due to lack of dynamic compliance in the bladder is illustrated in FIG. 3. When the patient coughs (or some other stress event occurs), if the bladder does not have sufficient dynamic compliance in that frequency range a spike 326 will occur in the intravesical pressure. Intravesical pressure spikes in excess of 120 cm $H_2O$ have been urodynamically recorded during coughing, jumping, laughing or sneezing. When the intravesical pressure exceeds the maximum urethral pressure value, leakage occurs. In order to retain urine during an intravesical pressure spike, the urinary retention resistance of the continent individual must exceed the pressure spike. Urinary retention resistance can be simplified as the sum total of the outflow resistance contributions of the urethra, bladder neck and meatus. In female patients, it is generally believed that the largest resistance component is provided by the urethra. One measure of urinary resistance is the urodynamic measurement of urethral leak pressure. The incontinent individual typically has a urethral leak pressure less than 80 cm $H_2O$. The decline of adequate urinary retention resistance has been attributed to a number of factors including reduced blood flow in the pelvic area, decreased tissue elasticity, neurological disorders, deterioration of urethral muscle tone and tissue trauma.

In Practice, the urethral leak point pressure is determined by filling the bladder with a known amount of fluid and measuring the intravesical and abdominal pressures when there is a visible leak from the urethra while the patient is "bearing-down" (valsalva). With an attenuation device in the bladder, the measured intravesical leak point pressure typically increases due to the adsorption of some the abdominal energy by the attenuation device. In this case, the patient has to push harder to achieve the same intravesical pressure. Since the abdominal muscles and muscles surrounding the urethra both contract simultaneously during a valsalva maneuver, the measured intravesical leak point pressure and urethral resistance increases when the attenuation device ins in the bladder.

Figure 4:
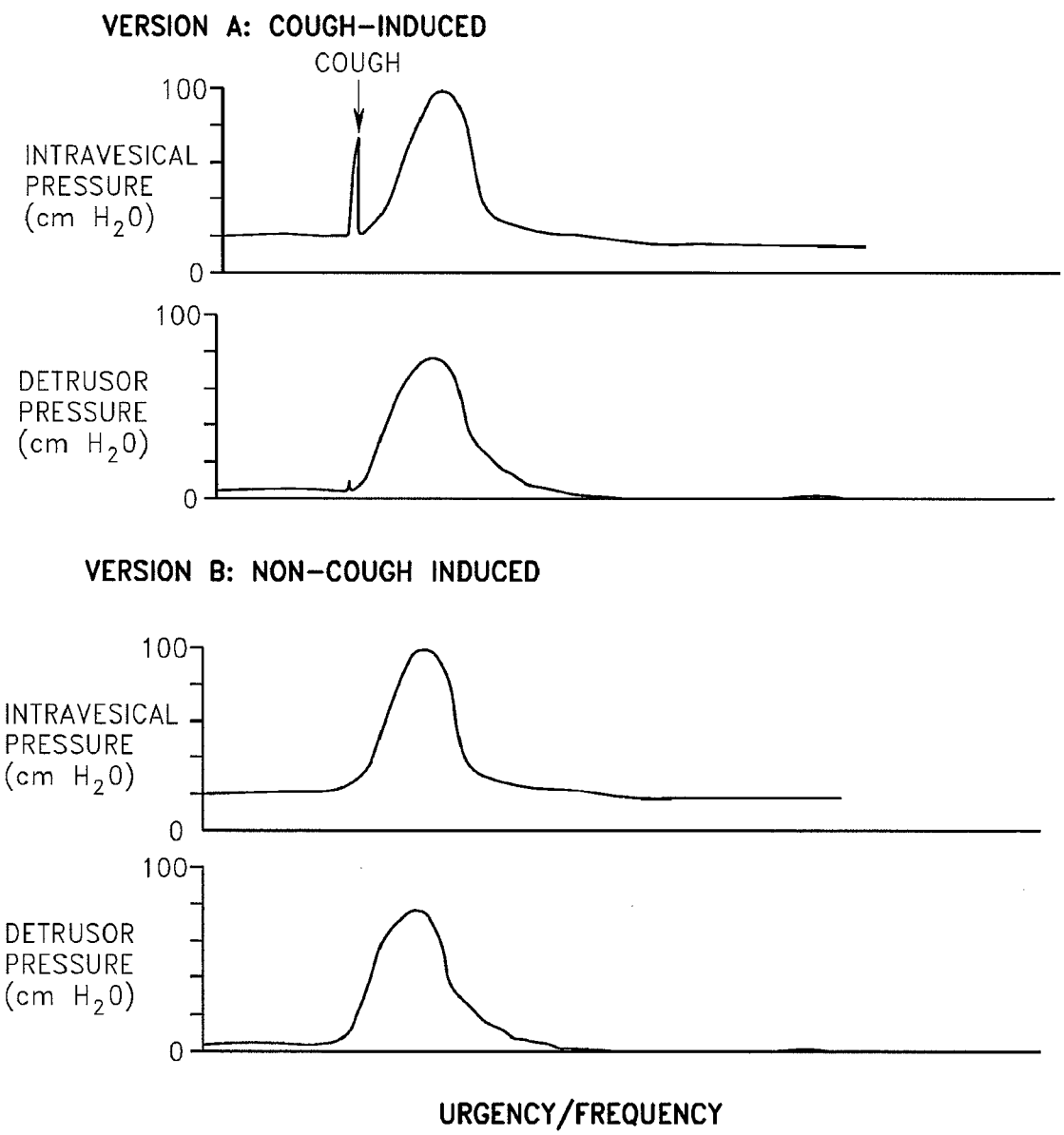
FIG. 4A illustrates the relationship between intravesical pressure and detrusor pressure during cough-induced urgency or frequency.
FIG. 4B illustrates the relationship between intravesical pressure and detrusor pressure during non-cough-induced urgency or frequency.

Urinary disorders, such as urgency, frequency, otherwise known as overactive bladder, and interstitial cystitis are caused or exacerbated when rapid pressure increases or rapid volume increases or other irritable conditions within the bladder cause motor neurons to send signals to the brain to begin the cascade of events necessary for urination. External pressure exerted on the bladder may result in a detrusor contraction that may result in urgency, frequency or incontinence. See FIGS. 4A (cough-induced urgency/frequency) and 4B (non-cough-induced urgency/frequency). With reference to FIG. 4A, a coughing event 328 induces increased intravesical pressure 320 which results in increased detrusor pressure 330. An increase in the detrusor pressure 330 generally is associated with increased urgency, frequency, or incontinence. Urinary disorders such as interstitial cystitis or irritable bladder conditions are a chronic inflammatory condition of the bladder wall, which includes symptoms of urgency and/or frequency in addition to pain. Therefore, the problem of a pressure spike in the functionally noncompliant bladder can be further exacerbated by a nearly simultaneous contraction of the bladder and a relaxation of the urethra.

Certain embodiments of the present invention provide for methods and devices for measuring and reporting the dynamic compliance of the bladder. One method of determining dynamic compliance includes the rapid infusion of a volume of fluid into the bladder with immediate measurement of the intravesical pressure. The volume would be more than 50 ccs, preferably greater than 100 cc and more preferably greater than 200 cc. The rate of infusion would be less than 10 seconds, preferably less than 5 seconds, and more preferably less than 2 seconds. One embodiment of the present invention includes a two lumen catheter placed within the bladder, wherein a compliant balloon is rapidly filled with a non-compliant material, such as saline is infused through one lumen of the catheter. The resulting intravesical pressure is measured from the other lumen of the catheter. This infusion can be with a syringe, a mechanically assisted syringe or pump.

An additional embodiment provides methods and devices for treating and/or compensating for reduced dynamic compliance of the bladder. In one embodiment, a device having a compressible element is placed within the human urinary bladder, in a manner that allows the compressible element to act as a pressure accumulator or attenuator to attenuate transient pressure events. The term accumulator refers generally to devices that attenuate pressure, force, or energy in a given locale by absorbing and/or shifting away said pressure, force, or energy from said locale. The term attenuator refers generally to devices that attenuate pressure, force, or energy by dissipating or dampening said pressure, force, or energy. Gases such as atmospheric air, carbon dioxide and nitrogen are very compressible in the pressure ranges typically encountered in the human bladder, and these gases may be used in attenuation devices inserted in the bladder. Furthermore, when compared to the tissues encompassing urine, these gases are significantly more compliant than the immediate environment. The addition of a proportionately smaller volume of unpressurized gas acts as a low rate spring in series with the native fluidic circuit of the urinary tract. Additional information on the basic scientific principles underlying pressure accumulators and methods for controlling transient changes in pressure can be found in E. BENJAMIN WYLIE ET AL., FLUID TRANSIENTS IN SYSTEMS §§ 6, 10, 11, 13 (1993); the entirety of these 2sections are hereby incorporated by reference herein and made a part of this specification.

Figure 45:
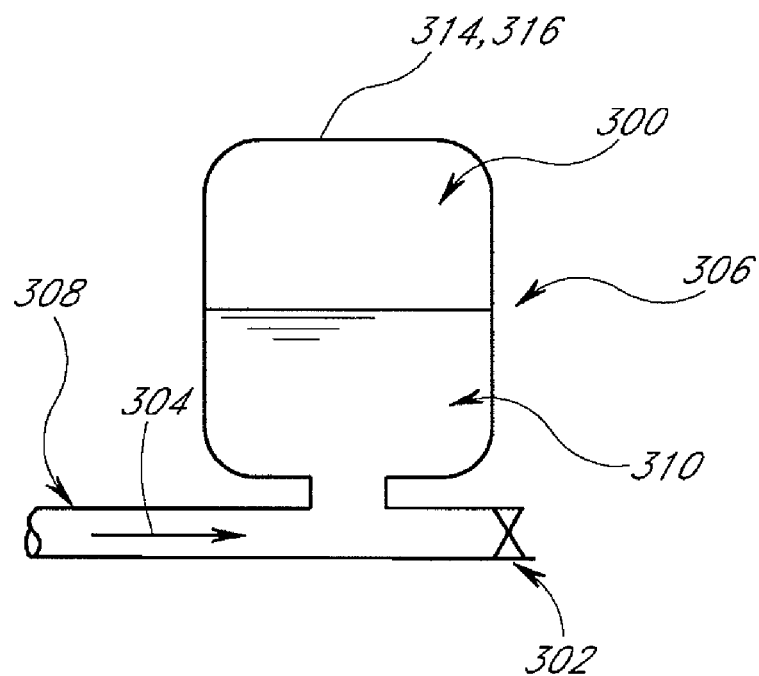
FIG. 45 is a schematic view of one embodiment of an accumulator.

Accumulators can be designed to keep the pressure from exceeding a predetermined value or to prevent low pressures. Accumulators can be designed to protect against rapid transients as well as against longer-period surges in a system. One example of an accumulator is a closed container partially filled with the system liquid and topped with air or gas. The gas may be in contact with the liquid, in which case an air compressor, or gas supply, is used to maintain the proper mass of air or gas, or the gas may be separated from the liquid by a flexible membrane or a piston. The accumulator generally operates at the local system pressure. With reference to the embodiment illustrated in FIG. 45, if the valve 302 of the accumulator 300 is closed abruptly the flow 304 enters the air chamber 306, the air is compressed, and the flow to the main pipeline 308 is gradually reduced as the pressure builds up, thereby provides a way to reduce the peak pressure in the chamber 306, the main pipeline 308, and other downstream plumbing and equipment.

Figure 46:
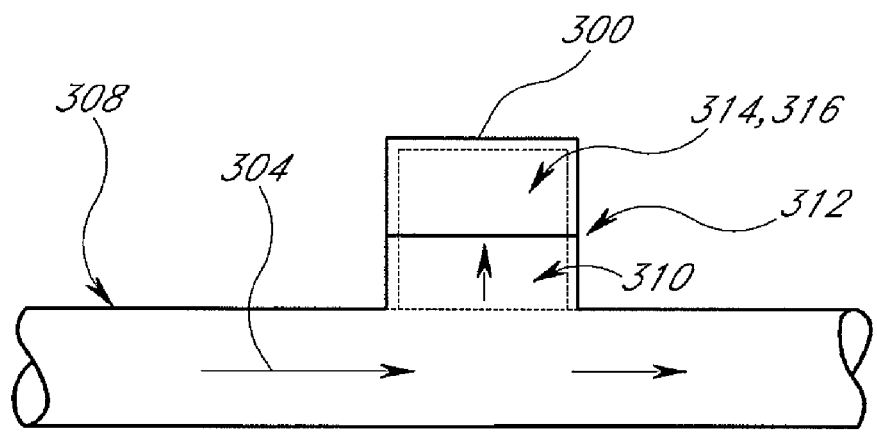
FIG. 46 is a schematic view of a simple accumulator.

In one embodiment, shown in FIG. 46, a single accumulator 300 is assumed to have the same pressure throughout its volume at any given instant. Here, the compressibility of the liquid 310 in the vessel 312 is considered negligible compared with air compressibility. Assuming inertia and friction are negligible, the gas 314 is assumed to follow the reversible polytropic relation $H_A V^n = C_A$, where $H_A$ is the absolute head equal to the gage plus barometric pressure heads, where $V^n$ is the gas volume 316, where n is the polytropic exponent, and where $C_A$ is a constant. The exponent n depends on the thermodynamic process followed by the gas 314 in the vessel 312. If a perfect gas is assumed, at one extreme the process may be isothermal, n=1, or at the other limit it may be isentropic, in which case n=1.4 for air. It should be noted that computation of the aforementioned values, as well as analogous or related values, can be determined by those skilled in the art by taking into consideration the foregoing discussion.

In another embodiment, the compression of the enclosed volume of air creates heat that is dissipated into the relatively infinite heat sink of the body. The balance of the energy absorbed by the compressed air is simply returned at a different, lower frequency into the fluidic circuit when the gas is allowed to expand, as the surrounding tissues return to their initial positions. The addition of adequate local compliance can effectively attenuate transient intravesical pressure spikes to levels below the patient's leak pressure, thus obviating the need for relief by means of volumetric displacement of urine, and/or preventing the stimulation of signals to the brain that cause bladder contractions.

In accordance with one aspect of the present invention, an attenuation device is placed within the human urinary bladder. The attenuation device is intended to be untethered in the bladder and is intended to remain in the bladder for between several hours and one year, between one week and six months, or between one and three months. The attenuation device is a small elastomeric air cell with a relaxed (unstretched) volume of between 1 and 500 cc, more preferably between 1 and 100 cc and more preferably still, between 3 and 25 cc. The attenuation device is a unitary component but can be comprised of two or more subcomponents. The attenuation device has a substantially uniform wall thickness of between 0.25 inch to 0.0001 inch, more preferably between 0.0005 inch and 0.005 inch, but could be designed to vary greatly, and still perform the intended function. In the embodiment described above, attenuation devices having air cells that are free-floating in the bladder have been described. In other embodiments of the present invention, air cells or similar attenuation devices could be surgically affixed to the bladder wall through the use of suture, staples and other accepted methods or placed submucosally or intramuscularly within the bladder wall. Other embodiments could also include attenuation devices with programmable, variable and adjustable buoyancy by using ballasting, specific inflation/deflation solutions, alternative materials of construction or by other means.

Figure 5:
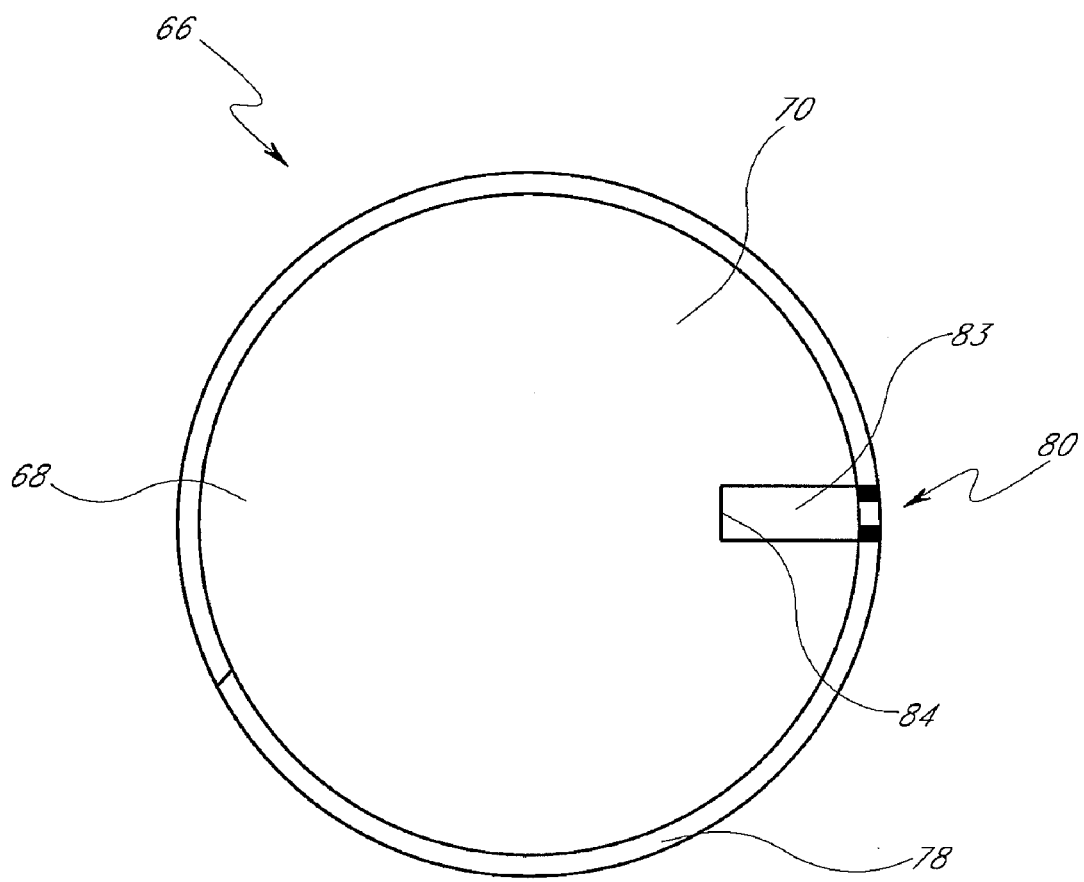
FIG. 5 is a schematic top plan view of an inflatable attenuation device in accordance with one aspect of the invention.
Figure 5A:
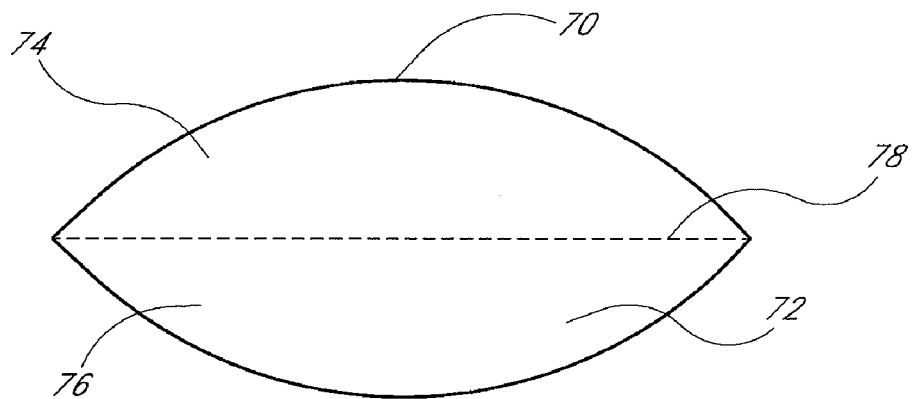
FIG. 5A is a side elevational cross-section through the attenuation device of FIG. 5.

Referring to FIGS. 5 and 5A, there is illustrated one embodiment of an attenuation device 66 which comprises a moveable wall such as on an inflatable container 68. The inflatable container 68 is illustrated as having a generally circular profile, although other profiles may be utilized in accordance with the present invention. The diameter of the inflatable container 68 may be varied within the range of from about 0.25 inches to about 6 inches, in an application of the invention involving the implantation of only a single attenuation device. Many embodiments of the inflatable containers 68 will have a diameter within the range from about 1 inch to about 3 inches, with a total volume within the ranges recited above. In general, the specific dimensions and configuration of the inflatable container 68 are selected to produce an attenuation device having a desired volume and a desired dynamic compression range, and may be varied from spherical to relatively flat as will be apparent to those of skill in the art based upon the disclosure herein. In certain embodiments, two or three or more discreet inflatable containers 68 are utilized. The sum of the volumes of the multiple containers will equal the desired uncompressed displacement.

The inflatable container 68 illustrated in FIGS. 5 and 5A comprises a flexible wall 70, for separating the compressible contents of the attenuation device 66 from the external environment. Flexible wall 70 comprises a first component 74 and second component 76 bonded together such as by a seam 78. In the illustrated embodiment, the first component 74 and second component 76 are essentially identical, such that the seam 78 is formed on the outer periphery of the inflatable container 68. Seam 78 may be accomplished in ay of a variety of manners known in the medical device bonding arts, such as heat bonding, adhesive bonding, solvent bonding, RF or laser welding, or others known in the art.

The flexible wall 70 formed by a bonded first component 74 and second component 76 define an interior cavity 72. As is discussed elsewhere herein, interior cavity 72 preferably comprises a compressible media, such as gas, or foam. Other media or structures capable of reduction in volume through a mechanism other than strict compression may also be used. For example, a material capable of undergoing a phase change from a first, higher volume phase to a second, lower volume phase under the temperature and pressure ranges experienced in the bladder may also be used.

In order to minimize trauma during delivery of the attenuation device 66, the attenuation device is preferably expandable from a first, reduced cross-sectional configuration to a second, enlarged cross-sectional configuration. The attenuation device 66 may thus be transurethrally deployed into the bladder in its first configuration, and enlarged to its second configuration once positioned within the bladder to accomplish the pressure attenuation function. Preferably, a crossing profile or a greatest cross-sectional configuration of the attenuation device 66 when in the first configuration is no greater than about 24 French (8 mm), and, preferably, no greater than about 18 French (6 mm). This may be accomplished, for example, by rolling a deflated inflatable container 68 about a longitudinal axis, while the interior cavity 72 is evacuated.

Once positioned within the bladder, the interior cavity 72 is filled with the compressible media to produce a functional attenuation device 66. The present inventors contemplate fill pressures and volumes of generally less than about 1.5 atmospheres and 50 ml, respectively, and, in some embodiments, less than 0.5 atmospheres and 25 ml, respectively, such as, for example, in the case of an air filled collapsible attenuation device 66. In general, the fill pressure and volume are preferably no more than necessary to keep the attenuation device 66 inflated in the absence of pressure spikes. Excessive pressure and volume within the attenuation device 66 may shorten the dynamic range of the attenuation device 66, thereby lessening the sensitivity to attenuate pressure spikes. Pressures of less than 1 atmosphere, or even vacuums may be utilized if the structure of the attenuation device is sufficient to balance the negative pressure to produce a net force such that attenuation can occur. This may be accomplished, for example, in an embodiment where the attenuation device 66 is provided with a self-expandable support structure (e.g. nitinol wire frame), which provides a radially outwardly directed bias.

The resiliency of the material of the attenuation device, and the pressure and volume of the inflation media are preferably matched to produce a compression cycle time which is fast enough to allow the attenuation device to respond to increases in pressure while not have a clinically detrimental effect on voiding. For example, the attenuation device's compression cycle preferably bottoms out or reaches a maximum in a sufficiently short period of time as detrussor pressure increases that adverse clinical effects on voiding are minimized or prevented.

To facilitate filling the interior cavity 72 following placement of the attenuation device 66 within the bladder, the inflatable container 68 is preferably provided with a valve 80. In the illustrated embodiment, valve 80 is positioned across the seam 78, and may be held in place by the same bonding techniques utilized to form the seam 78. Valve 80 may be omitted in an embodiment in which the attenuation device 66 is self-expandable.

Valve 80 generally comprises an aperture 82, for receiving a filling tube therethrough. Aperture 82 is in fluid communication with the interior cavity 72 by way of a flow path 83. See FIGS. 5 and 7C. At least one closure member 84 is provided for permitting one way flow through flow path 83. In this manner, a delivery system and filling device can be utilized to displace closure member 84 and introduce compressible media into the interior cavity 72. Upon removal of the filling device, the closure member 84 prevents or inhibits the escape of compressible media from the interior cavity 72 through the flow path 83.

Thus, the closure member 84 is preferably movable between a first orientation in which it obstructs effluent flow through the flow path 83 and a second position in which it permits influent flow through the flow path 83. Preferably, the closure member 84 is biased in the first direction. Thus, forward flow may be accomplished by either mechanically moving the closure member 84 into the second position such as using a filling tube, or by moving the closure member 84 into the second position by exerting a sufficient pressure on the compressible media in flow path 83 to overcome the closure bias. Certain specific valve structures will be described in connection with FIGS. 8A-E below. However, any of a wide variety of valve designs may be utilized in the attenuation device 66 of the present invention as will be apparent to those of skill in the art in view of the disclosure herein.

In one embodiment, the attenuation device consists of an air cell consisting of 0.0018 inch thick polyurethane sheets that have been bonded together to form a 2 3/8 inch circle in top view. In one embodiment, the attenuation device is made from polyurethane and is intended to be inflated to a pressure slightly above atmospheric pressure and a volume less than 50 ml or generally within the range of 0.01 to 1 psi above atmospheric pressure and less than 25 ml. Integral to the sealing edge 78 of the attenuation device holds a port/valve 80 utilized in the placement, inflation and release of the attenuation device. Into the port/valve structure 80 is placed the distal end of a rigid fill tube (0.050" OD) 50. The valve 80 employed may be one of the valves described in U.S. Pat. No. 5,144,708, which is incorporated herein by reference. In another embodiment, the attenuation device may be ultrasonically, radio frequency, adhesively or heat sealed in situ following inflation, in which case the valve may be omitted.

Biocompatible lubricating substances may be used to facilitate the placement of the attenuation device/fill tube within the lumen of the introducer. The distal tip of the introducer has been modified to allow a minimally traumatic presentation of the attenuation device to the urethral tissue. Biocompatible lubricating substances may be used to facilitate the insertion of the attenuation device into the urethra.

In one embodiment, the attenuation device incorporates biocompatible coatings or fillers to minimize irritation to the bladder wall and mucosa and/or to inhibit the formation of mineral deposits (encrustation). The materials can be coated onto the surface or incorporated within the wall of the attenuation device.

Figure 6:
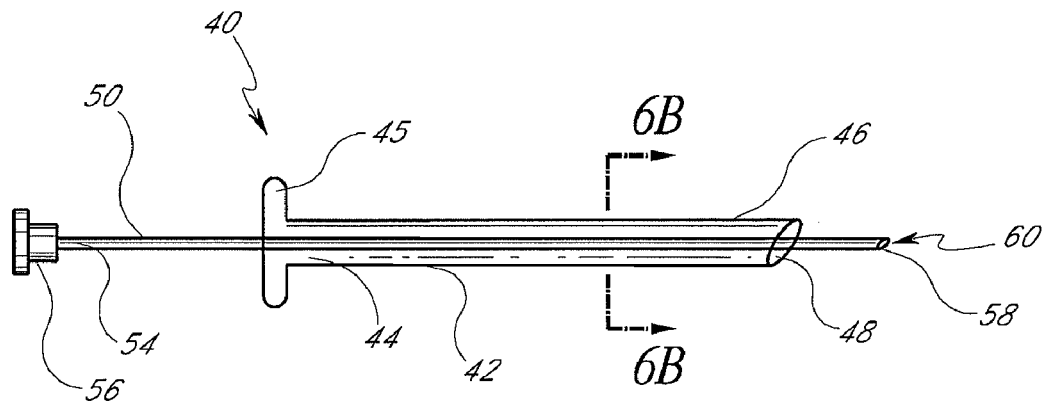
FIG. 6 is a side elevational schematic view of a delivery system for deploying an attenuation device in accordance with one aspect of the present invention.

Referring to FIG. 6, there is illustrated one delivery system for deploying the attenuation device into the treatment site, such as, for example, the bladder, in accordance with the present invention. In general, the delivery system 40 is designed to advance an attenuation device 66 (not illustrated) transurethrally into the bladder while in a first, reduced cross-sectional configuration, and to thereafter inflate or enlarge or permit the expansion of the attenuation device to a second, implanted orientation. The particular configuration and functionality of the delivery system 40 will therefore be governed in large part by the particular design of the attenuation device 66. Thus, as will be apparent to those of skill in the art in view of the disclosure herein, various modifications and adaptations may become desirable to the particular delivery system disclosed herein, depending upon the construction of the corresponding attenuation device.

The delivery system 40 comprises an elongate tubular body 42 having a proximal end 44 and a distal end 46. Tubular body 42 is dimensioned to transurethrally access the bladder. Thus, the tubular body 42 preferably has an outside diameter of no more than about 8 mm, and, preferably, no more than about 4 mm. The length of the tubular body 42 may be varied, depending upon the desired proximal extension of the delivery system 42 from the urethra during deployment. In general, an axial length of tubular body 42 within the range of from about 1" to about 10" for adult female patients and from about 4" to about 30" for adult male patients is currently contemplated.

The tubular body 42 is provided with at least one central lumen 48 extending axially therethrough. Central lumen 48 axially slideably receives a filling tube 50, for filling the attenuation device 66. Filling tube 50 comprises a tubular body 52 having a proximal end 54 and a distal end 58. An inflation lumen 60 extends throughout the length of the tubular body 52, and is in fluid communication with a proximal hub 56. Hub 56 comprises a connector such as a standard luer connector for coupling to a source of inflation media.

The tubular body 52 has an axial length which is sufficiently longer than the axial length of tubular body 42 to allow the proximal hub 56 to remain accessible to the clinician and accomplish the functions of deploying and filling the attenuation device 66. In one embodiment, an outer tubular sheath (not illustrated) is slideably carried over the tubular body 42, and is spaced radially apart from the tubular body 52 to define an annular cavity for receiving a rolled attenuation device 66 therein. In this manner, the deflated attenuation device can be rolled around a distal portion of the tubular body 52 and carried within the tubular sheath during transurethral placement. Once the delivery system 40 has been properly positioned, proximal retraction of the outer sheath with respect to the tubular body 52 exposes the deflated attenuation device 66. A source of inflation media is coupled to the proximal hub 56, and media is introduced distally through central lumen 60 to inflate the attenuation device 66. Following inflation of the attenuation device 66, the delivery system 40 is disengaged from the attenuation device 66, such as by retracting the filling tube 50 with respect to the tubular body 42. A distal stop surface 47 on tubular body 42 prevents proximal movement of the attenuation device 66 as the filling tube 50 is proximally retracted. Delivery system 40 is thereafter removed from the patient, leaving the inflated attenuation device 66 within the bladder.

Figure 6A:
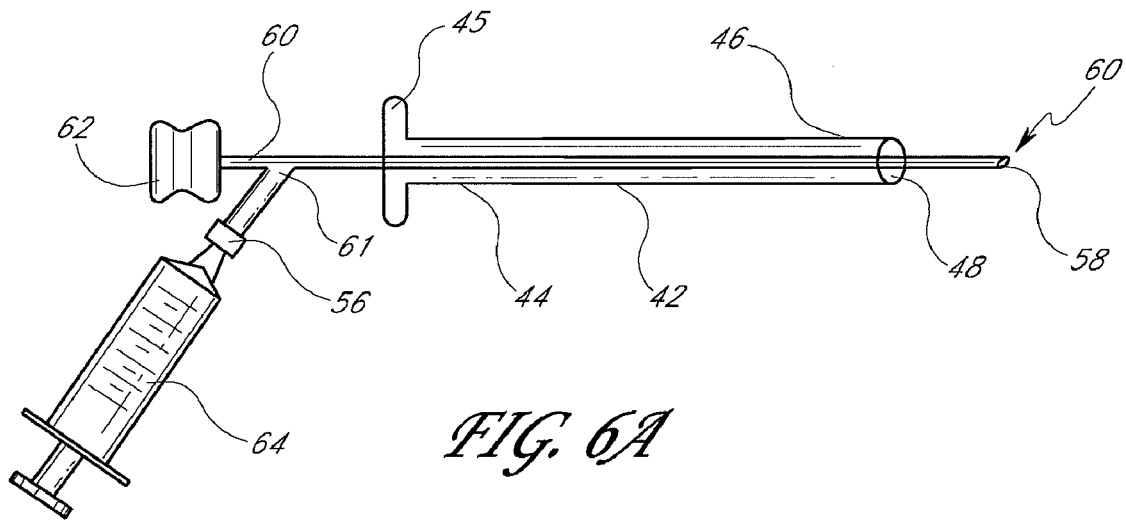
FIG. 6A is a side elevational schematic view of one embodiment of the present invention.
Figure 6B:
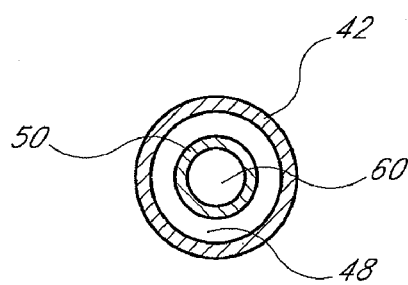
FIG. 6B is a cross-section through the line 6B-6B in FIG. 6.

With reference to FIGS. 6A and 6B, there is illustrated a modified version of the delivery system 40. In this embodiment, a control 62 is connected by way of a proximal extension 60 to the tubular body 52. The control 62 may be in any of a variety of forms, such as a knob or a pistol grip. The control 62 may be grasped by the clinician, and utilized to axially advance or retract the filling tube 50 within the tubular body 42. The proximal hub 56 is connected to the tubular body 52 by way of a bifurcation 61. As will be appreciated by those of skill in the art, the central lumen 60 extends through the bifurcation 61 and to the proximal hub 56. Proximal extension 60 may comprise a blocked tubular element or a solid element. An inflation source 64 such as a syringe filled with a predetermined volume of air or other media may be connected to the proximal hub 56.

For patient comfort, the introducer is suitably sized to easily pass through the urethra (approximately 0.5 to 4 mm diameter). Visual feedback is provided to the clinician by means of insertion depth indicators along the longitudinal length of the introducer. The introducer may also have an adjustable depth stop that allows the clinician to pre-set the desired insertion depth. Once the delivery system has been inserted into the urethra to the desired depth the introducer is then kept in a fixed position and the attenuation device mounted on the distal end of the fill tube is then extended in the lumen of the bladder. The attenuation device is then filled with the indicated volume of gas from the attached syringe or similar device. See FIGS. 9, 10, 11, and 11A. Once properly inflated, the attenuation device is released from the fill tube using the tip of the introducer as an opposing force disengaging the attenuation device valve from the fill tube. The fill tube is then retracted completely into the lumen of the introducer and the entire delivery system is then withdrawn from the patient. The attenuation device is left in place for the clinically indicated period of time.

One aspect of the present invention relates to the delivery of a very flexible, thin walled device. Delivery of an attenuation device is typically accomplished via a suitably sized introducer or possibly through the working channel of an endoscope or cystoscope. However, in certain instances the columnar strength of an attenuation device may make it difficult to be pushed through such channels. A further requirement of any delivery system is that it be atraumatic, and not pose a threat of tissue damage. This invention addresses such issues, and offers improvements for accomplishing delivery of such attenuation devices as disclosed in U.S. Application Ser. No. 60/197,095, filed Apr. 14, 2000, titled DEVICES AND METHODS FOR BLADDER PRESSURE ATTENUATION, and U.S. application Ser. No. 09/723,309, filed Nov. 27, 2000, titled DEVICES AND METHODS FOR ATTENU- ATION OF PRESSURE WAVES IN THE BODY, both of which are incorporated by reference herein in their entireties.

The attenuation device is normally folded on itself along its diameter in order to present a low profile for insertion into, for example, a patients bladder transurethrally. In this configuration the attenuation device has insufficient column strength to withstand the forces of insertion without buckling. If the attenuation device buckles it cannot be inserted. Following insertion the attenuation device is inflated via an inflation tube to which it is re-mounted. After inflating the inflation tube is detached and the attenuation device is freed. By way of illustration, various embodiments of the invention will be described in the exemplary context of transurethral insertion of a delivery system into a patient's bladder.

In one embodiment, shown in FIGS. 34A and 34B, there is provided an delivery system for the attenuation device which consists of an inner fenestrated tubular member which is provided with an atraumatic rounded tip at its distal end, and an slideably mounted outer coaxial tubular member. The rounded tip is shaped such that its proximal end, which is inserted into position in the distal end of the inner tubular member, presents essentially a "ramp" designed to aid ejection of the attenuation device from the fenestration when it is advanced. The attenuation device to be delivered is attached to its inflation tube, folded as previously described, and drawn into the inner sheath through the fenestration. Once situated within the fenestration the outer coaxial tubular member is slid forward to close the fenestration, thus containing the bladder within the inner tube.

With reference to the embodiment illustrated in FIG. 34A, delivery system 370 comprises an inner sheath 372, a slideable outer sheath 374, an opening 376 in the inner sheath, and an atraumatic tip 378. With reference to the embodiment illustrated in FIG. 34B, delivery system 370 comprises an outer sheath 374 that slides backwards and an attenuation device 380. Here, the attenuation device 380 is exposed through the opening 376. The delivery system 370 comprises an inflation tube 382 that is advanced toward the atraumatic tip 78, thereby causing the attenuation device 380 to be ejected. A curved ramp 384 in the delivery system 370 aids the ejection of the attenuation device 380.

In use the distal end of the delivery system is inserted through the urethra to an appropriate depth, the outer coaxial tube is slid backwards along the inner tube, thus exposing the fenestration in the inner tube. The attenuation device is advanced using the inflation tube and releases easily from the inner tube. The attenuation device is inflated, released from the inflation tube, and floats freely in the bladder.

In another embodiment, shown in FIGS. 35A and 35B, the attenuation device containment tube 386 is a simple open-ended cylinder. The attenuation device 380 is folded as described previously and withdrawn into the containment tube 386. The open end of the containment tube 386 would present a potentially traumatic edge to the urethra. In order to prevent such trauma, the open end of the containment tube 386 in this instance has rounded atraumatic end 378. This end 378 contains slits 388 which, on sliding the containment tube 386 backwards allows the end 378 to open, thus allowing deployment of the attenuation device 380 from the containment tube 386. On advancing the inflation tube 382 with the attenuation device 380 attached, the slits 388 open and present little barrier to the deployment of the attenuation device.

In another embodiment, the attenuation device is delivered percutaneously through the pelvis into the bladder. Similar to percutaneous access of arteries or veins, a needle is inserted through the skin and into the bladder. A guide wire is placed through the needle and the needle is removed leaving the guide wire in place. The delivery system and attenuation device are pushed into the bladder over the guide wire. The attenuation device is deployed and the delivery system and guide wire are removed. Guidance using ultrasound can also be employed to help guide the delivery system into the bladder.

In one embodiment, a removable delivery system is used to deliver, deploy, and fill the attenuation device. The delivery system can take the form of the system taught by U.S. Pat. No. 5,479,945, titled method and a removable device which can be used for the self-administered treatment of urinary tract infections or other disorders, issued Jan. 2, 1996, the disclosure of which is incorporated in its entirety herein by reference.

Figure 7A:
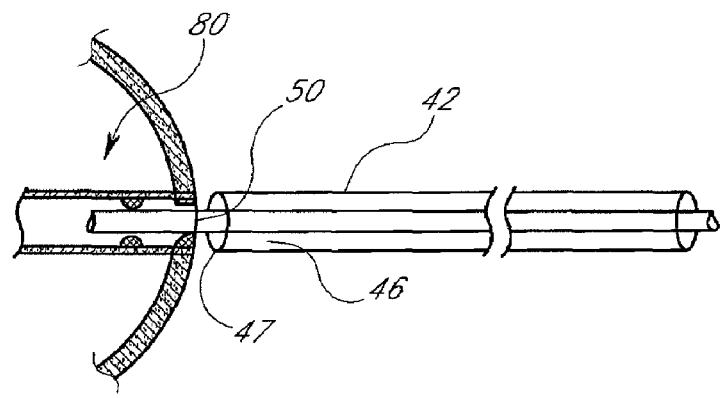
FIG. 7A is a fragmentary schematic view of the filling tube of a delivery system engaged within the valve of an attenuation device.
Figure 7B:
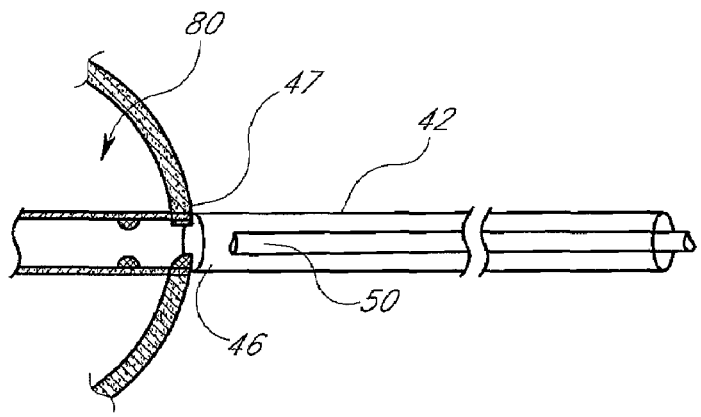
FIG. 7B is a fragmentary schematic view as in FIG. 7A, with the filling tube proximally retracted from the valve.
Figure 7C:
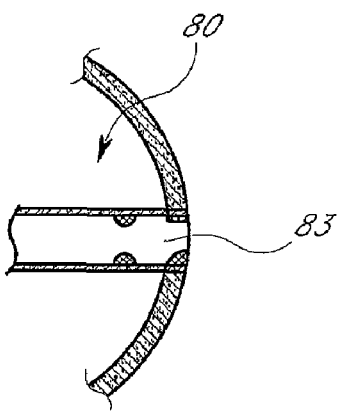
FIG. 7C illustrates details of a valve construction for an attenuation device.

With reference to FIGS. 7A and 7B, there is illustrated one disengagement sequence for deploying the inflatable attenuation device 66 from the delivery system 40 in accordance with one aspect of the present invention. As illustrated in FIG. 7A, the delivery system 40 is initially configured with the filling tube 50 positioned within the valve 80. The distal end 46 of outer tubular body 42 is dimensioned such that it will not fit through the aperture 82 of valve 80. Once the attenuation device 66 has been positioned within the bladder, the attenuation device 66 is inflated through filling tube 50.

With reference to FIG. 7B, the filling tube 50 is proximally retracted following inflation so that it disengages from the valve 80. This is accomplished by obstructing proximal movement of the attenuation device 66 by stop surface 47 on the distal end 46 of tubular body 42. The attenuation device 66 is thereafter fully disengaged from the delivery system 40, and the delivery system 40 may be removed.

Figure 8A:
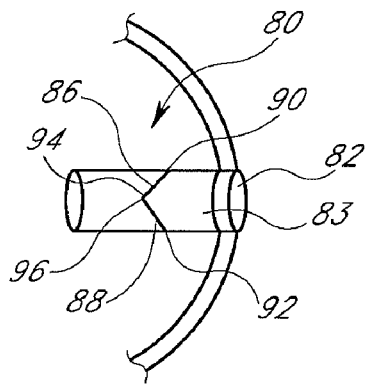
FIGS. 8A-8E schematically illustrate different valve constructions for an inflatable attenuation device in accordance with the present invention.
Figure 32A:
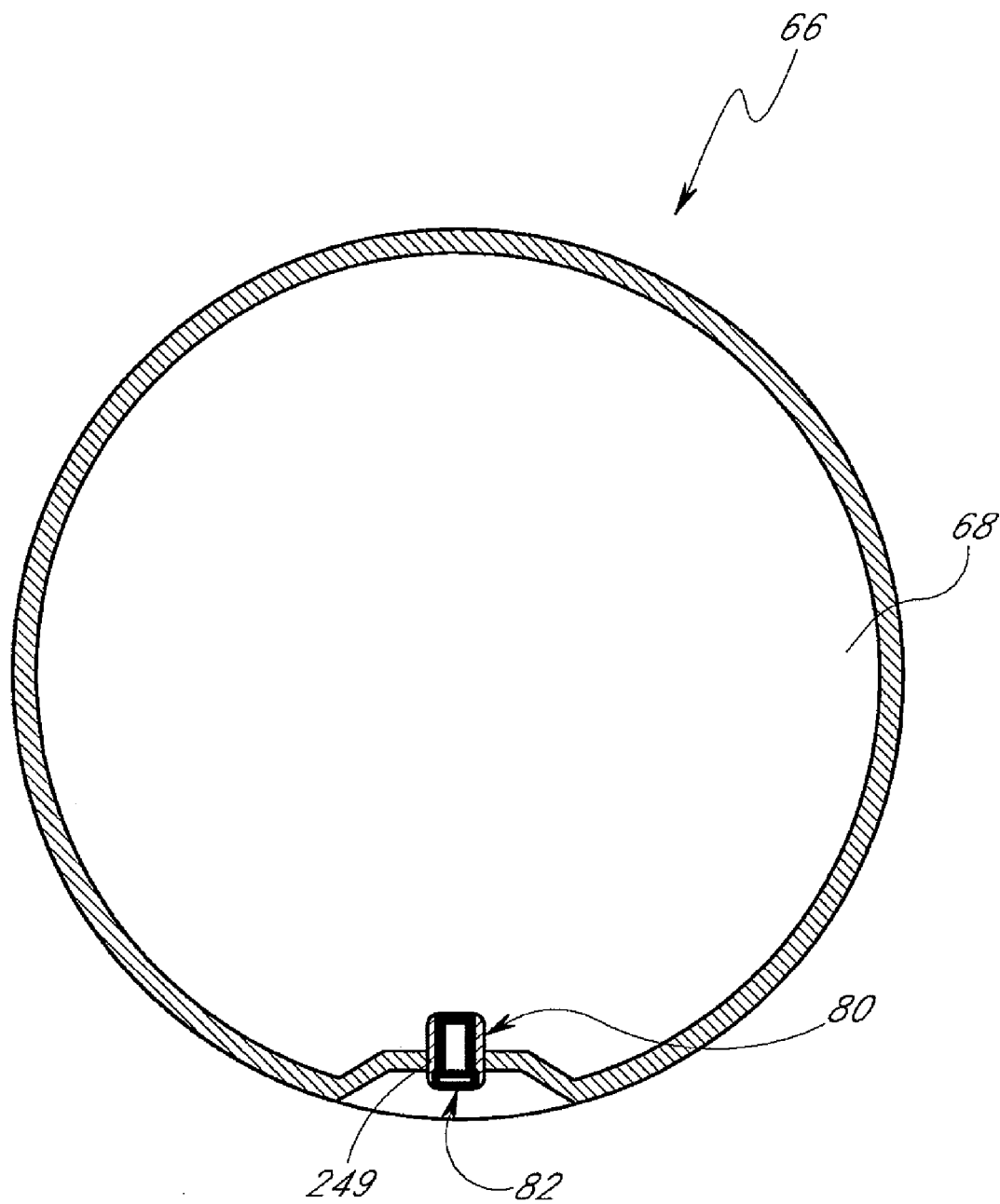
FIG. 32A is a schematic top plan view of an inflatable attenuation device with a duckbill valve design.

With reference to FIGS. 8A, 32A, and 32B, there is illustrated a duckbill embodiment of the valve 80. Valve 80 comprises a tubular wall 81, having an aperture 82 in communication with a flow path 83. At least one closure member 84 is attached to the tubular wall, and extends across the flow path 83. In the illustrated embodiment, closure member 84 comprises a first and a second duck bill valve leaflets 86 and 88 which are attached at lateral edges 90 and 92 to the tubular wall. The leaflets 86 and 88 incline medically in the distal direction to a pair of coaptive edges 94 and 96. This configuration allows forward flow through flow path 83 to separate coaptive edges 94 and 96, thereby enabling inflation of the attenuation device 66. Upon removal of the inflation media source, the inflation media within the attenuation device 66 in combination with natural bias of the leaflets 86 and 88 cause the leaflets to coapt, thereby preventing effluent flow of inflation media through the flow path 83.

The tubular body 81 and first and second leaflets 86 and 88 may be manufactured from any of a variety of materials which will be apparent to those of skill in the art. For example, tubular body 81 may be made from polyurethane such as by extrusion. Leaflets 86 and 88 may be made from any of a variety of flexible materials such as polyurethane, silicone, or polyethylene, and may be bonded to the tubular element 81 using adhesives, heat bonding, or other bonding techniques known in the art. Suitable valves include the valve manufactured by Target Therapeutics and sold as the DSB silicon balloon to fill aneurysms and arterial-venous malformations.

With continued reference to FIGS. 8A, 32A, and 32B, in one method of manufacturing the attenuation device 66, the bushing 249 is RF welded to the inflatable container 68 prior to installing the valve 80. Here, the duckbill valve 80 is bonded to the bushing 249 after welding. In one method of manufacturing the attenuation device 66, the mandrel is installed during welding, resulting in a polished surface with an air-tight seal along the inside of the tube.

Figure 8B:
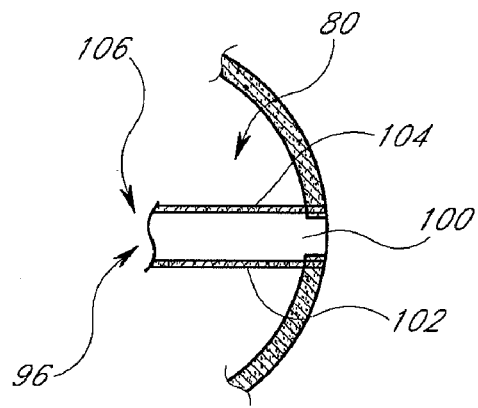

Referring to FIG. 8B, closure is accomplished by two coaptive edges on distal end 106 of tubular body 81. This construction is sometimes referred to as a flapper valve. The tubular body 81 in this embodiment is formed by a first wall 96 and a second wall 100 which are bonded or folded along a first edge 102 and a second edge 104 to define a flow path 83 extending therethrough. The free distal ends of first and second walls 96 and 100 at the distal end 106 form coaptive leaflets, which may be opened under forward flow pressure through the flow path 83 and will inhibit or prevent reverse flow through the flow path 83.

Figure 8C:
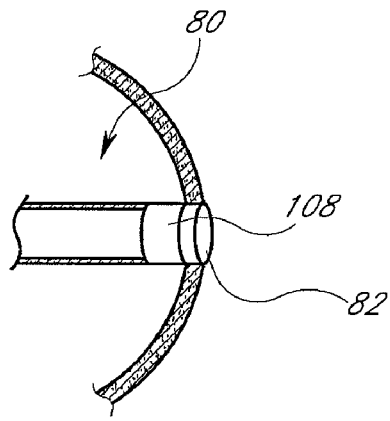

Referring to FIG. 8C, the proximal end of the flow path 83 on the flapper valve of FIG. 8B or other valve structure may be reinforced such as by a reinforcing tube 108. Reinforcing tube 108 may be manufactured in any of a variety of ways. For example, reinforcing tube 108 may be extruded from various densities of polyethylene, Pebax, polyurethane, or other materials known in the art. Reinforcing tube 108 may be desired to maintain patency of the pathway to the valve 80, particularly in an embodiment adapted for coupling to a deflation and removal system as will be discussed. In another embodiment, the reinforcing tube 108 may be removable and used to prevent sealing of the valve during the manufacturing process and may also ease the placement of a fill tube in the valve. This reinforcing tube 108 is removed after the manufacturing process is complete, or may be removed before, during, or after the fill tube is placed.

Figure 8D:
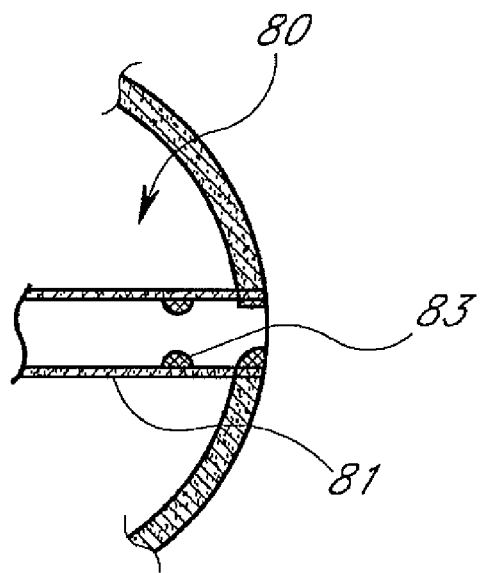
Figure 33A:
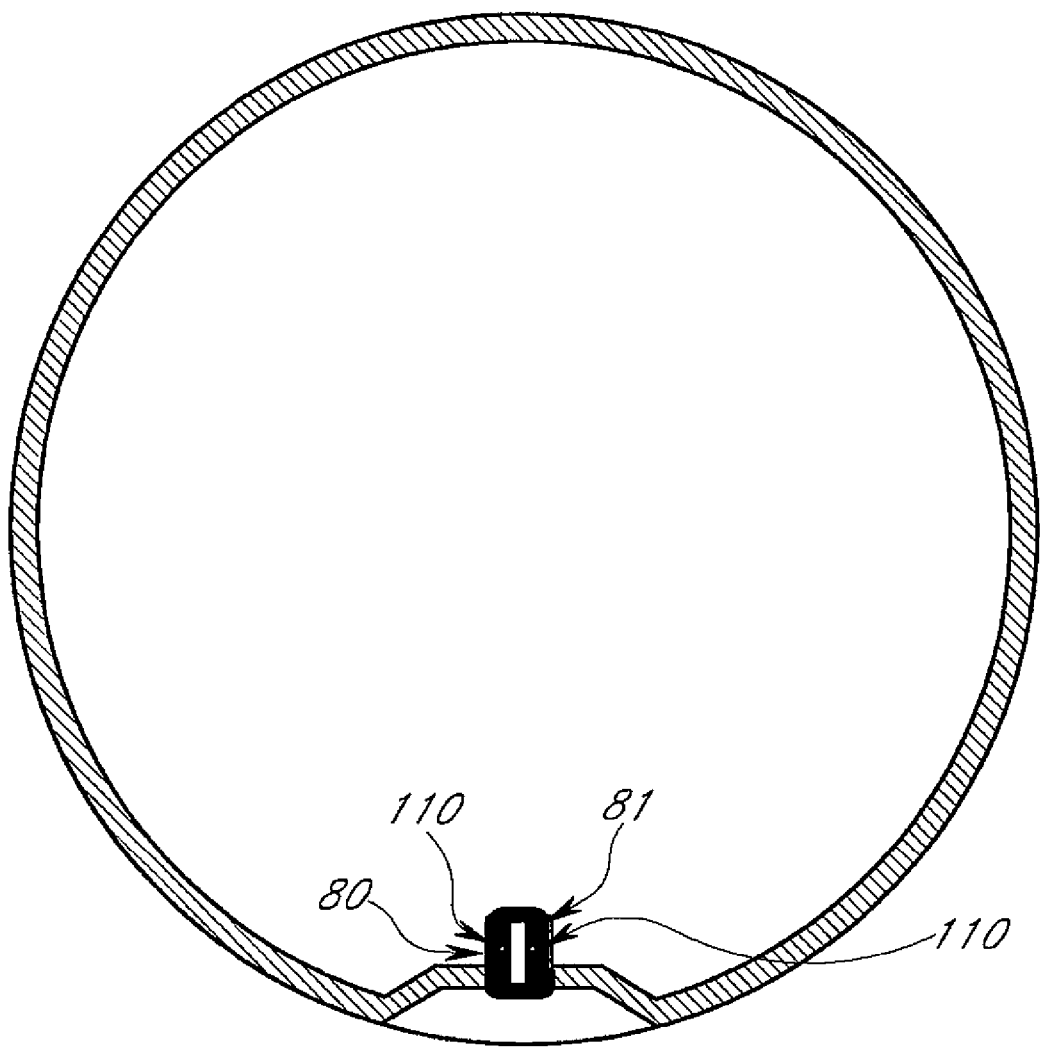
FIG. 33A is a schematic top plan view of an inflatable attenuation device with a ring valve design.

With reference to FIGS. 8D and 33A, there is illustrated an additional feature that may additionally be incorporated into any of the valves discussed above. In one embodiment of the this feature, an annular sealing ring 110 is provided on the interior surface of the tubular body 81. Annular sealing ring 110 is adapted to provide a seal with the filling tube 50, to optimize the filling performance of the attenuation device. Sealing ring 110 is thus preferably formed from a resilient material such as silicone or polyurethane and dimensioned to slideably receive the filling tube 50 therethrough. In another embodiment, sealing with the fill tube may be enhanced by restricting the aperture diameter without the use of a distinct sealing ring 110. Exemplary dimensions of the attenuation device 66 are shown in FIG. 33A.

Figure 8E:
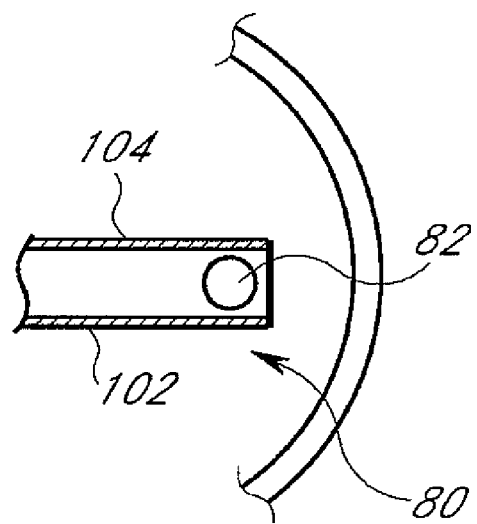
Figure 9:
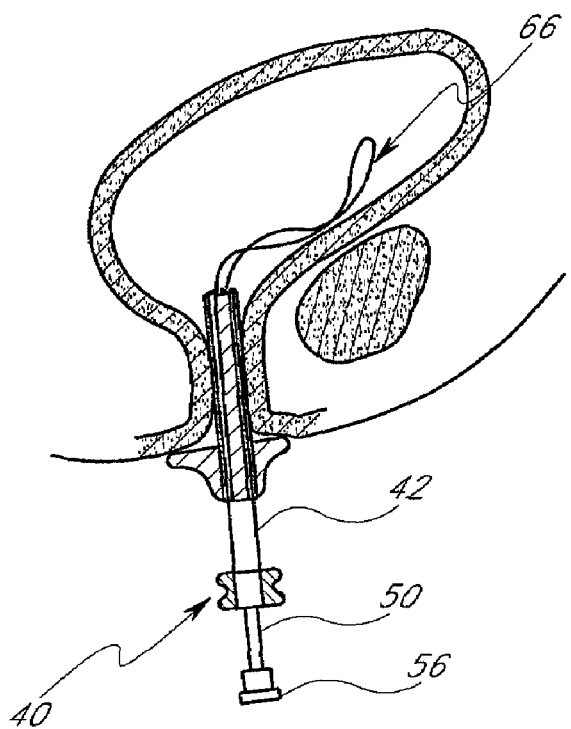
FIG. 9 is a schematic representation of the delivery system of FIG. 6, transurethrally positioned within the bladder.
Figure 10:
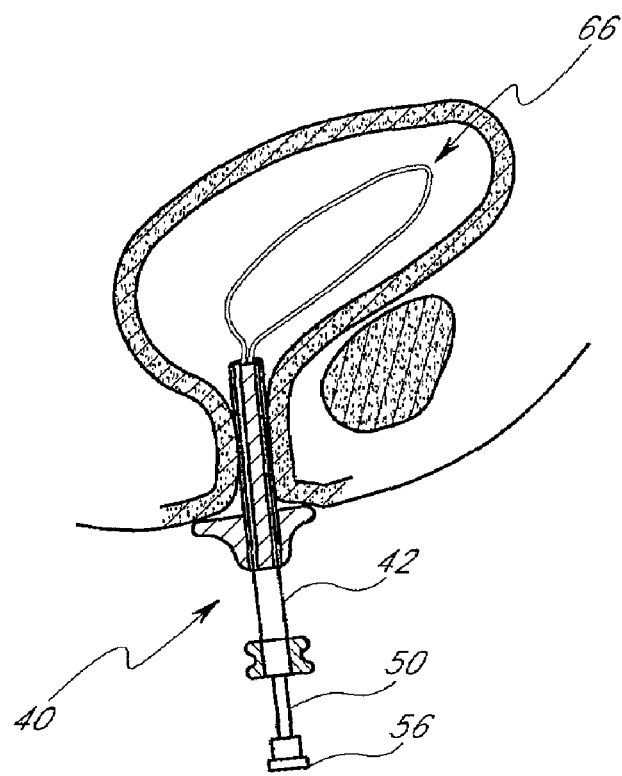
Figure 11:
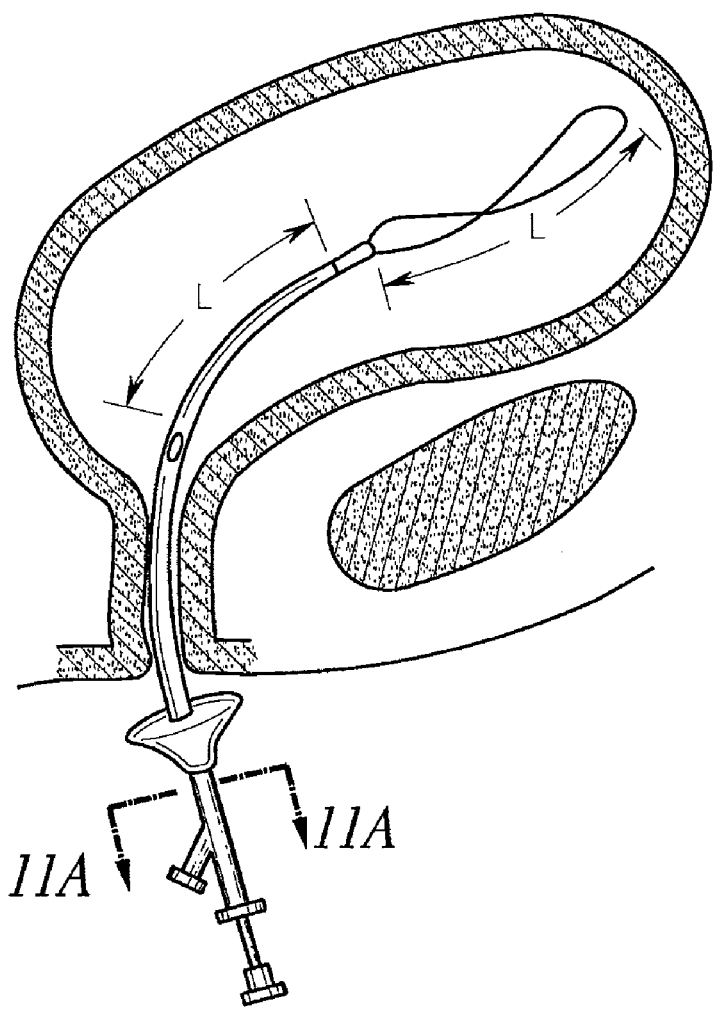
FIG. 11 is a schematic view of one embodiment of a delivery system in accordance with the present invention, transurethrally positioned within the bladder.
Figure 11A:
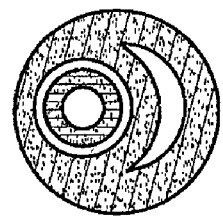
FIG. 11A is a cross-section through one embodiment of the delivery system of FIG. 11.
Figure 33B:
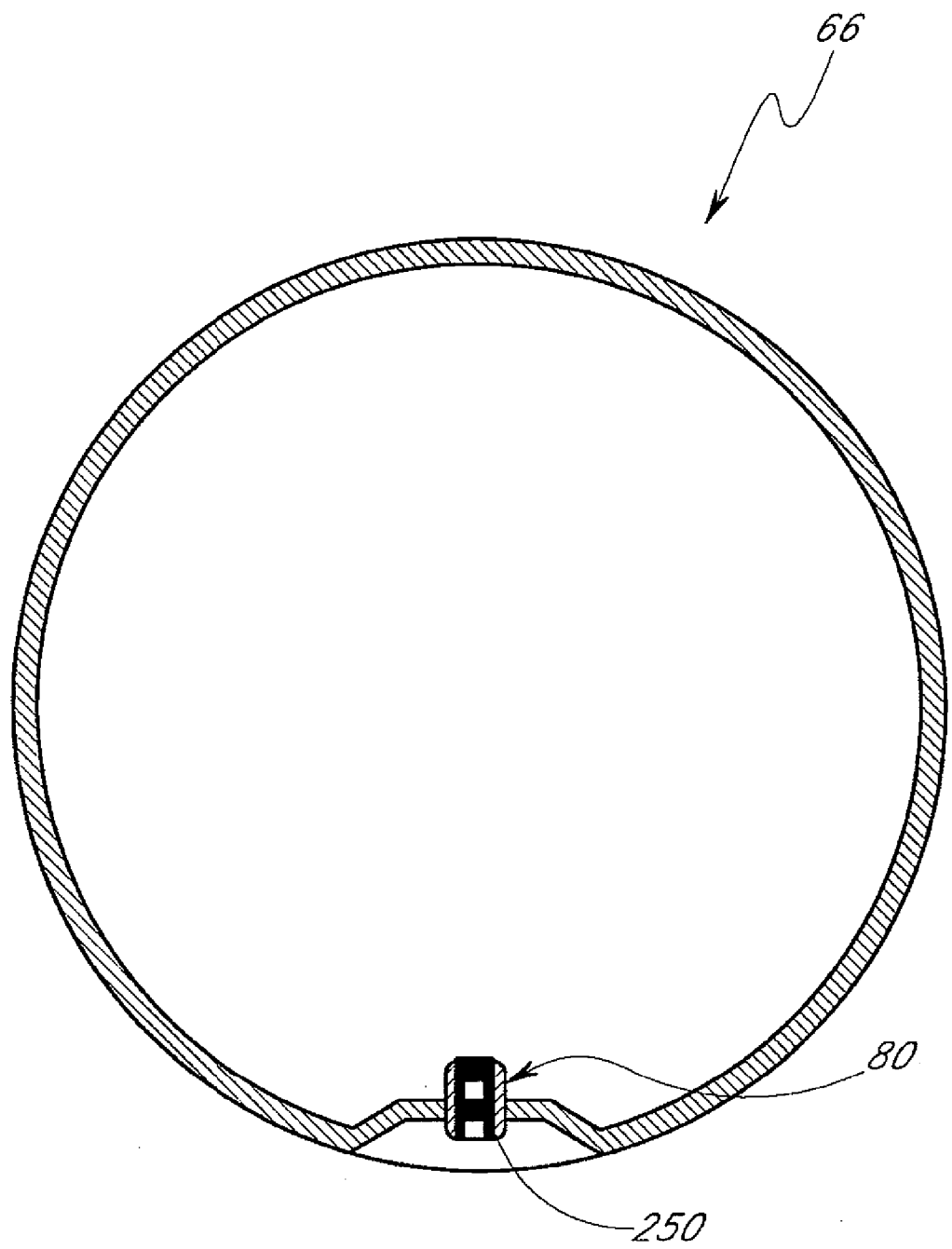
FIG. 33B is a schematic top plan view of an inflatable attenuation device with a fill/plug design.
Figure 33C:
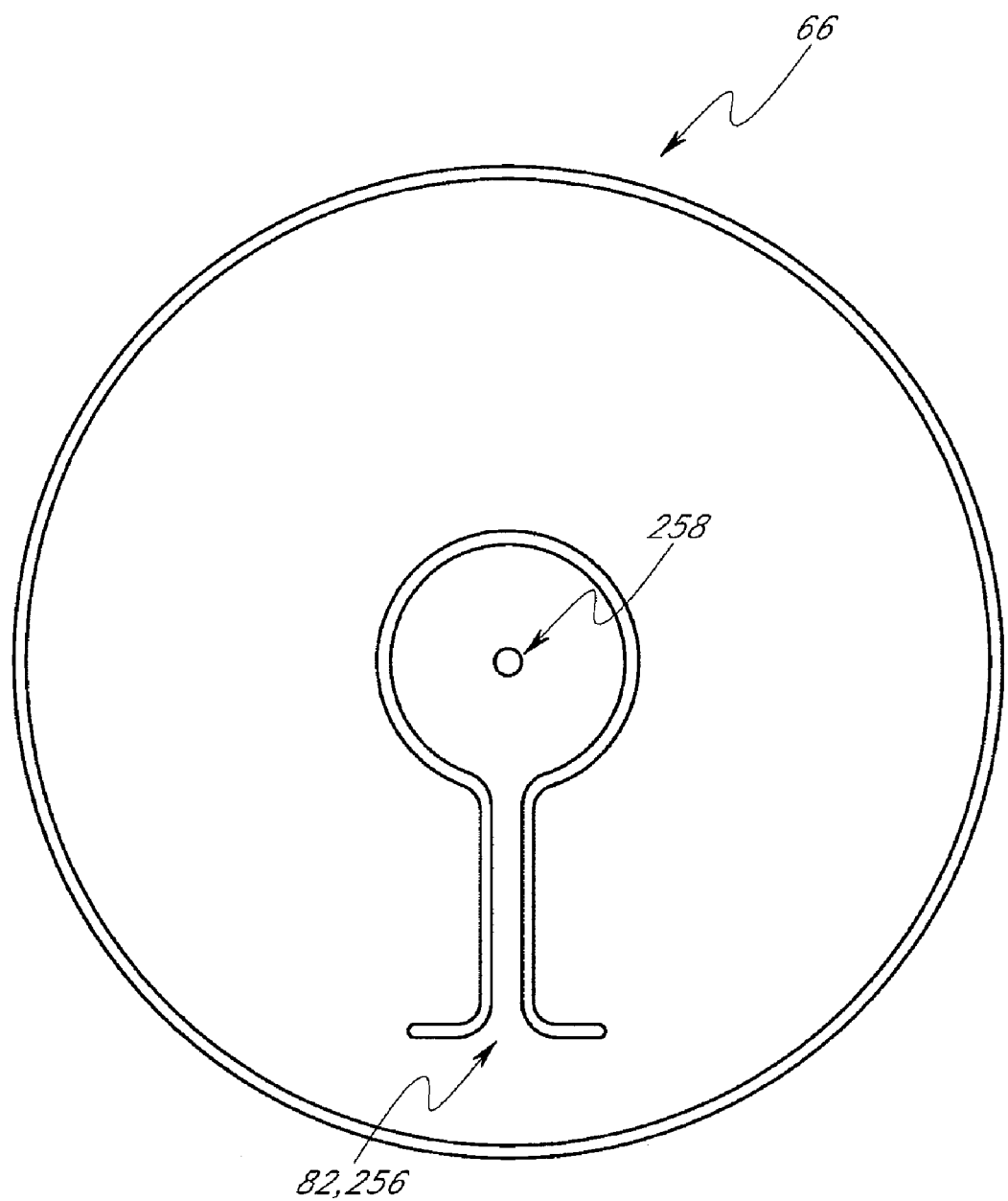
FIG. 33C is a schematic top plan view of an inflatable attenuation device with a dome valve design.

With reference to FIGS. 8E and 33C, the valve may also be placed in the body of the attenuation device, rather than in the seam. In one exemplary embodiment, the through hole 258 has a diameter of 0.062 inches. Here, the inflation channel 256 has a diameter of approximately 0.063 to 0.070 inches. The valve can be placed in any number of ways including the methods described in U.S. Pat. No. 5,248,275, titled Balloon with flat film valve and method of manufacture, issued Sep. 28, 1993, and U.S. Pat. No. 5,830,780, titled Self-closing valve structure, issued Nov. 3, 1998; both of these patents are hereby incorporated by reference herein and made a part of this specification.

In one embodiment, shown in FIG. 33B, the valve 80 has a fill/plug 250. In one method of manufacturing the fill/plug attenuation device 66, the mandrel is installed during welding, resulting in a polished surface with an air-tight seal along the inside of the tube.

The attenuation device 66 is preferably also removable from the bladder. Removel may be accomplished in any of a variety of ways, depending upon the construction of the attenuation device. Preferably, removal is accomplished transurethrally. In one embodiment, removal is accomplished by reducing the attenuation device 66 from its second enlarged profile to its first, reduced profile so that it may be withdrawn transurethrally by a removal system. The removal system will be configured differently depending upon whether reduction from the second profile to the first profile is accomplished by deflation, or by compression. One embodiment of a removal system utilized to remove an inflatable attenuation device 66 will be described below in connection with FIG. 12.

In another embodiment, the removal procedure involves dissolving or degrading the material or a portion of the material of the attenuation device 66 in situ. Material selection and wall thickness of the attenuation device 66 may be optimized to provide the desired useful life of the attenuation device 66, followed by dissolution in the aqueous environment of the bladder. In one embodiment, dissolution or deflation may be catalyzed or accelerated by an accelerating event such as a change in pH or introduction of an initiator or accelerator into the bladder, or reduction of pressure.

Attenuation devices having a predetermined dwell time after which they are automatically voided advantageously eliminate the need for a removal procedure. Such temporary attenuation devices can be manufactured in a variety of ways in accordance with the present invention, such as through the use of bioabsorbable or permeable materials. In one embodiment, the entire wall of the inflatable container 68 is made from an absorbable material. As used herein "absorbable" means any material which will dissolve, degrade, absorb or otherwise dissipate, regardless of the chemical mechanism, to achieve the purpose recited herein. In another embodiment, only a portion of the flexible wall 70 or other portion of the attenuation device such as the valve is made from an absorbable material. As soon as one or more windows or "fuse" components of the attenuation device is absorbed, the attenuation device will deflate through the resulting opening and can be expelled during normal voiding. In yet another embodiment, one or more seams such as seam 78 can be bonded by a dissolvable or absorbable material that is designed to fail after a predetermined time in the aqueous environment of the bladder.

The resulting deflated components from any of the foregoing time limited embodiments can thereafter either be expelled during normal voiding, or can remain in the bladder in a deflated state until removed using a removal system. In one embodiment, the material or portion of the inflatable container 68 is made from a gas permeable material. As the gas dissipates from the inflatable container, its ability to spontaneously void increases. In one embodiment, the attenuation device is filled with approximately 20 ml of gas and the attenuation device's material allows approximately 15 ml of gas to permeate out of the attenuation device over certain time intervals, such as, for example, one, three, six, or twelve months. Once the volume remaining is less than approximately 5 ml, the attenuation device is normally voided.

The predetermined dwell time within the bladder can be influenced by a variety of design factors, including the formulation of the absorbable material and the physical shape, thickness and surface area of the absorbable component. A variety of absorbable polymers which can be used in the present invention are known in the absorbable suture arts. For example, absorbable multifilament sutures such as DEXON sutures (made from glycolide homopolymer and commercially available from Davis & Geck, Danbury, Conn.), VICRYL sutures (made from a copolymer of glycolide and lactide and commercially available from Ethicon, Inc., Sommerville, N.J., and POLYSORB sutures (also made from a copolymer of glycolide and lactide and commercially available from United States Surgical Corporation, Norwalk, Conn.) exemplify materials known in the industry and characterized as short term absorbable sutures. The classification short term absorbable sutures generally refers to surgical sutures which retain at least about 20% of their original strength at three weeks after implantation, with the suture mass being essentially absorbed in the body within about 60 to 90 days post implantation.

Certain bioabsorbable elastomers may also be used to form the attenuation devices or fuses in accordance with the present invention. The elastomers can be melt-processed, for example by extrusion to prepare sheets, plugs or tubular structures. In one embodiment, the copolymers can be injection molded to fabricate intricately designed parts, or compression molded to prepare films. For the details of such melt-processing techniques, see, for example, F. Rodriguez, Principles of Polymer Systems, Chapter 12 (McGraw Hill 1970).

The bioabsorbable elastomers can also be solvent cast to prepare thin films. Solvent casting can be accomplished using conventional methods such as first dissolving the copolymer in a suitable solvent to make a solution, then casting the solution on a glass plate to make a film, and then evaporating the solvent from the cast film. In another processing scheme, the copolymers can be lyophilized to prepare foams. Lyophilization can be accomplished by first dissolving the copolymer in an appropriate solvent, freezing the solution, and then removing the solvent under vacuum. The set of appropriate solvents include p-dioxane. Lyophilization techniques to prepare films are described in Louis Rey, Aspects Theoriques Et Industriels De La Lyophilization (1964).

Certain bioabsorbable elastomers are disclosed in U.S. Pat. No. 6,113,624, titled Absorbable elastomeric polymer, issued Sep. 5, 2000, the disclosure of which is incorporated in its entirety herein by reference. In accordance with the process disclosed therein, a two-step, one-reaction vessel, two-temperature process is utilized in which a mixture of p-dioxanone monomer and p-dioxanone homopolymer, is formed at low temperatures of from about 100° C. to about 130° C., preferably 110° C. The mixture is then reacted with lactide at temperatures from about 120° C. to about 190° C. to form copolymers in which segments or sequences are composed of both p-dioxanone and lactide repeating units. These segmented copolymers are stated to be less crystalline than the block or graft copolymers previously known in the art and, therefore, yield materials with good strength, but shorter BSR ("Breaking Strength Retention") profiles, faster absorption rates, much longer elongations and lower stiffness than the block copolymers. A wide variety of copolymers of polylactic and polyglycolic acids are also known in the art, particularly for use with absorbable orthopedic screws and fasteners.

The ideal material can be optimized through routine experimentation taking into account the attenuation device design and the desired indwelling time period. Attenuation devices may be time rated, such as 15 days, 30 days, 45 days, 90 days, 180 days or other as may be desired. The deflated and or partially dissolved attenuation device will be transurethrally expelled within a few days of the expiration of the rated time period from the time of implantation.

Figure 12:
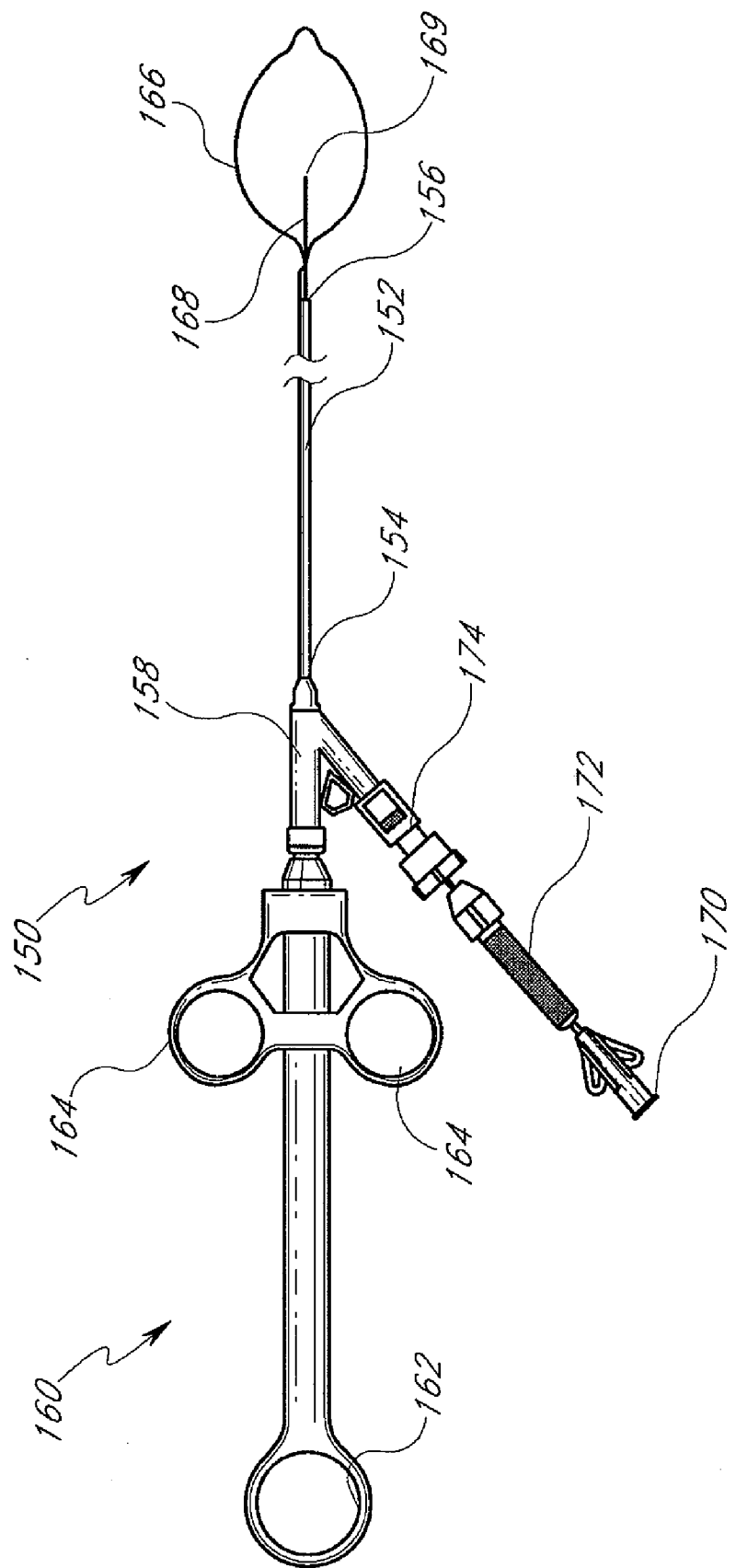
FIG. 12 is a side elevational. schematic view of an attenuation device removal system in accordance with one aspect of the present invention.

Referring to FIG. 12, there is illustrated a side elevational schematic view of one embodiment of an intravesical removal system in accordance with the present invention. This removal system is adapted to retrieve the inflatable attenuation device discussed elsewhere herein. The removal system 150 comprises an elongate tubular body 152 which extends between a proximal end 154 and a distal end 156. Tubular body 152 is dimensioned to transurethrally access the bladder. In one embodiment, the removal system 150 is adapted for use in conjunction with standard urological cystoscopes (e.g. approximately 14-24 French), having minimum working channels of approximately 1.8 to 6.0 mm. For this purpose, removal system 150 in one embodiment has an overall length of approximately 76 cm and a useable length of approximately 60 cm.

The tubular body 152 may be manufactured in accordance with any of a variety of techniques well understood in the catheter and other medical device manufacturing arts. In one embodiment, tubular body 152 is extruded from a biocompatible material such as '114E, having an inside diameter of approximately 0.09 inches and a wall thickness of about 0.01 inches.

The proximal end 154 of tubular body 152 is connected to a Y-adaptor 158. Y-adaptor 158 carries a control 160 for controlling the retrieval system as will be described. Control 160 in the illustrated embodiment comprises a thumb ring 162 which is slideably carried with respect to a pair of finger rings 164. Axial movement of the thumb ring 162 with respect to the finger rings 164 enlarges or retracts a retrieval loop 166 extending distally from distal end 156 of tubular body 152. Retrieval loop 166 is adapted to surround the inflated attenuation device 66. In one embodiment, the loop 166 has an enlarged diameter of about 27 mm, and comprises a wire such as 0.016 inch diameter stainless steel cable wire.

In use, the loop 166 is opened once the distal end 156 of the tubular body 152 has reached the bladder. The loop 166 is positioned around the attenuation device 66, and the proximal control 160 is manipulated to tighten the loop 166 around the attenuation device 66. After the attenuation device 66 has been securely grasped by the loop 166, a deflating tube 168, preferably having a sharpened distal tip 169 thereon, is distally advanced through the wall of the attenuation device 66. Distal advancement of the deflating tube 168 may be accomplished by distally advancing a proximal control, such as control 172. The distal tip 169 is in fluid communication with a connector such as a standard luer adaptor 170 through a central lumen (not illustrated), so that an empty syringe or other device may be connected to the connector 170 and used to evacuate the contents of the ensnared attenuation device 66. As the attenuation device 66 is deflated, the control 160 may be manipulated to pull the collapsed attenuation device 66 into the distal end 156 of the tubular body 152. The removal system 150 having the reduced attenuation device 66 therein or carried thereby may be transurethrally removed from the patient.

Figure 21:
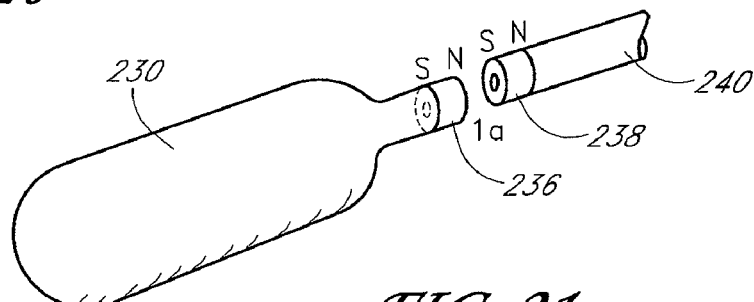
FIG. 21 is a schematic perspective view of the attenuation device of FIG. 20, aligned with the distal end of a delivery or removal system.

A wide variety of modifications can be made to the foregoing removal system 150, within the spirit of the present invention. For example, the proximal controls 160 and 172 may be combined into a pistol grip or other configuration. Controller 172 or control 160 may additionally control deflection of the distal end 156 of the tubular body 152, or control rotation of the plane of the loop 166. In general, the removal system 150 preferably accomplishes the basic functions of enabling the location of the attenuation device 66, capturing the attenuation device, reducing the attenuation device in size and removing the attenuation device from the bladder. The capturing step may be accomplished by visualizing the attenuation device through the urological cystoscope, or by "blind" techniques, such as, for example, light reflectance, impedance, suction, ultrasound, passive induced microchip, or the magnetic locator described in connection with FIGS. 21, 22, 23, below.

Figure 13:
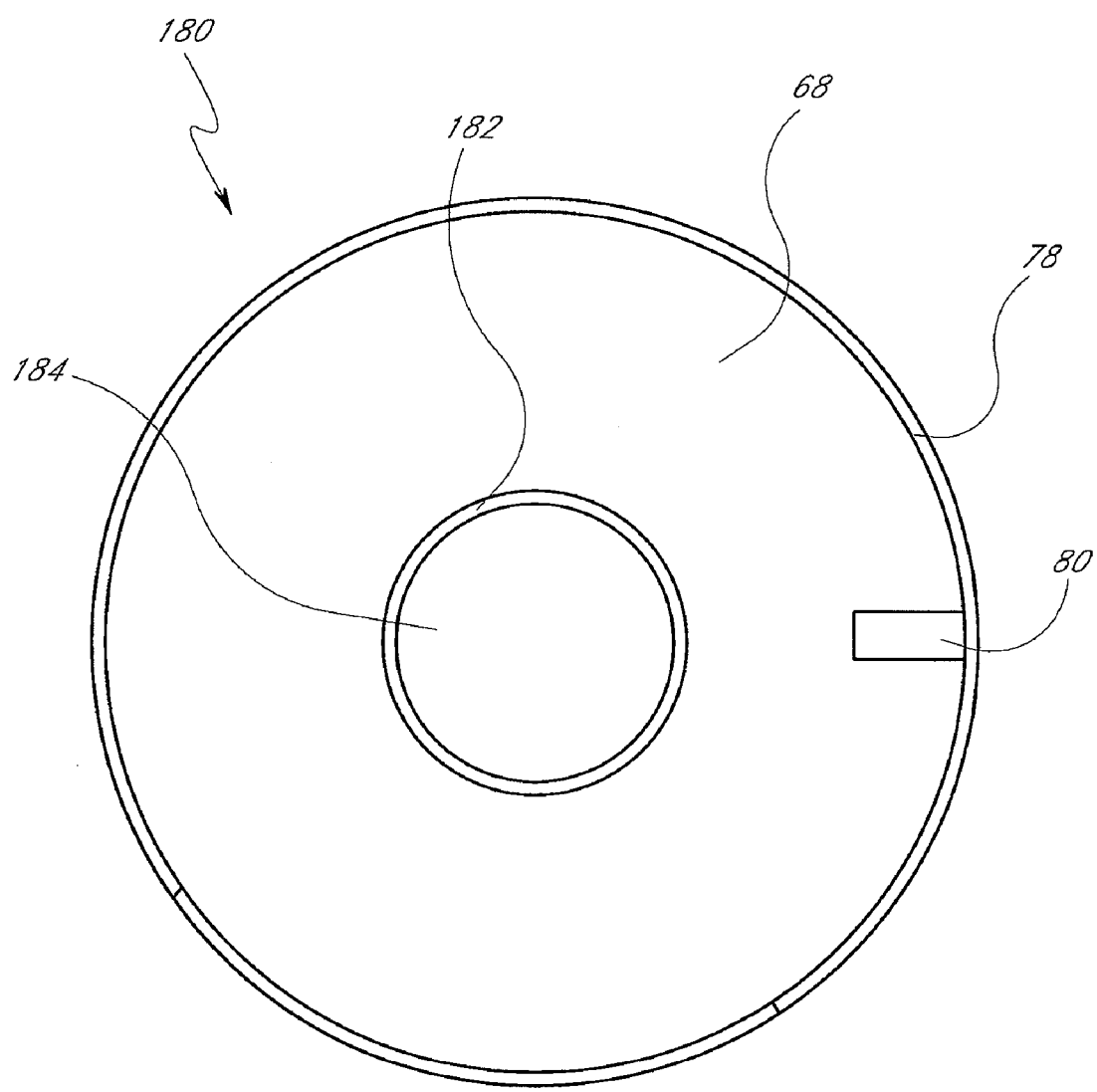
FIG. 13 is a schematic view of a toroidal shaped attenuation device accordance with one embodiment of the present invention.
Figure 13A:
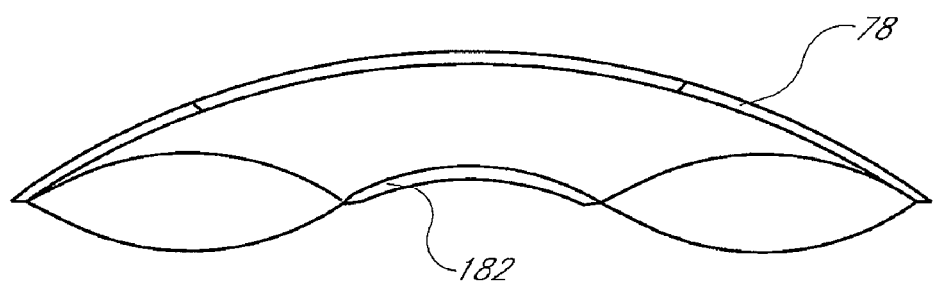
FIG. 13A is a side elevational cross-section view through one embodiment of the attenuation device of FIG. 13.

Referring to FIGS. 13 and 13A, there is illustrated a top plan view of one embodiment of an attenuation device 180 in accordance with one aspect of the present invention. The attenuation device 180 comprises an inflatable body 68 generally as has been described. An outer seam 78 may be provided with a valve 80. In this embodiment, an inner seam 182 defines a central region 184. The outer seam 78 and inner seam 182 define a generally torodial-shaped inflatable container 68. The central region 184 may comprise either a membrane or a central opening, depending upon the desired performance characteristics. The center hole may assist in the placement and location of the attenuation device within the bladder, permit additional baffling of the pressure waves within the bladder, minimize the attachment to the bladder wall by surface tension between the attenuation device and the bladder wall, and allow for urine flow through the hole in the event that the attenuation device is in or near the bladder neck.

Figure 14:
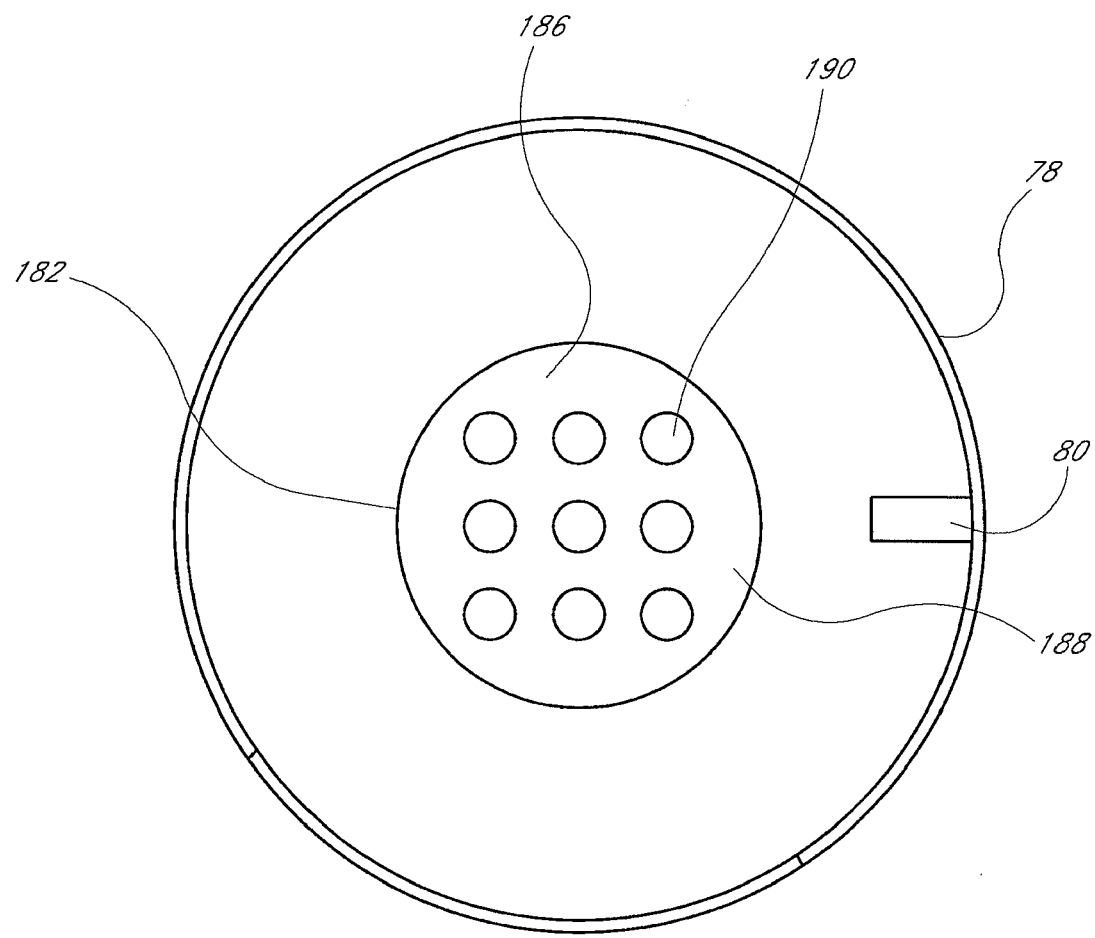
FIG. 14 is a schematic view of a toroidal shaped attenuation device as in FIG. 13, with an integral baffle therein.
Figure 14A:
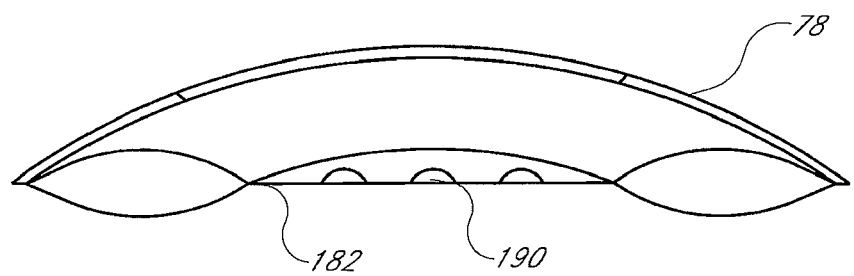
FIG. 14A is a side elevational cross-section view through one embodiment of the attenuation device of FIG. 14.

In one embodiment, illustrated in FIGS. 14 and 14A, the central region 184 comprises a baffle 186. The baffle 186 comprises a membrane 188 having a plurality of apertures 190 therein. In the illustrated embodiment, approximately nine round apertures 190 are provided, each having a diameter of about 0.2 inches. Generally at least about 9 apertures 190 are provided, and many embodiments include anywhere from about 1 to about 1000 apertures. The optimal number of apertures 190 and sum of the area of the apertures 190 compared to the total area of the baffle 186 may be optimized depending upon the desired performance characteristics. Apertures may have any of a variety of configurations, such as round holes, irregular openings, slits or others.

Figure 15:
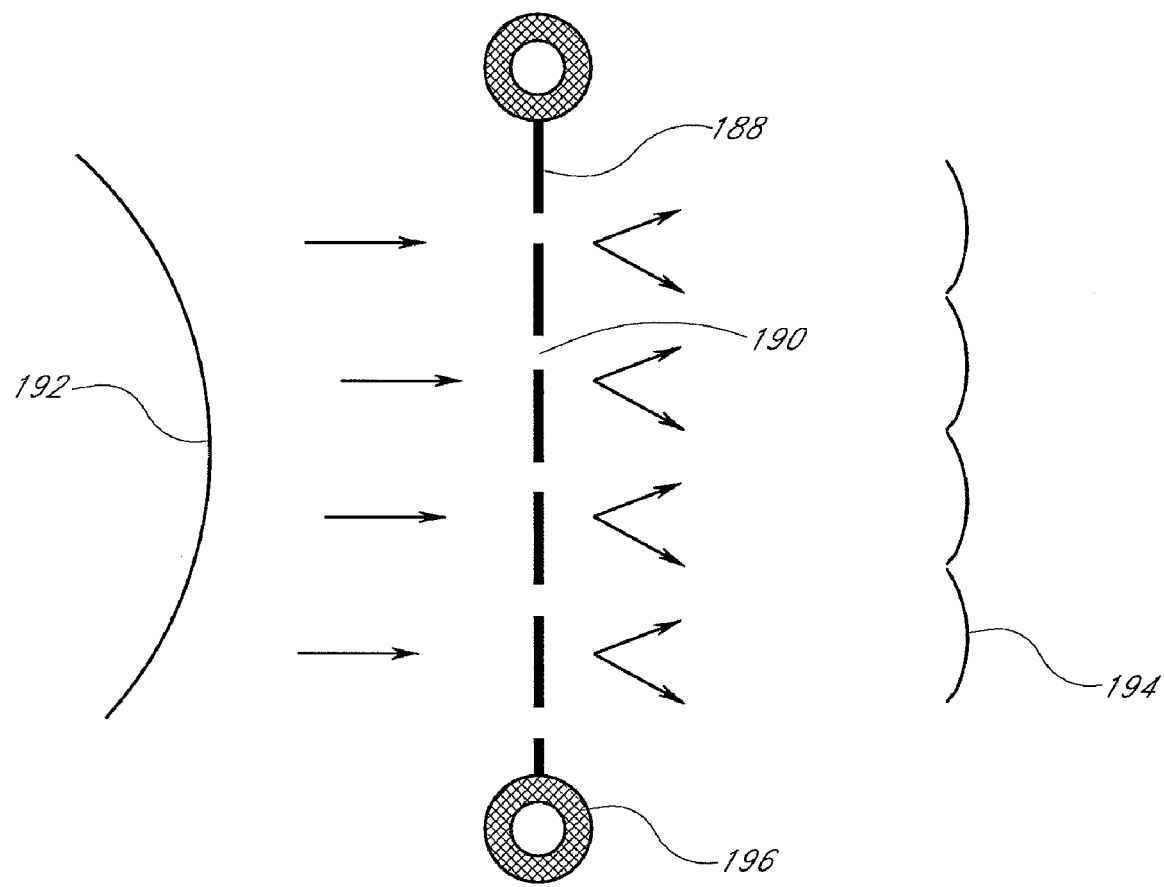
FIG. 15 is a schematic illustration of the attenuation device disrupting the unitary progression of a pressure wavefront.

The wave diffuser function of the baffle 186 is schematically illustrated in FIG. 15. A wave front 192 may be generated by any of a wide variety of events, such as coughing, sneezing, laughing, physical movement, muscle spasms or others as is understood. Since urine comprises essentially non-compressible water, and due to the low dynamic compliance of the bladder the wave front 192 will propagate rapidly through the bladder to impact structures such as the trigone area and the urethra. Apparent transient pressure spikes as high as 80 cm H2O or greater can be experienced during normal activities. In addition to reducing the pressure caused by pressure events such as coughing, the attenuation devices discussed above can also provide a baffle that distributes the wave across the bladder distributing and reducing the focused wave front that contacts the bladder neck.

If the attenuation device 180, having a baffle 186 is positioned within the bladder, the baffle 186 functions to disrupt the unitary progression of the wavefront 192. The prediffusion wave front 192 is thus interrupted into a plurality of post-diffusion wave fronts 194 by the baffle 186. Although the sum of the resulting post-diffusion wave fronts 194 is essentially equal to the prediffusion wave front 192, the greater dispersion of force accomplished by the baffle 186 is believed by the inventors to reduce the apparent magnitude of the wave front 192 as experienced by target tissue within the bladder.

As will be apparent in view of the foregoing, the baffle 186 may be constructed in any of a variety of manners and still accomplish the intended result. Thus, although the attenuation device 180 illustrated in FIGS. 13 and 14 comprises a generally toroidal-shaped inflatable container, any of a variety of other support structures may be utilized to maintain the baffle 186 in a useable configuration. The support 196 can comprise an inflatable tube, a resilient material such as nitinol wire, or other support structure as may be desired.

Certain embodiments of the present invention include a device that is mechanically in contact with the mucosal surface or tissue of the bladder or urethra. The sensation caused by the mechanical contact causes nerve receptors to tighten the urethral muscles increasing urethral resistance, thus, reducing or eliminating incontinence events.

Figure 16:
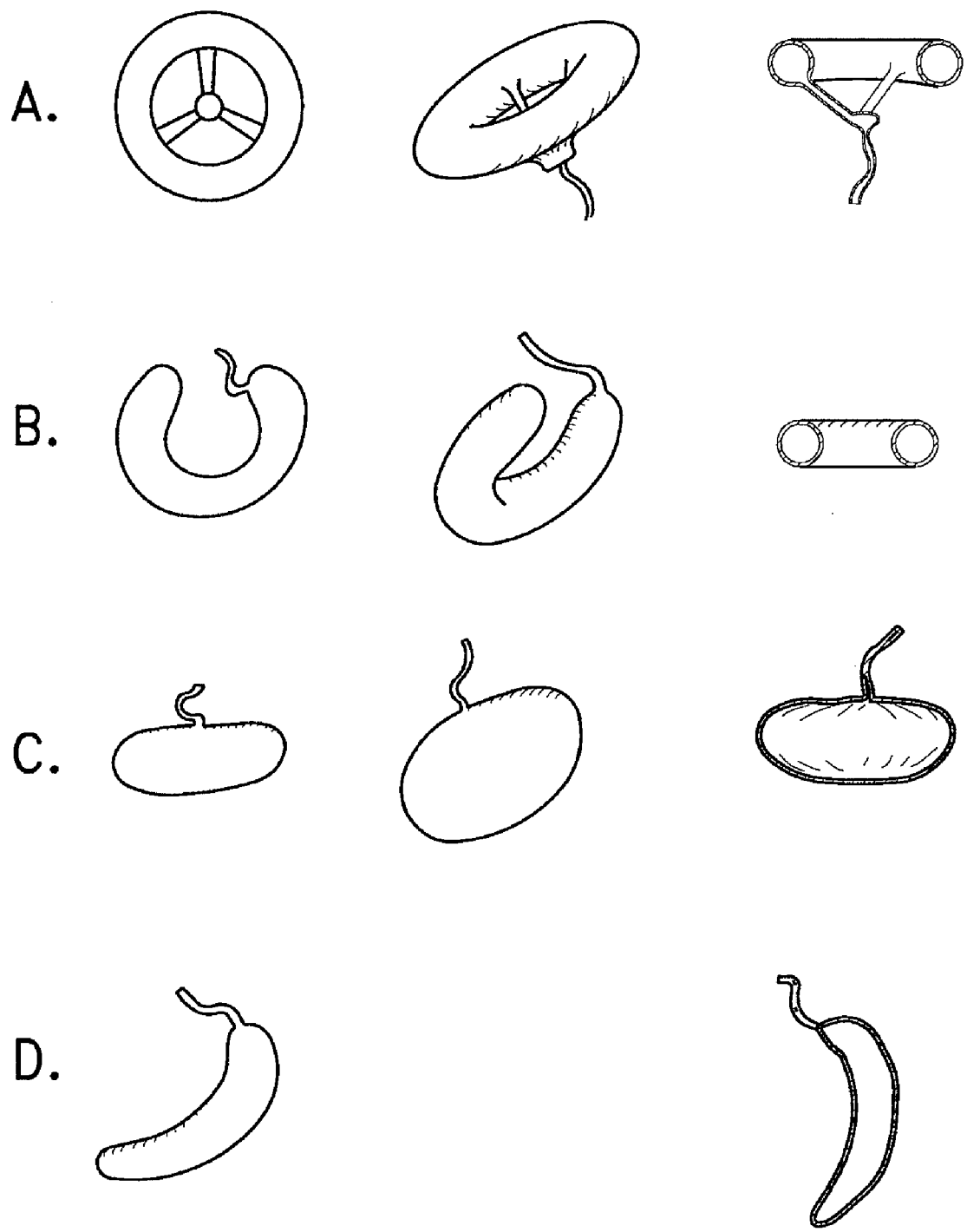
FIGS. 16A-D are schematic representations of a variety of inflatable attenuation devices in accordance with the present invention.

Referring to FIG. 16, there is illustrated a variety of shapes for the attenuation device 66, of the inflatable container variety. The devices used in embodiments of the present invention may take many shapes. In some instances it may be desirable for manufacturing purposes to have the shape resemble dip-molded devices like condoms, surgical glove fingers, or children's toys. However, many other forms may provide better performance, in particular for providing baffling of pressure waves as well as attenuation of pressure spikes. Possible shapes for the attenuation devices include torroid like shapes, similar in form but not size to donuts and inner tubes; spoked wheel forms; horseshoe-like forms; mushroom-like forms; and banana-like forms.

The attenuation devices of the present invention can be dip molded or extruded in a plurality of biocompatible materials. Furthermore, the attenuation devices can be fabricated from a variety of multi-layer composites or produced by a number of different manufacturing processes. Here, the designs of the attenuation devices are characterized by minimization and control of the gas and moisture vapor permeabilities in and out of the attenuation device.

The gas and moisture vapor permeabilities of any given material will vary depending on the conditions surrounding the material. For example, an attenuation device comprised of a certain material can have different gas and/or moisture permeabilities within the bladder than at standard temperature and pressure. In addition to exposure to urine, the intravesical environment includes exposure to pressure variations in the range of from about 0.05 psi to about 0.25 psi at rest, with transient pressure spikes as high as 2 psi or more. The body temperature is normally about 98 degrees F. or greater, and the attenuation device resides in 100% humidity. Long term efficacy of the attenuation device may be compromised if there exists any fluid or vapor exchange through the wall of the attenuation device in situ. The relative impermeability of the wall under normal intravesical conditions is preferably accomplished without losing the compliancy of the attenuation device which allows it to compress within folds of the bladder as is described elsewhere herein.

In general, the wall of the attenuation device will comprise at least one gas barrier layer and at least one moisture barrier layer. Any of a variety of gas barrier materials (e.g. polyvinylidene chloride, ethyl vinyl alcohol, fluoropolymers, etc.), available in thin film constructions, may be implemented into the attenuation device design. These materials are generally relatively stiff, have a high moisture vapor permeability, and have low impact strength. Consequently, layering the film with flexible, high moisture barrier, high impact strength polymers is desirable.

A variety of relatively flexible materials, having high moisture barrier characteristic and optionally high impact strength that can be formed into thin film sheets include but are not limited to: polyamide, polyethylene, polypropylene, polyurethane, polyamide/polyester copolymer, polystyrene/polybutadiene copolymer, etc. In one embodiment, at least one layer on, or the entire attenuation device comprises a blend of a barrier material and a flexible high impact strength material (e.g. polyurethane/polyvinylidene chloride, polyethylene/ethyl vinyl alcohol, etc.).

The attenuation device typically has two or more layers or barriers. For example, the attenuation device can have a gas barrier layer and a moisture barrier layer. An additional layer may be included to enhance the structural integrity of the attenuation device. In one embodiment, the attenuation device has an outer layer comprising a gas barrier and an inner layer comprising a moisture barrier. In another embodiment, the attenuation device has an outer layer comprising a moisture barrier and an inner layer comprising a gas barrier.

The attenuation device can have three, four, five, or more layers. In one embodiment, the attenuation device has a gas barrier layer, a moisture barrier layer, and one or more layers composed of at least one high impact strength material. In another embodiment, the attenuation device has multiple gas barrier layers arranged in a nonconsecutive arrangement. In yet another embodiment, the attenuation device has multiple moisture barrier layers arranged in a nonconsecutive arrangement. With respect to those embodiments having multiple, nonconsecutive barrier layers, the other layers of the attenuation device can include high impact strength material layers and/or other types of barrier layers.

The overall thickness of the wall is preferably minimized, and will often be no more than about 0.03 inches. Preferably, the wall will be no more than about 0.006 inches, and, in some implementations, is no more than about 0.003 inches thick. An outer layer may comprise a soft, conformable material such as polyurethane, EVA, PE, polypropylene, silicone or others, having a thickness within the range of from about 0.0025 inches to about 0.025 inches. The adjacent barrier layer may comprise EVOH, PVDC or other materials in a thin film such as from about 5 microns to about 25 or 30 microns thick. If the attenuation device is fabricated by bonding two sides together, a bonding or tie layer may be provided on the barrier layer. Tie layers comprising polyurethane, EVA or others may be used, having a thickness of preferably no greater than about 0.001 inches. Layers of less than about 0.0008 are preferred, and layer thicknesses on the order of from about 0.0003 to about 0.0005 inches are contemplated.

The layers of the attenuation device can be formed in any number of ways known to those skilled in the art, including, but not limited to, lamination, coextrusion, dip molding, spray molding, or the like, etc. As discussed above, the layers of the attenuation device can be formed from various materials. With respect to those attenuation devices that are formed by laminating two or more layers together, various different laminating techniques known to those skilled in art can be used, including, but not limited to, heating, solvents, adhesives, tie layers, or the like.

The material may not need to be elastomeric at all for the attenuation device to function. However, the materials chosen for use in embodiments of the present invention are to be sufficiently flexible in the thickness ranges dictated by the selected designs. When the attenuation device is subjected to external pressures, the attenuation device's material is able to transmit the pressure to the contained air or pressure management construct and respond sacrificially as one of the most compliant members of the urinary system.

FIG. 16A illustrates a toroidal embodiment, in which a plurality of central spokes is provided. FIG. 16B illustrates a crescent or "C" shaped attenuation device. Any of a variety of spherical, oval, elliptical or other shapes may be utilized such as those illustrated in FIG. 16C, in which the greatest length dimension of the inflated attenuation device is within the range of from about 1 to about 5 times the smallest cross-section. FIG. 16D illustrates a less arcuate variety as shown in FIG. 16B. In general, the attenuation device 66 may take any of a variety of forms which provides a sufficient volume to achieve the desired attenuation function, and which will minimize or eliminate risk of loss or obstructing outflow through the urethra.

Figures 17A, 17B:
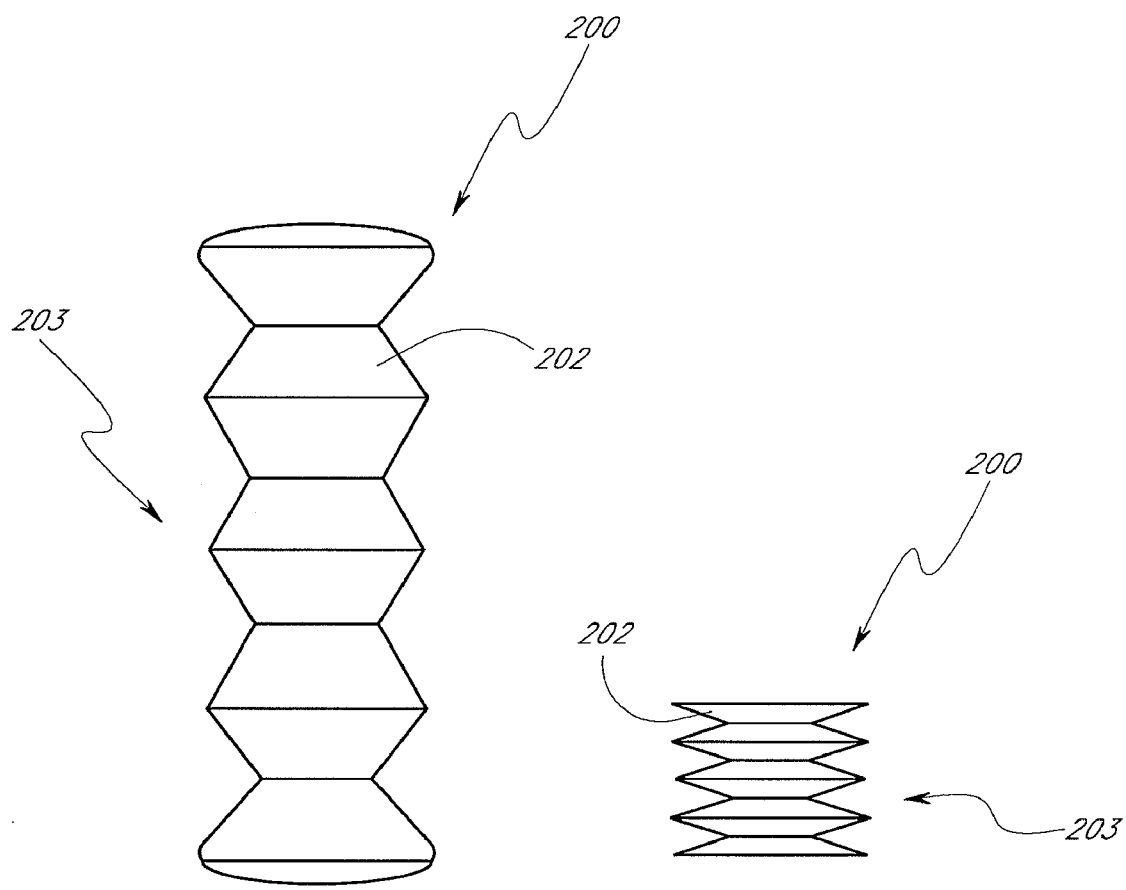
FIG. 17A is a side elevational schematic view of a bellow-type mechanically assisted attenuation device in an expanded configuration.
FIG. 17B is a side elevational schematic view of the attenuation device of FIG. 17A, in a compressed configuration attenuating a pressure spike.

Referring to FIGS. 17A-17B, there is illustrated a bellow-type attenuation device 200 in accordance with one embodiment of the present invention. FIGS. 17C-17F illustrate one environment in which the attenuation device 700 can be used.

The bellow 200 may be compressible to provide attenuation, as discussed further below. The compressiblity of the bellow 200 may be provided by a suitable mechanical structure or mechanism. For example, in one arrangement, a mechanism or mechanical structure is provided that enables the device to be axially compressible. In one arrangement, the bellow 200 comprises a membrane 202 that surrounds a volume. The membrane 202 may be self-supporting. The membrane 202 may be configured to be collapsible, such as in an accordion fashion. In some embodiments, a support structure such as a frame is provided. The frame or other support structure may be located on the inside of the membrane 202, e.g., within the volume defined therein, or external of the membrane. In some arrangements, a support structure is located in part inside a volume defined within the membrane 202 and in part outside the membrane. For example, a first portion of a support structure may be provided to maintain, at least in part, the external shape of the bellow 200 and a second portion may be provided for coupling the bellow device 200 to a vessel, as discussed further below.

Where provided, the support structure may comprise any of a variety of features, such as a simple spring aligned in parallel with (or configured to direct a restoring force along) a longitudinal axis of the bellow 200. Where provided, a support structure can comprise a pivotably moveable structure, such as an axially compressible wire pantograph, as will be understood in the art. Any of these and other mechanical structures can be located internally or externally to the membrane 202.

Various embodiments of attenuation devices for absorbing transient pressure changes or spikes may include one or more of diaphragmatic structures, rigid, or deformable structures (e.g., capable of changing shape). Attenuation devices for absorbing transient pressure spikes can be configured with a coating or covering that can dampen pressure waves in an organ or vessel. Attenuation devices for absorbing transient pressure spikes can include a bellow or bellow-like structure that can dampen pressure waves in an organ, chamber or cavity of the body, as discussed above. These embodiments can be configured as stand alone attenuation devices or as part of the wall or structure of the organ or vessel of interest, as discussed further below.

As discussed above, the bellow 200 is one form of a mechanically assisted attenuation device. The bellow 200 can be configured to relax to the extended position of FIG. 17A when at rest. In one arrangement, the extended position of FIG. 17A is a first state which occupies a first volume. The bellow 200 can be configured to relax to the extended position when not subject to a pressure above a selected level. Such a selected level is sometimes referred to herein as an activation level or an activation pressure. The activation level may be a threshold level. In some vascular applications, the activation level may be a level above which a risk of stroke, aneurysm or other deleterious cardiovascular event is appreciable. Such a level may depend at least in part on criteria of the patient. For example, for relatively young patients, the activation level may be a value of systolic pressure outside the range of normal systolic pressures that the patient might experience under a normal range of activities. For relatively old patients, the activation level might be selected to be within the range of systolic pressures that the patient could expect to experience under a normal range of activities. An activation level within a normal range could be selected to reduce the risk of a deleterious event, such as a stroke, where there are other risk factors, such as thinning or brittle vasculature. In other vascular applications, the activation level may be a level below which a vascular event is appreciable.

The bellow 200 can be configured such that the tendency thereof to expand to the position shown in FIG. 17A is balanced. For example, the pressure within the bellow 200 can be reduced such that the bellows normally retains its extended position, but will compress when an external pressure of a selected magnitude (e.g., at or exceeding the activation pressure) is exerted on it. The bellow 200 may be sealed, or covered in a material that allows for reduction of the pressure within the structure.

FIG. 17B illustrates a second state of the bellow 200. In particular, a portion of the bellow 200, such as an attenuation zone 203 thereof, can be compressed so that the bellow occupies less volume than in the first state. As discussed herein this response can attenuate pressure in an anatomical structure in which the bellow 200 may be placed. Accordingly, the bellow 200 can be used to attenuate pressure spikes that are in a range that can arise in a human body, e.g., physiologic pressure spikes.

The bellow 200 could be made from any suitable material, including a polymeric filmor a metal, such as, for example, titanium or stainless steel. The bellow 200 could be made from a combination of these or other suitable materials. Senior Flextronics, Inc. of Sharon, Mass. is one source for such materials.

One advantage of a mechanical attenuator such as the bellow 200 is that a large change of volume occupied by the bellow can be achieved, in response to a relatively small pressure rise beyond the present threshold. The change of volume of evacuated mechanical attenuators can be significantly greater than that achieved in devices that enclose or include a compressible medium. For example, an air or gas cell similar to those described herin might be able to be reduced by approximately 25% of its volume. Some mechanical attenuators can be reduced by at least about 30%, sometimes at least about 50% and in some implementations at least about 90% of its volume.

Figure 17C:
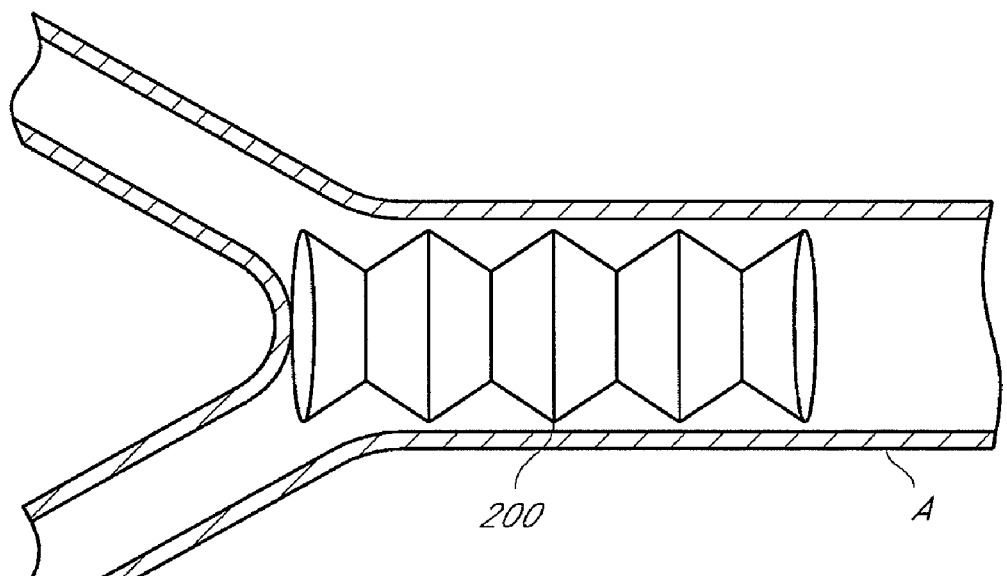
FIG. 17C is a side elevational schematic view of a bellow-type mechanically assisted attenuation device in an expanded configuration deployed in a blood vessel.
Figure 17D:
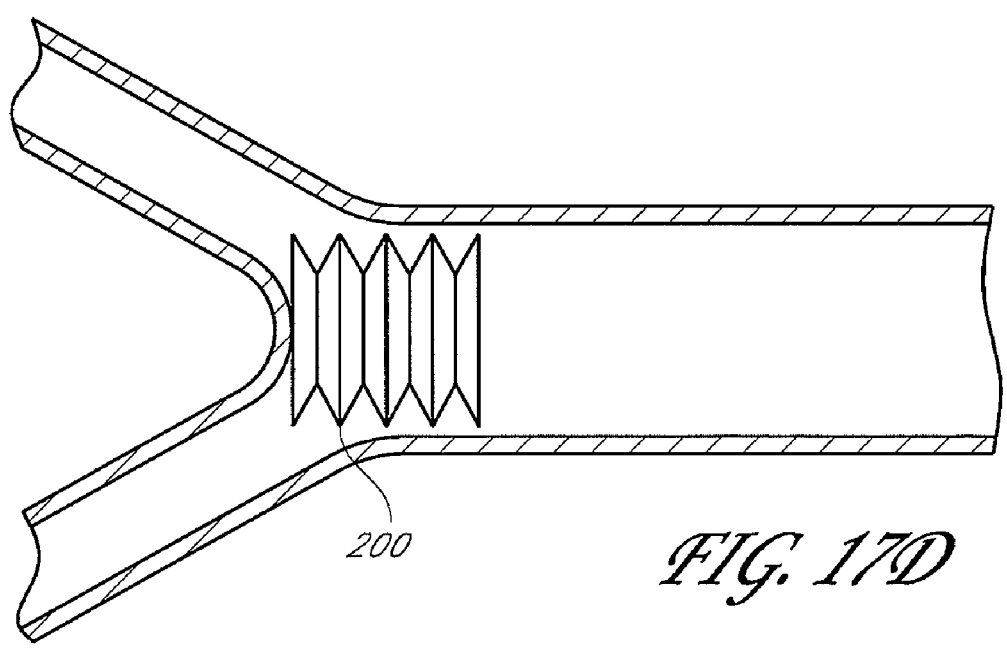
FIG. 17D is a side elevational schematic view of the attenuation device of FIG. 17C, in a compressed configuration attenuating a pressure spike in a blood vessel.

FIGS. 17C and 17D illustrate that the bellow 200 can be placed within the cardiovascular system. In particular, the bellow 200 is shown positioned in an aorta A, just above the bifurcation distal of the iliac arteries. FIG. 17C illustrates that the bellow 200 can be configured to be in a first, extended state when placed in a blood vessel. FIG. 17D illustrates the response of the bellow 200 to a physiologic pressure spike. In particular, the bellow 200 is shown moved from the first state to a second, compressed state. The second state occupies less volume than the first state. Because the bellow 200 occupies less volume, more volume within the vessel is available for blood. The difference in volume between the first and second states preferably is sufficient to alleviate at least one cardiovascular malady, such as excessive systolic pressure. In some applications, the difference in volume between the first and second states is sufficient to reduce a pressure spike within the vasculature.

Figure 17E:
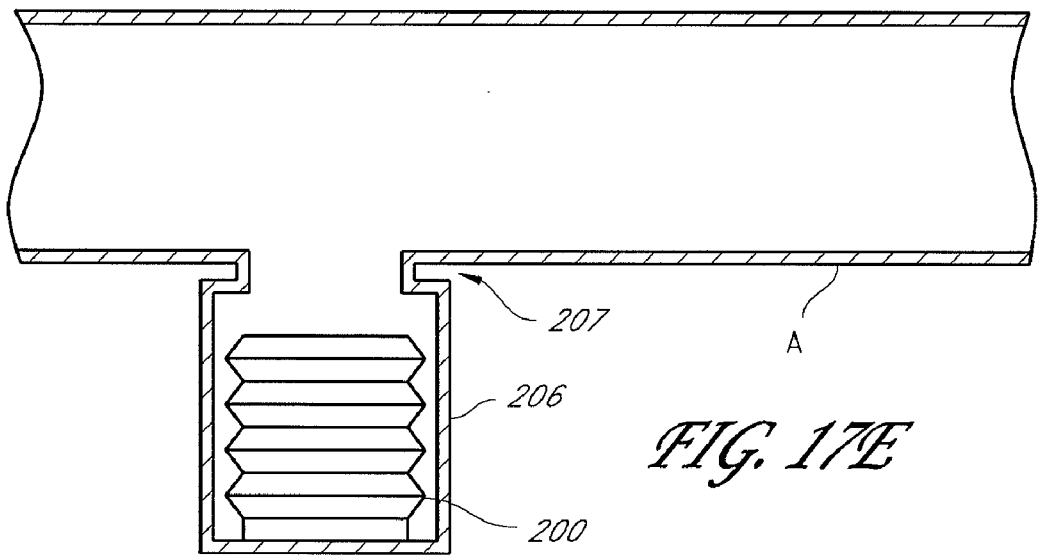
FIG. 17E is a side view of the attenuation device from FIG. 17A in a container, in proximity to a blood vessel with the bellow expanded.
Figure 17F:
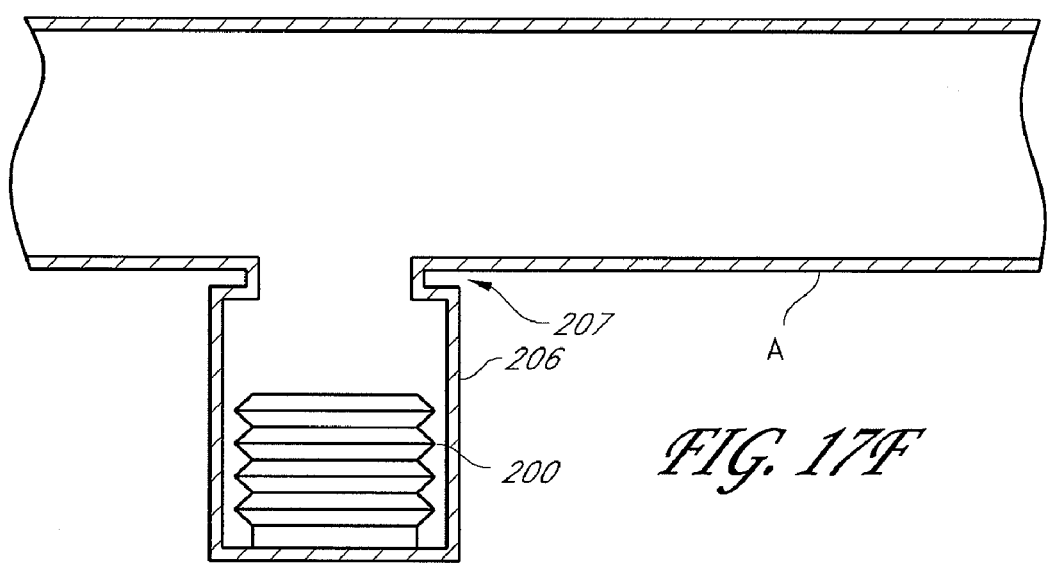
FIG. 17F is a side view of the attenuation device of FIG. 17E with the bellows in compressed configuration attenuating a pressure spike.

Referring to FIGS. 17E and 17F, the bellow 200 can be placed in proximity to or in pressure communication with the vasculature. In this arrangement, a container 206 is provided in which the bellow 200 or other attenuator can be contained or mounted. In one arrangement, the container 206 comprises a connection zone 207 for connecting the bellow 200 to a blood vessel. The container 206 can be sutured or otherwise affixed to the vasculature. The container 206 and the bellow 200 can be coupled together in any suitable manner. In one arrangement, a portal or opening is provided between the container 206 and the vasculature such that blood is in fluid communication with the bellow 200. In another arrangement, the container 206 and the bellow 200 are in pressure communication with the vasculature without requiring fluid communication between the portion of the container housing the bellow 200 (e.g., an inside volume of the container 206) and the vasculature. Where the bellow 200 is in fluid communication with the vasculature, any suitable technique may be used to maintain flow into the container 206, such as providing suitable anticoagulation therapy. The bellow 200 and the other implantable blood pressure regulators can be combined with another treatment, such as a pharmaceutical therapy, to manage a cardiovascular malady, as discussed further below.

Although FIGS. 17C-17F illustrate the bellow 200 in pressure and in fluid communication with a patient's aorta, the bellow device and other pressure regulators disclosed herein can be applied to other vessels through the vasculature.

Figure 18:
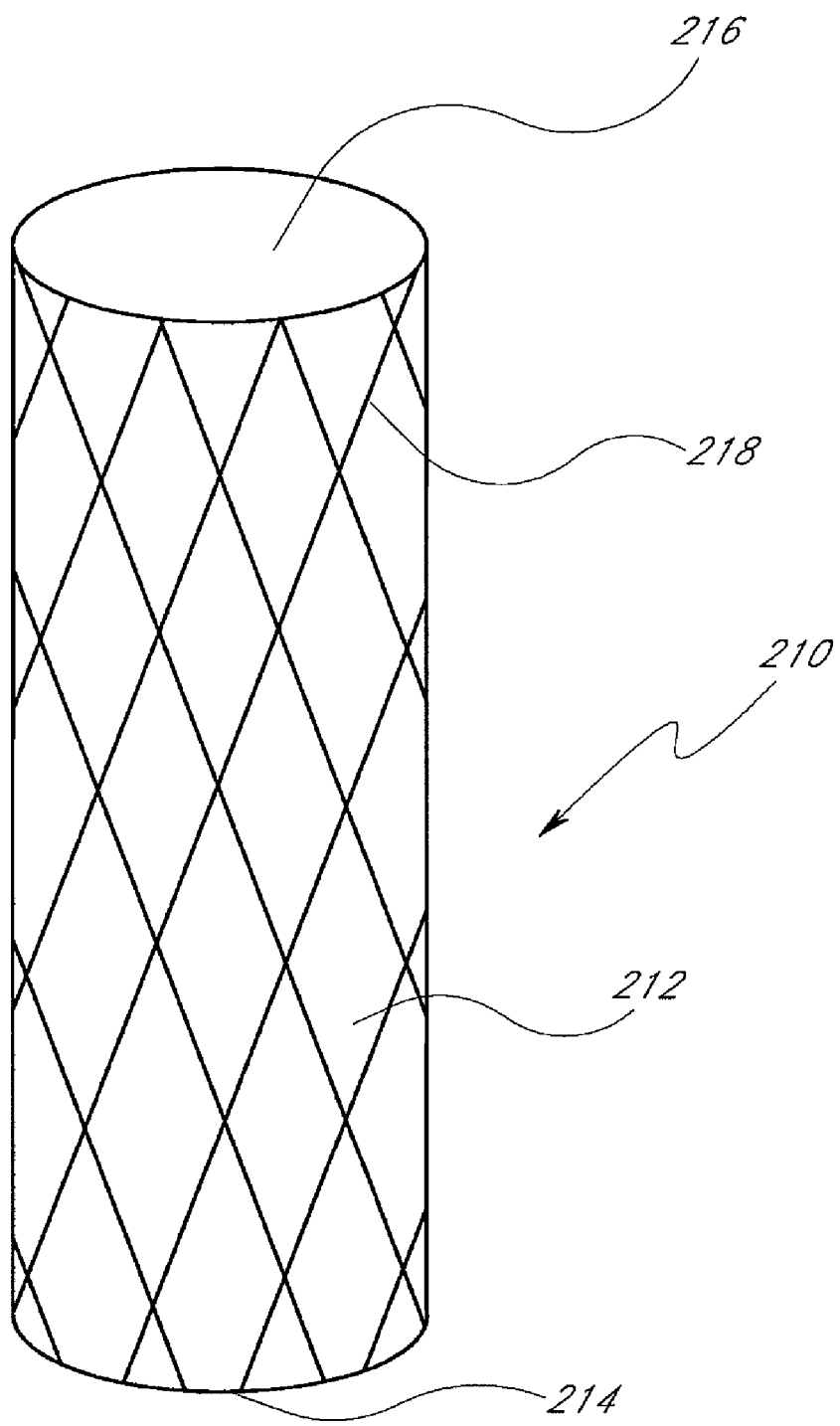
FIG. 18 is a side elevational schematic view of a self-expanding graft type mechanically assisted attenuation device.

Referring to FIG. 18, there is illustrated a mechanically-assisted attenuation device 210 in accordance with the present invention. In this embodiment, a compressible tubular wall 212 having closed ends 214, 216 is supported by a self-expanding tubular frame 218. Any of a variety of self-expanding tubular or spherical frame structures may be utilized, such as "zigzag" wire frames well known in the abdominal aortic aneurysm graft arts. Although the abdominal aortic aneurysm graft application generally requires a relatively high, radially outwardly directed force, the present application would preferably be compressible with a relatively low compressive force (i.e., low radial force). This may be accomplished by using wires of smaller gauge, less wire per graft, leaving adjacent apexes unconnected to each other, or other technique t6 reduce the radial force of the wire cage. The wire cage or other support structure is preferably surrounded by a water impermeable membrane such as a balloon. Pressure within such balloon may be lower than 1 atm.

Figure 19A:
FIG. 19A is a side elevational schematic view of a multiple chamber attenuation device in accordance with a further aspect of the present invention.
Figure 19B:
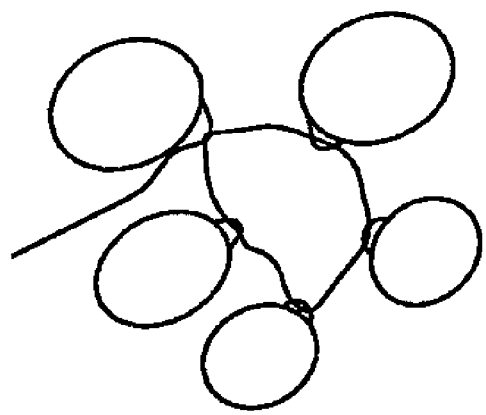
FIG. 19B is a schematic illustration of the multiple chamber attenuation device of FIG. 19A, in a deployed orientation to ensure retention within the bladder.

Referring to FIGS. 19A and 19B, there is illustrated another layout for the inflatable attenuation device 66 of the present invention. In this embodiment, illustrated in FIG. 19A, a plurality of attenuation devices 67 are connected by a common flow path 65, so that the plurality of attenuation devices 67 can be inflated through a single fill port. In another embodiment, illustrated in FIG. 19B, a plurality of self-expanding attenuation devices are connected by a suture, Nitinol wire, or other tether, thereby minimizing the crossing profile and/or maintaining a constant crossing profile for an attenuation device of any desired total inflated volume.

FIGS. 20-23 illustrate a magnetic locating system for enabling "blind" retrieval without the use of a cystoscope. To remove the attenuation device from the bladder, the removal system is inserted into the urethra for intravesical capture, deflation, and extraction of the attenuation device. The removal system utilizes a magnet whose polarity and flux path is oriented in a manner to ensure predictable attraction and coupling of a magnet-containing attenuation device to the removal system. The removal system is coupled back to the attenuation device, and the attenuation device may be punctured and deflated using the jaws of biopsy-like forceps (or other solution suitable for deconstructing the device) located at the distal end of the removal system. In one embodiment, residual gas may be passively vented into the bladder or through the retriever body. Once deflated the attenuation device may be withdrawn through the urethra attached to the removal system or allowed to pass out of the bladder as part of the urine flow.

Figure 20:
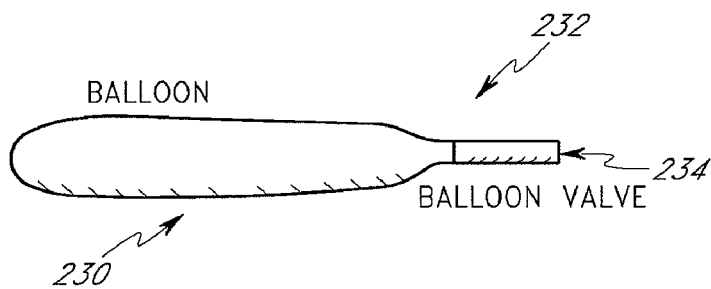
FIG. 20 is a side elevational schematic view of an inflatable balloon-type attenuation device, having a locatable balloon valve thereon.

Thus, referring to FIG. 20, there is illustrated an attenuation device 230 such as an inflatable balloon 229 as has been described previously herein. The attenuation device 230 is provided with a valve 232 and a locating element 234. Locating element 234 may be any of the variety of structures which enable location of the attenuation device 230, preferably without the need for direct visualization.

In the illustrated embodiment, the locating element 234 is one or more magnets 236. In the embodiment illustrated in FIG. 21, the magnet 236 comprises an annular ring, for surrounding the flow path 83. A corresponding magnet 238 having reversed polarities from the polarity of the magnet 236 is provided on the distal end of a catheter 240. The attractive forces of the opposing polarity magnets 236 and 238 will cause the catheter 240 to couple on to the attenuation device 230, as illustrated in FIG. 22, when the catheter 240 is positioned in the vicinity of the attenuation device 230.

Figure 22:
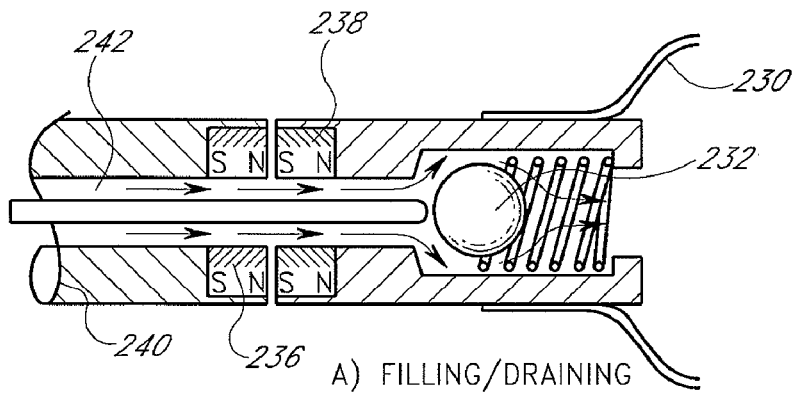
FIG. 22 is a fragmentary cross-sectional view through the distal end of a delivery or removal system, and the proximal end of the valve on an attenuation device, illustrating the valve in a filling or draining orientation.
Figure 23:
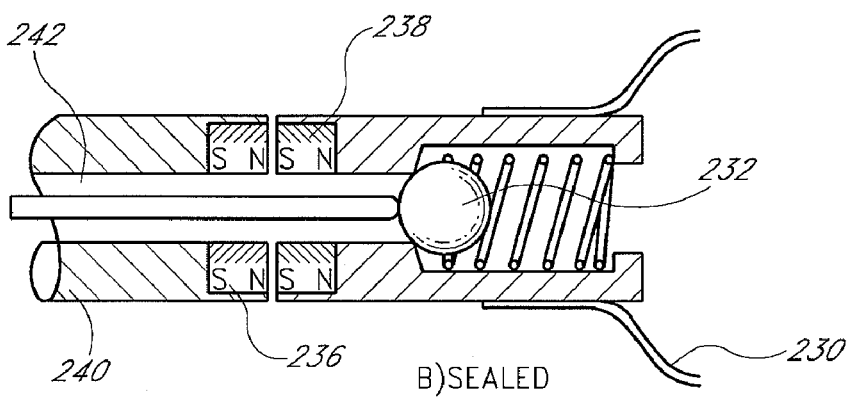
FIG. 23 is a fragmentary cross-section as in FIG. 22, showing the valve in a sealed orientation.

Referring to FIG. 22, at least one lumen 242 places the attenuation device 230 in fluid communication with the catheter 240 when the locating element 234 is coupled to the catheter 240. This lumen 242 may be utilized to either introduce inflation media or remove inflation media from the attenuation device 230. In FIG. 22, the valve 232 is a ball valve, which is biased in the closed orientation. However, the mechanism and structures disclosed herein may be used on any of the other valves disclosed elsewhere herein. In one embodiment, illustrated in FIG. 22, a valve actuator 234 may be advanced distally through the lumen 242 to displace the valve 232 and enable infusion or removal of inflation media. Following the desired volume of infusion or removal of inflation media, the valve actuator 234 may be proximally retracted, to enable the valve to close under its own bias. See FIG. 23.

The opposing magnets 236 and 238 may be utilized solely as a locating structure, such that an additional locking element (not illustrated) may be utilized to lock the catheter 240 on to the attenuation device 230. This may be desirable if the strength of the bond formed between the two magnets is insufficient to keep the attenuation device 230 coupled to the catheter 240 during the filling or removal steps. In addition, following deflation of the attenuation device 230, the catheter 240 will generally require a relatively strong coupling to the attenuation device 230 to retrieve the attenuation device 230, as will be apparent to those of skill in the art in view of the disclosure herein.

In accordance with one aspect of the present invention, the removal system is provided with one or more ultrasound transducers near a distal end thereof. An air filled attenuation device should strongly reflect an ultrasound signal, in a manner similar to the reflection achieved at an air-water interface. A removal system provided with a deflectable distal tip and ultrasonic capabilities should be able to navigate through the bladder to locate an attenuation device without the need for visualization. The removal system may additionally be provided with a grasping element, such as two or more opposing mechanical graspers, and/or a vacuum lumen, for attaching to the surface of the attenuation device using suction. Once attached, the attenuation device can be pierced and transurethrally withdrawn.

In accordance with another aspect of the present invention, there is provided an attenuation device that may assume multiple shapes during the course of its use. For example, the attenuation device may be completely deflated for introduction and inflated to varying degrees after introduction. The attenuation device may be adjusted through the inflation/deflation of secondary or multiple containment cells for such purposes as ballasting or the addition of a diagnostic, therapeutic or signaling substance. This may occur through multiple uses of a single, or single uses of a multi lumen, multi ported structure or combinations thereof.

In accordance with another aspect of the present invention, the delivery system and the removal system of the attenuation device or accumulator are two separate instruments. In another embodiment, the delivery system and the removal system are implemented using a single instrument. In yet another embodiment, there is provided one instrument having different distal ends for the delivery system and the removal system.

In accordance with another aspect of the present invention, an endoscope may be used to launch and retrieve the device (i.e. attenuation device, accumulator, etc.).

In accordance with another aspect of the present invention, the distal tip of the delivery system may be straight, precurved, malleable, or steerable (e.g., by pull wires) in order to facilitate delivery and/or release of the device.

In accordance with another aspect of the present invention, the separation of the attenuation device from the fill tube may be accomplished using the wall of the urethra or neck of the bladder as a mechanically resistant body.

In accordance with another aspect of the present invention, the delivery system may consist of a single tubular element, a series of concentric tubular elements, a series of non-concentric tubular elements, an extruded element, a spirally wound guidewire element, or any combination of the aforementioned elements arranged in a manner to provide the desired functions.

In accordance with another aspect of the present invention, irritation concerns are addressed through the use of coatings or fillers to physically or chemically modify the attenuation device in whole or part in order to modulate characteristics such as lubricity and the ability to inhibit the deposition of materials present in the urinary tract. For example, substances such as sulfated polysaccharides may be used before, during, or after introduction to the patient. In addition, the use of a plurality of construction materials with unique surface properties may also be used for this purpose.

In accordance with another aspect of the present invention, the attenuation device includes a portal that spans the distance from the internal aspect to the external aspect that allows for the location of an erodable substance that would allow for the deflation or deconstruction of the attenuation device after exposure to urinary tract conditions for a prescribed period of time. This approach may also be used for the programmed bolus release of single or multiple therapeutic, diagnostic or signaling substances from single or multiple chambers within the attenuation device.

In accordance with another aspect of the present invention, the attenuation device is equipped with a valve/port that is programmable, self-regulating or responsive to stimuli, which may or may not be physiological. Telemetry, physical connection or remote signaling may be used to elicit a desired response.

In accordance with another aspect of the present invention, the attenuation device accepts, captures, and/or translates physical forces within the urinary tract to energize a site within the attenuation device for the positive displacement of substances outside the boundary of the attenuation device in either continuous or bolus presentation.

In accordance with another aspect of the present invention, there is provided a port/valve that is not associated with the sealing edge of the attenuation device.

Figure 24:
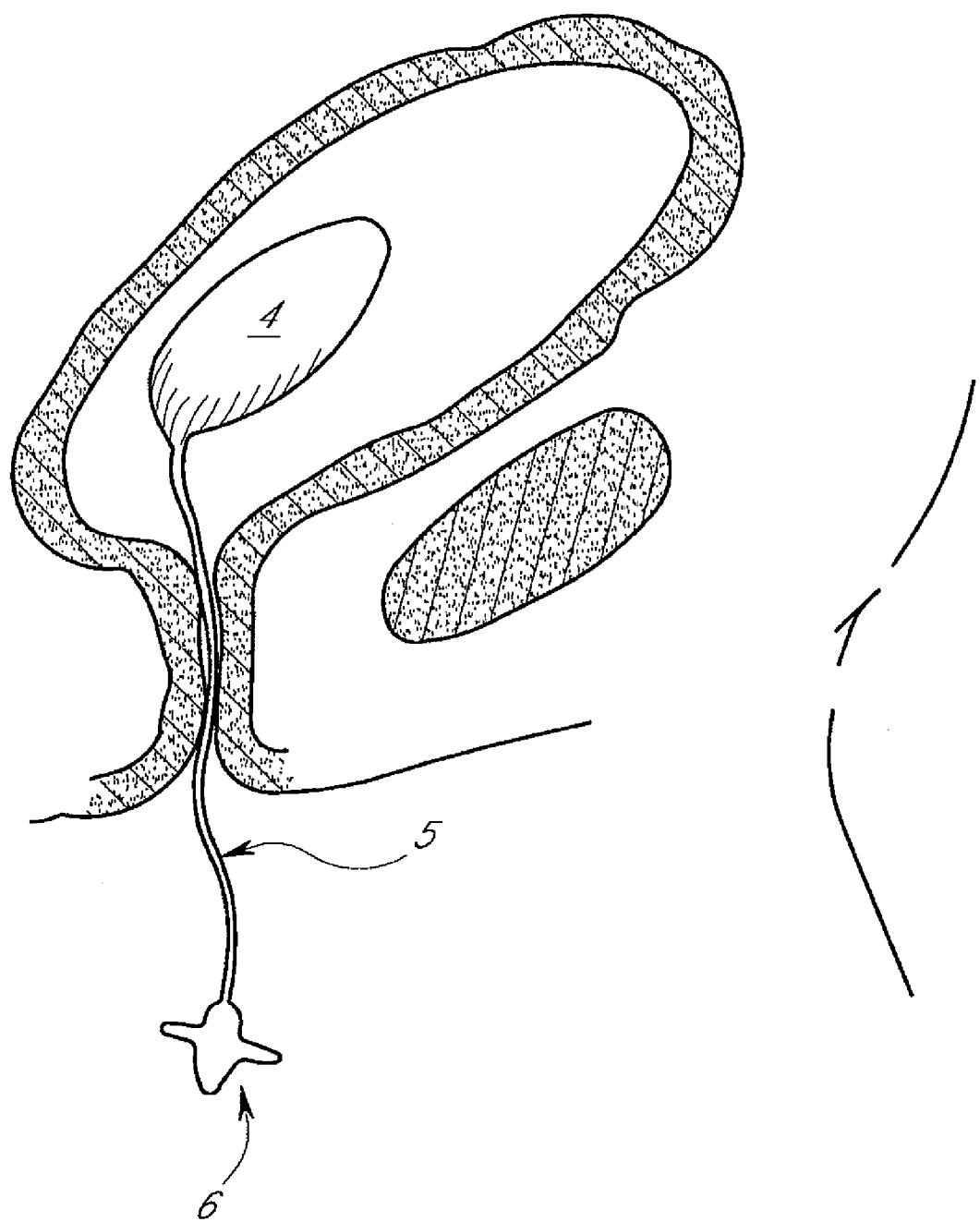
FIG. 24 is a schematic cross-section through a bladder, showing an attenuation device therein, having an attached, external tether.
Figure 25:
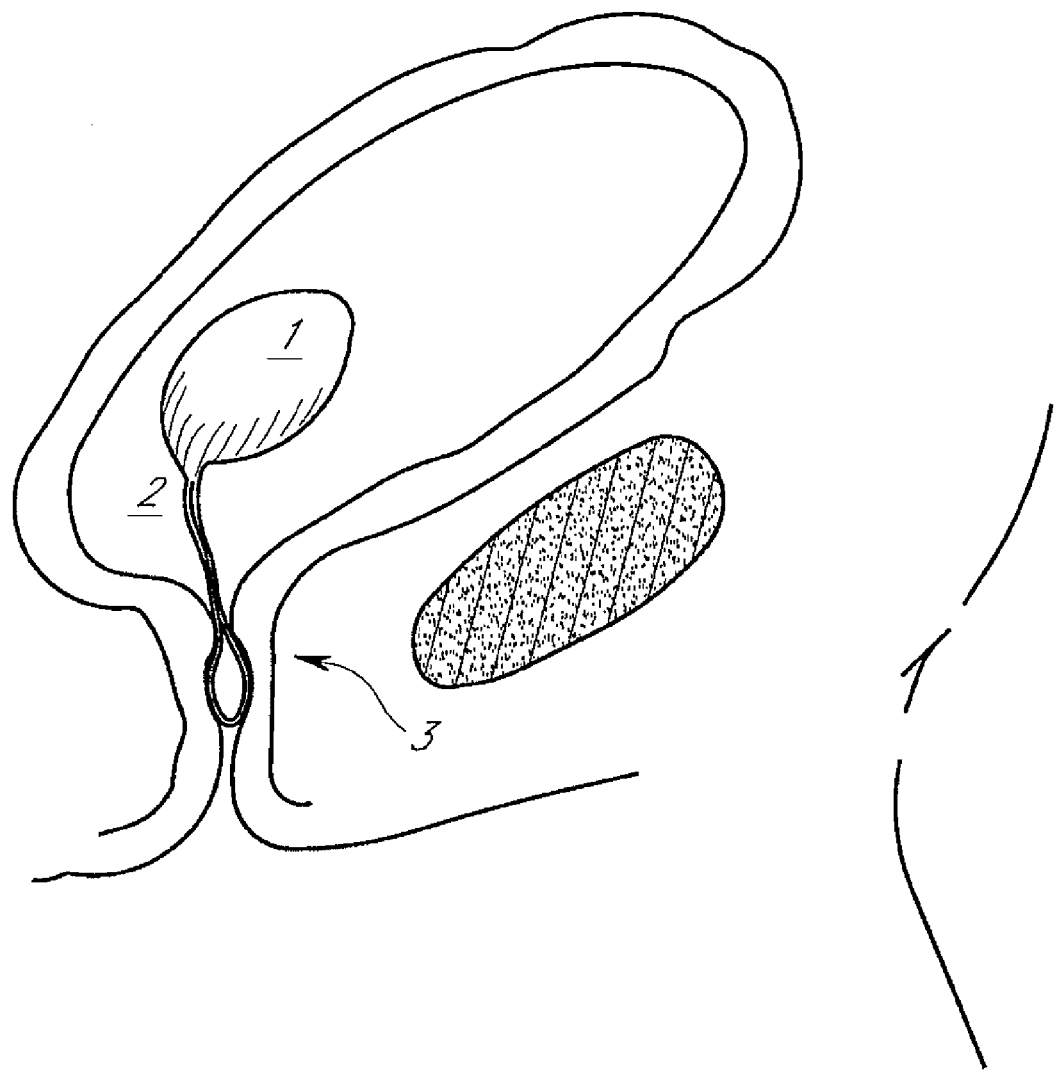
FIG. 25 is a schematic cross-section through a bladder, showing a two-component attenuation device in which a primary compressible component is positioned within the bladder and a secondary inflatable component is positioned within the urethra.

In accordance with another aspect of the present invention, there is provided an attenuation device that includes a thin, pliable safety tether 332 long enough to extend from the attenuation device and exit from the meatus. See FIG. 24. The tether can be constructed of accepted materials such as those used in the manufacture of sutures, catheters and may also possess anti-microbial properties. In one embodiment, the distal end of the tether may be terminated with a lightweight pendant 334 of sufficient bulk to prevent ingress of the entire tether into the urethra. During normal use, the pendant may be temporarily affixed to the patient's pelvic region. The tether may be used to remove or deconstruct the attenuation device, and the tether provides the patient with the capability of instant removal of the attenuation device in the event the patient feels compelled to extract the attenuation device.

In accordance with another aspect of the present invention, there is provided an attenuation device that is a chambered structure consisting of multiple subchambers for multiple functions. See FIGS. 25 and 25A-C. The primary attenuation device 336 may or may not be fluidically connected to the secondary device 338. The fluidic connection 340 also acts as a tether with sufficient service loop to allow the secondary device 338 to be placed into the urethra while the primary attenuation device 336 remains untethered in the bladder 63, located above the pubic bone 69. During a urinary pressure spike, gas within the primary attenuation device 336 compresses proportionally with the external load. The compressed gas is then allowed to transfer to the secondary device 338, dwelling in the urethra, and causing a proportional expansion of the secondary device 338. The design of the secondary device 338 directs expansion in an outward radial direction, transverse to the longitudinal axis of the urethra, thus augmenting the natural inward radial contraction of the urethra. This type of "on demand" synchronous resistance augmentation may be much more effective than other forms of passive or patient controlled augmentation systems. Another benefit of this embodiment of the present invention is that the synchronous outward radial forces may help to positionally stabilize the secondary device within the urethra. Passive devices must maintain a constant retention capability (force or displacement of tissue) sufficient to resist the maximum expulsion forces at all times. This level of retention may lead to patient discomfort and cause long-term tissue damage.

Figure 26:
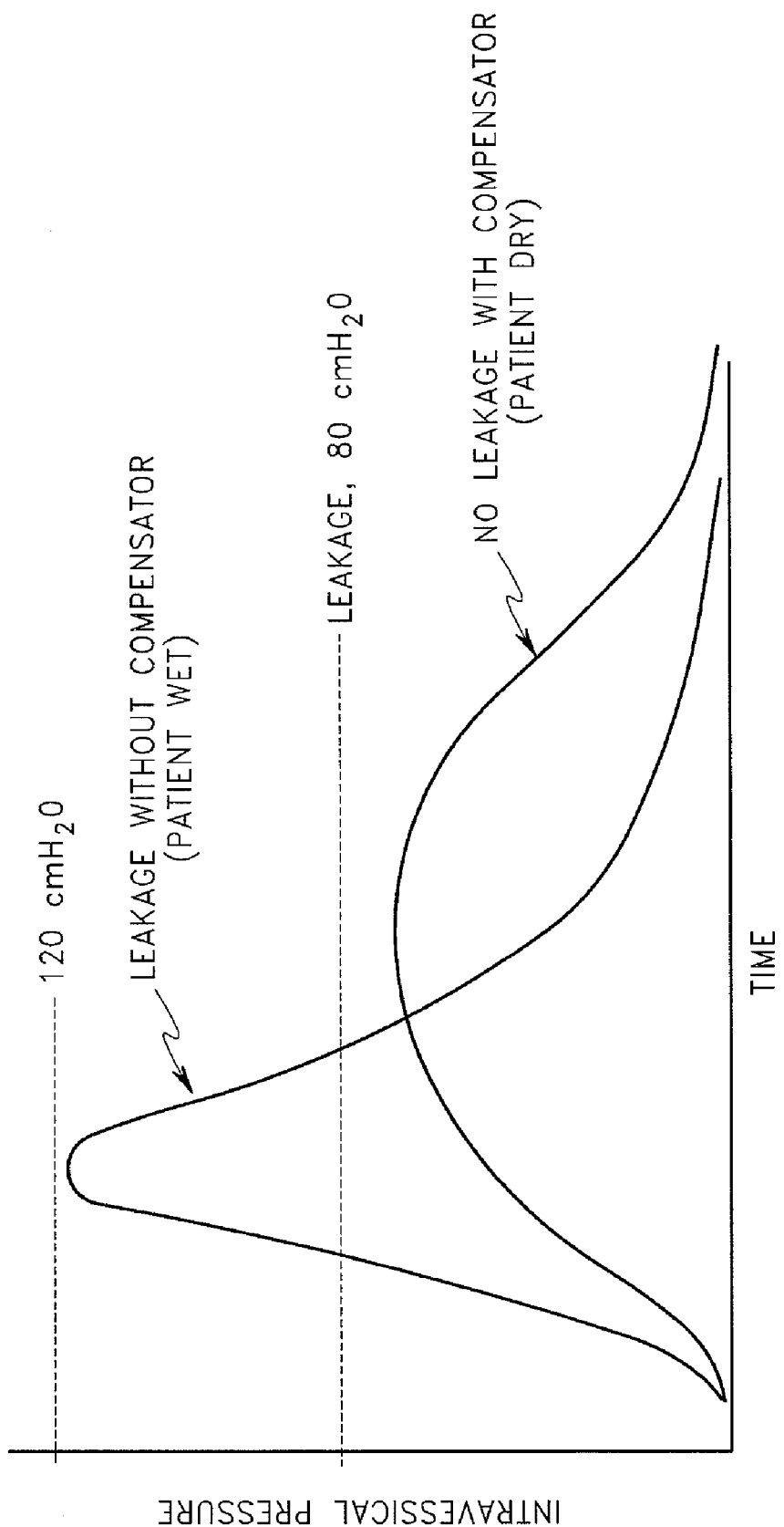
FIG. 26 illustrates the effect on intravesical pressure of the presence of an implanted attenuation device in accordance with the present invention.

With reference to FIG. 25B, compression force ($F_{comp}$) 342 equals the sum of ingress force ($F_{ingress}$) 344 and the egress force ($F_{egress}$) 346. With reference to FIG. 25C, the intravesical pressure 348 exhibits a rapid rise time and a rapid decay time. The secondary device pressure 350 exhibits a rapid rise time and a delayed decay time. FIG. 26 illustrates the effect of an attenuation device on the intravesical pressure. Here, the intravesical pressure 352 with the attenuation device exhibits delayed rise and decay times and remains below the leakage pressure of 80 cm H2O. This is contrast to the intravesical pressure 354 which exceeds the leakage pressure.

Figure 27:
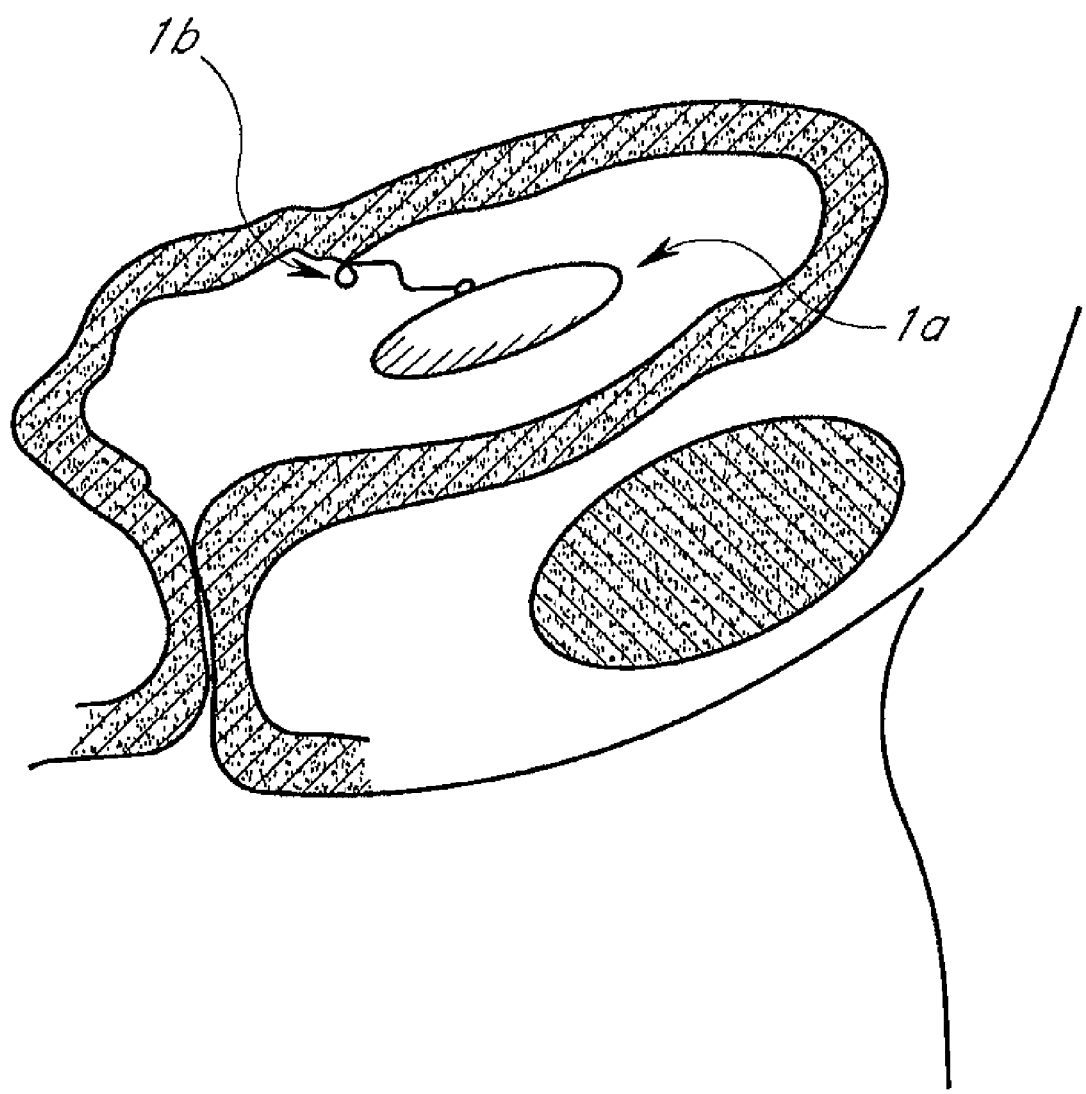
FIG. 27 is a schematic cross-sectional view through a bladder, showing an attenuation device anchored to the bladder wall.
Figure 28:
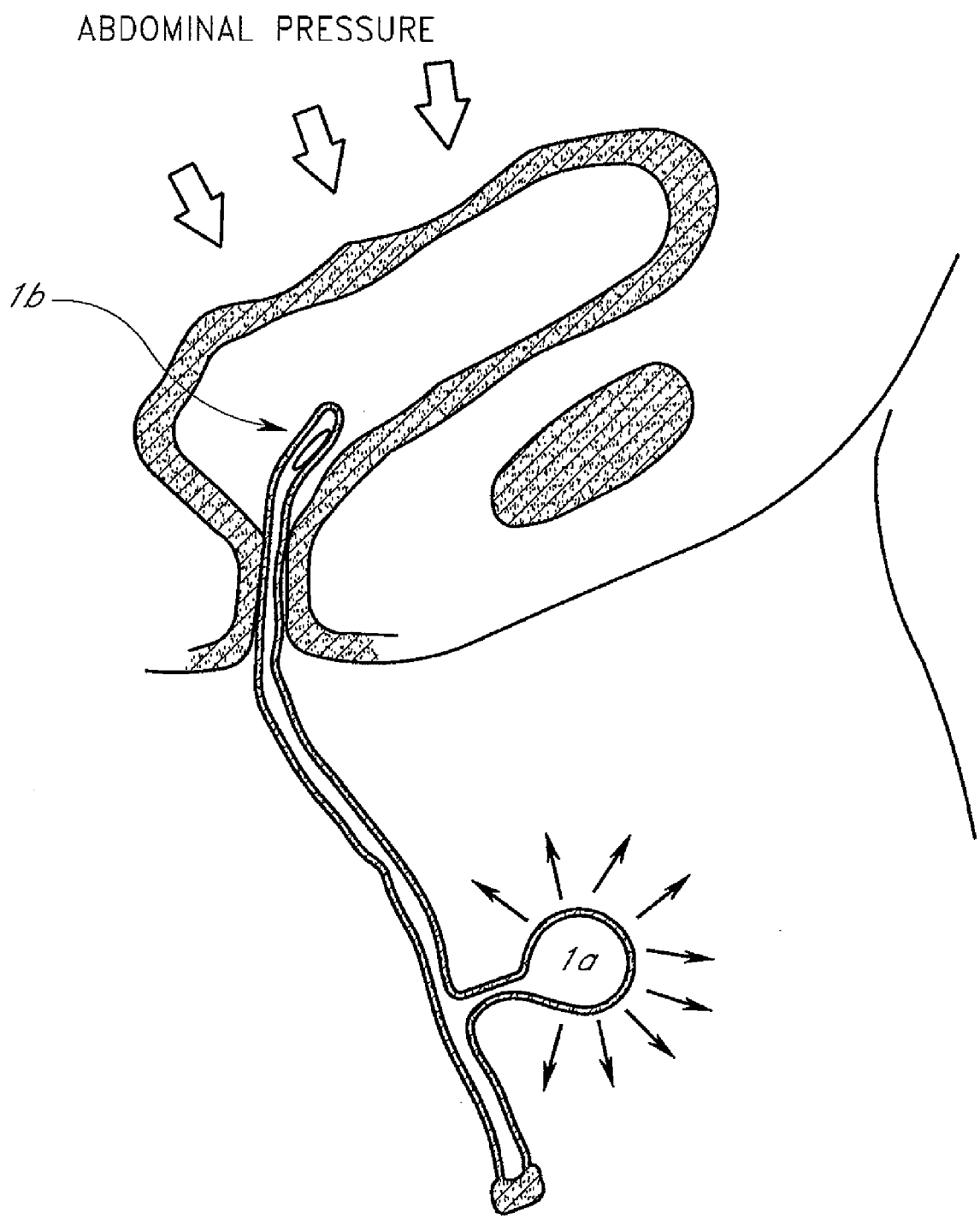
FIG. 28 is a schematic cross-sectional view showing a bladder, and the transurethral placement of a dynamic compliancy measurement catheter in accordance with the present invention.

With reference to FIG. 27, in one embodiment, the attenuation device 66 is anchored to the bladder wall 356. In another embodiment, shown in FIG. 28, the attenuation device 66 is part of a tranurethrally-placed dynamic compliancy measurement catheter 358. In other embodiments of the present invention, the attenuation device may resemble a small three-spoked automotive steering wheel, or a rotating toroidal space station. See FIG. 16A. The outer ring would contain the attenuation device; the inwardly radiating spokes would provide fluid conduits and mechanical support for the secondary device attachment. The attenuation device may also incorporate one or more shape holding super elastic wire members to aid in positional stability. The secondary device could resemble the distal tip section of a small diameter angioplasty device and be affixed to the central hub.

In accordance with another aspect of the present invention, a secondary device inflation/deflation response can be design regulated. For example, it may be beneficial to inflate the secondary as quickly as possible, but induce a response lag in the deflation/inflation cycle to protect against a second cough, sneeze or sudden mechanical shock.

In accordance with another aspect of the present invention, there is provided a pressure compensator or bladder trainer that can be implanted within a treatment site, such as, for example, the abdominal cavity, and be hydraulically or pneumatically connected to the bladder or be installed as a component of the bladder wall. The device would be constructed of a rigid external enclosure to shield the compressible elements from abdominal forces. The function of this embodiment would be not only to manage the transvescular pressure in treatment of a clinical insult, but also to introduce pressure waves either outside or inside the bladder in order to increase the muscle tone, compliance or affect the neuromuscular elements of the bladder.

The embodiments of the present invention have been described for use in the human anatomy. As understood by those skilled in the art, the present invention is not limited to human use; rather appropriately scaled versions of the inventions disclosed herein can be used to provide clinical benefits to other animals, including but not limited to mammalian household pets.

Certain embodiments of the present invention provide significant advantages over prior art devices. These advantages include but are not limited to: significant reductions in bladder dysfunction related events; the ability to retrain a bladder with other than normal compliance; no patient interaction required to operate or maintain the attenuation device; patient is allowed to void in a normal fashion; no infection conduit between the bladder and the distal end of the meatus; minimal sensation generated by the attenuation device; low cost to manufacture; cost effective solution for patient when compared to existing treatments; and ease of installation and removal for clinician.

In accordance with one aspect of the present invention, there are provided devices and methods for measuring the dynamic compliance of the bladder. In one embodiment, a device can be used in combination with the fill tube/introducer to measure the dynamic compliance of the bladder. One lumen of the fill tube can be used to rapidly inflate the device, while pressure measurements of the bladder are made via a second lumen. In one embodiment, the volume is expanded by at least about 30 cc or 50 cc up to as much as 200 cc in a time period of from about 0.5 to 10 seconds to measure the dynamic compliance of the bladder.

In accordance with another aspect of the present invention, there are provided methods and devices for the restoration of dynamic compliance of the bladder by retraining the bladder tissue by introducing pressure waves at a prescribed place and with prescribed characteristics.

In accordance with another aspect of the present invention, there are provided methods and devices for the programmatic delivery of clinical therapeutics in association with defined pressure events. The present invention could be added to other intravesical devices, such as Foley catheters, intravesical infusers, such as those described in WO1998US0021368, filed Oct. 9, 1998, titled intravesical infuser (the disclosure of which is incorporated in its entirety herein by reference), or the ends of urethral stents to facilitate delivery, to treat multiple symptoms, or to enhance the performance of either device. For example, the attenuation device could work in combination with intravesical infusers, to time the release of medications relative to pressure events within the bladder.

In accordance with another aspect of the present invention, there is provided an atraumatic method of measuring intravesical pressure without the need for any external connection by placing a pressure transducer and telemetry device within the attenuation device. This secures the transducer within the bladder and prevents the need to attach the transducer to the bladder wall.

Figure 29:
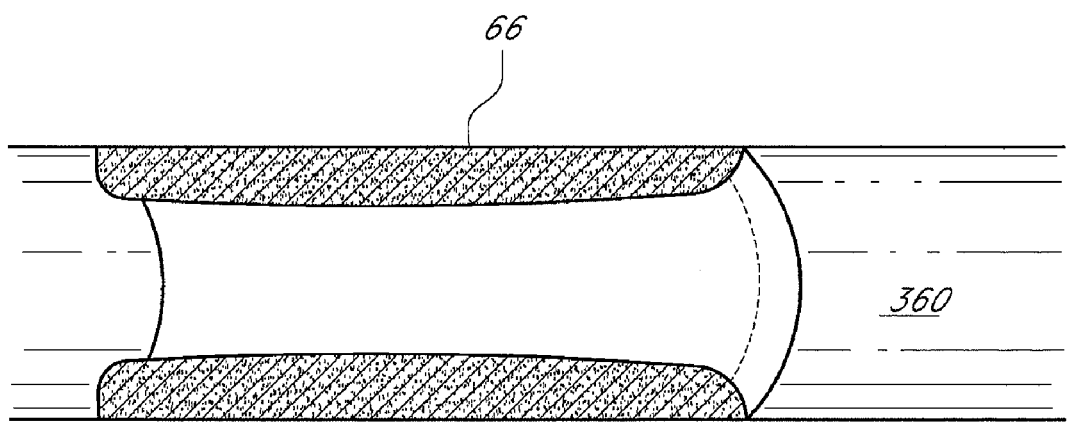
FIG. 29 is a schematic cross-sectional view through a blood vessel, illustrating an attenuation device deployed therein.

FIG. 29 shows another attenuation device that can be placed in pressure communication with a blood vessel. In particular, an attenuation device 66 is shown implanted in a vessel 360 to modulate or regulate blood pressure. The vessel 360 can be any vessel in which pressure waves propagate and in which pressure waves can be attenuated to provide a physiologic benefit. In some applications, the vessel 360 is a vessel between the iliac arteries and the heart. In some applications, the vessel 360 is a carotid artery or other vessel carrying blood to the patient's brain. In some applications, the vessel 360 is a vessel carrying blood from the patient's brain. In some applications, the vessel 360 is the patient's aorta. For example, the attenuation device 66 can regulate pressure waves to protect a portion of the cardiovascular system from being damaged due to exposure to normal or extreme physiological events as discussed above. The attenuation device 66 can be used to reduce at least one of mean arterial pressure, systolic pressure, diastolic pressure, and pulse pressure. The attenuation device 66 can be used to protect the vasculature from being damaged, e.g., from aneurysm or stroke, due to exposure to normal or extreme pulsitile forces or normal or extreme physiological events. An attenuation device can be placed in the wall of the heart or within a major artery.

Figure 29A:
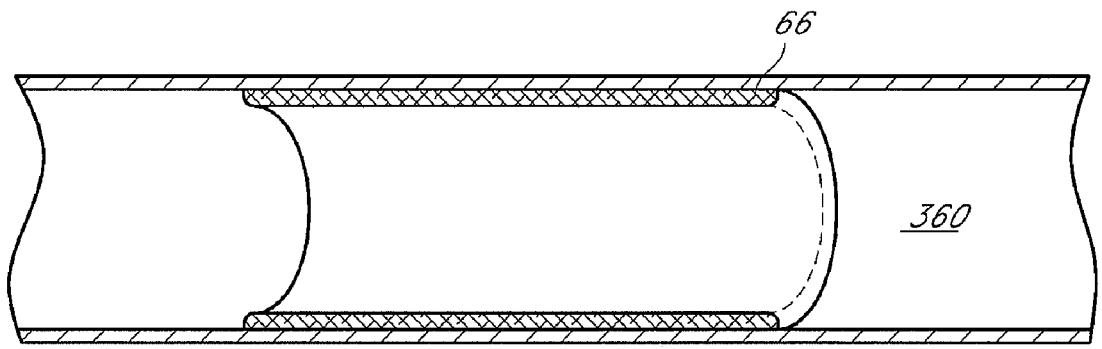
FIG. 29A is a schematic cross-sectional view through a blood vessel, illustrating an attenuation device deployed therein, the attenuation device being in a compressed configuration attenuating a pressure spike in the blood vessel.
Figure 29B:
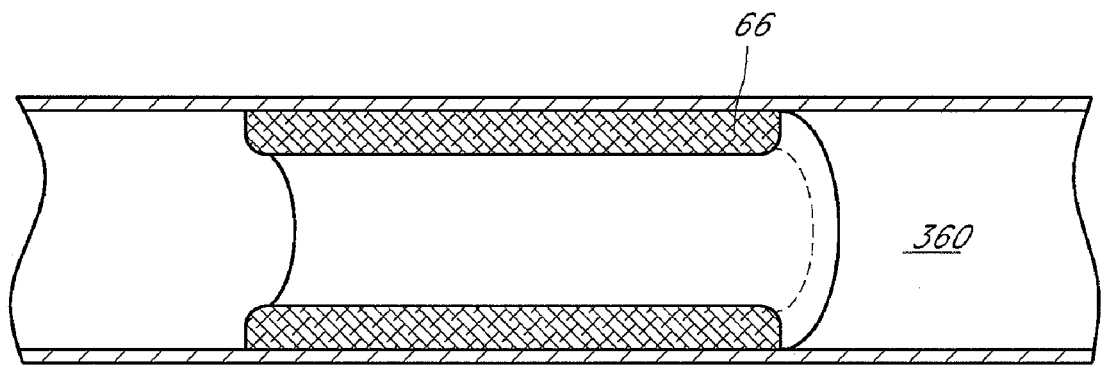
FIG. 29B is a schematic cross-sectional view through a blood vessel, illustrating an attenuation device therein returning to an expanded configuration after attenuating a pressure spike in the blood vessel.

FIGS. 29 and 29B show the attenuation device 66 in a first, enlarged or equilibrium state. The first state can correspond to diastole or to diastolic pressure within the vasculature at the location of the device. FIG. 29A depicts the attenuation device 66 in a second, reduced volume state. The second state is induced as a response to a physiologic pressure spike. For example, the second state could be due to an abnormal pressure spike, such as those described herein, or a normal pressure increase due to systole.

Figure 29C:
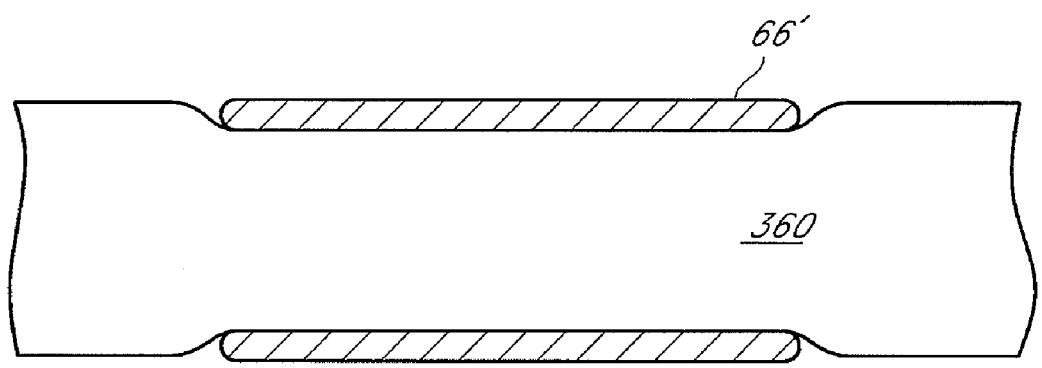
FIG. 29C is a schematic cross-sectional view through a vessel, illustrating an attenuation device in proximity to the vessel, in a compressed configuration attenuating a pressure spike.
Figure 29D:
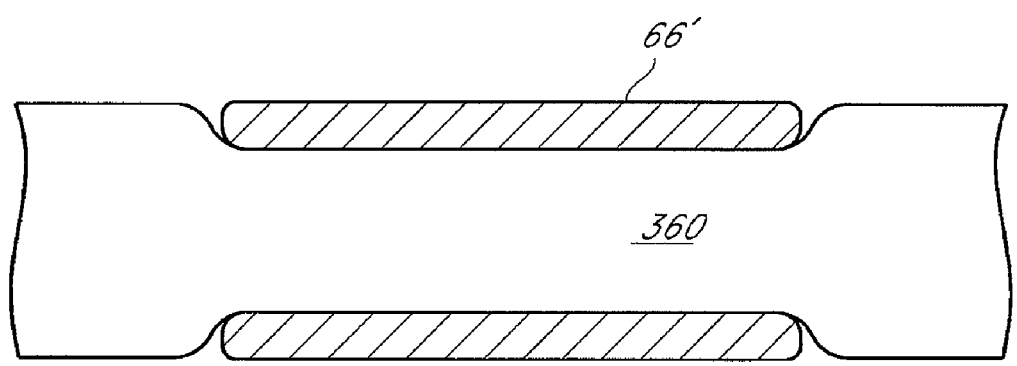
FIG. 29D is a schematic cross-sectional view through a vessel, illustrating an attenuation device in proximity to a blood vessel, the device returning to an expanded state after attenuating a pressure spike.

FIGS. 29C and 29D illustrate that in some embodiments, a pressure regulator or attenuation device 66' can be placed in pressure communication with a blood vessel 360 without being in fluid communication with the blood flowing therein. The pressure regulator 66' is an elongated, tubular device in one embodiment that is disposed at least partially around the exterior of a segment of the vessel 360. The pressure regulator 66' can fully encircle the vessel A in some embodiments. FIG. 29C illustrates that in response to a physiologic pressure spike, the pressure regulator 66' can be moved to a compressed state. In particular, an internal volume and any fluid contained therein can be compressed in response to the pressure spike. FIG. 29D illustrate that when the physiologic pressure spike is not present, the pressure regulator 66' moves to an expanded or relaxed state. The compressed state of the pressure regulator 66' illustrated in FIG. 29C effectively creates more volume within the vasculature compared to the expanded state of the pressure regulator 66' illustrated in FIG. 29D. FIG. 29D illustrates a relatively low pressure condition, such as one corresponding to diastole.

Figure 29E:
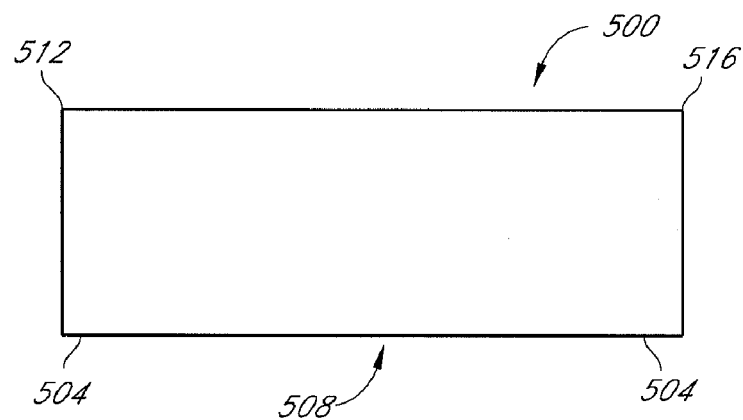
FIG. 29E is a schematic cross-sectional view of an attenuation device collapsed, in a compressed configuration, which can correspond to a relatively low pressure condition.
Figure 29F:
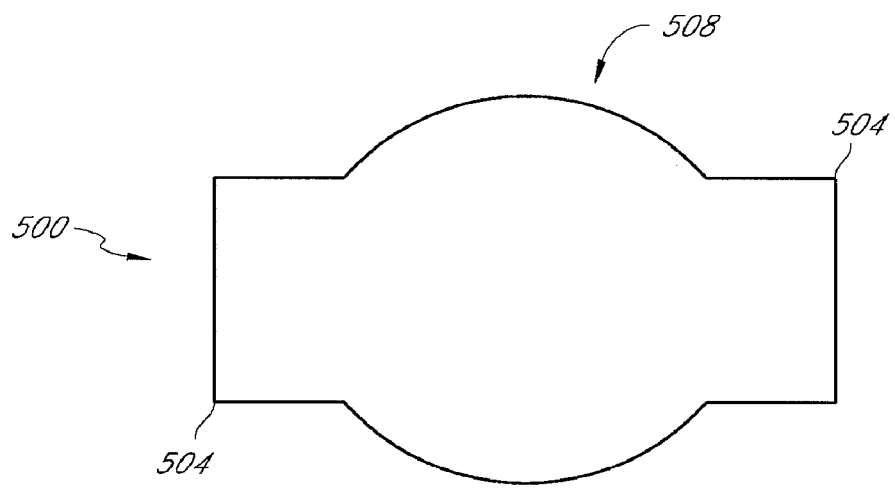
FIG. 29F is a schematic cross-sectional view of an attenuation device expanded to a configuration suitable for attenuating a pressure spike.
Figure 29G:
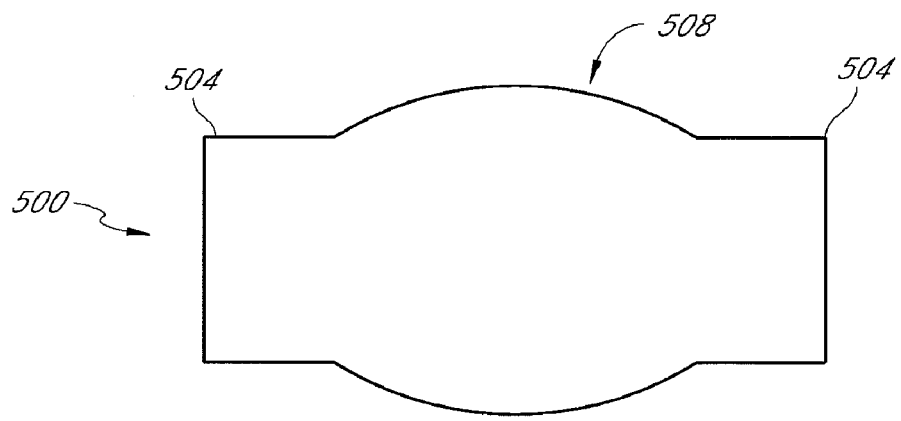
FIG. 29G is a schematic cross-sectional view of an attenuation device as it collapses to a compressed configuration after attenuating a pressure spike.

FIGS. 29E-29G show an implantable pressure regulator 500 that can be used to manage blood pressure spikes in a patient's vasculature. The pressure regulator 500 can be implanted outside the vasculature as well. The pressure regulator 500 can be configured as an elongate body, including a connection zone 504 disposed at least at one end thereof. Proximal and distal connection zones 504 can be disposed at each end, as shown in FIGS. 29E-G. The pressure regulator 500 can include at least one attenuation zone 508 to attenuate pressure spikes within a body lumen, such as a blood vessel. In the embodiment of FIGS. 29E-G, the pressure regulator 500 includes one attenuation zone 508 that is substantially tubular in nature, though other shapes are possible. The attenuation zone 508 can be located between a plurality of connection zones 504 where more than one connection zone is provided.

Any suitable material can be used to form part or all of the pressure regulator 500, e.g., ePTFE, polyethylene, silicone, PEEK, and other similar suitable polymeric materials. Preferably the pressure regulator 500, e.g., within the attenuation zone 508, is configured to be expandable in the range of pressures that can be generated in the patient. Such a configuration can be achieved by selecting a suitable material that is expandable under these pressures at a wall thickness that is suitable for vascular applications.

The attenuation zone 508 can be configured to expand to provide a greater cross-sectional area therein at a time when a relatively large pressure exists within the body portion, e.g., within a vessel. The amount of increase in cross-section area should be at least enough to attenuate pressure during a pressure spike to reduce the likelihood of or prevent a deleterious condition in the blood vessel or other body structure near to or remote from the pressure regulator 500. The attenuation zone 508 can be configured to provide a cross-sectional area that is at least about 5% larger during a relatively high pressure (such as one above an activation pressure) than the cross-section of the resting attenuation zone 508 at STP. In another embodiment, the attenuation zone 508 can be configured to provide a cross-section that is at least about 10% larger during a relatively high pressure (such as one above an activation pressure) than the cross-section of the attenuation zone 508 at the resting pressure. In another embodiment, the attenuation zone 508 can be configured to provide a cross-section that is at least about 20% larger during a relatively high pressure (such as one above an activation pressure) than the cross-section of the unexpanded attenuation zone 508.

The attenuation zone 508 can be configured to expand from a first, resting volume to a second, expanded volume to provide a greater volume for carrying blood across its length at a time when a relatively large pressure exists within the body portion, e.g., within a vessel. The amount of increase in blood carrying capacity should be at least enough to attenuate pressure during a pressure spike to reduce the likelihood of or prevent a deleterious condition in the blood vessel or other body structure. The attenuation zone 508 can be configured to provide at least about 105% of the resting state blood carrying volume during a relatively high pressure (such as one above an activation pressure). In another embodiment, the attenuation zone 508 can be configured to provide at least about 110% of the resting state blood carrying volume during a relatively high pressure (such as one above an activation pressure). In another embodiment, the attenuation zone 508 can be configured to provide at least about 120% of the resting state blood carrying volume during a relatively high pressure spike.

In the embodiment of FIGS. 29E-29G, a first connection zone 504 is provided on a first end 512 of the pressure regulator 500 and a second connection zone 504 is provided on a second end 516 of the pressure regulator. The attenuation zone 508 can be substantially tubular, e.g., having a substantially circular cross-section along at least a portion thereof. At least the attenuation zone 508 of the pressure regulator 500 can include a compliant material that enables the attenuation zone to move between first and second states, as discussed above. Movement from a first state corresponding to a pressure below a predetermined threshold, which is illustrated in FIG. 29E, to a second state corresponding to a pressure above the threshold, which is illustrated in FIG. 29F, can be provided by expansion of the pressure attenuator 500 within the attenuation zone 508. The first state of FIG. 29E can correspond to the end of diastole, just prior to systole and the second state of FIG. 29F can correspond to systole, for example.

At least the attenuation zone 508 of the pressure regulator 500 can comprise a compliant material such as silicone, latex or other elastomer, or composite structure that exhibits elastic properties. The compliant material can be one that responds to a reduction in pressure after a pressure spike by moving from an expanded state, such as the second state, as illustrated in FIG. 29F, to an un-expanded state, as illustrated in FIG. 29E.

Figure 29H:
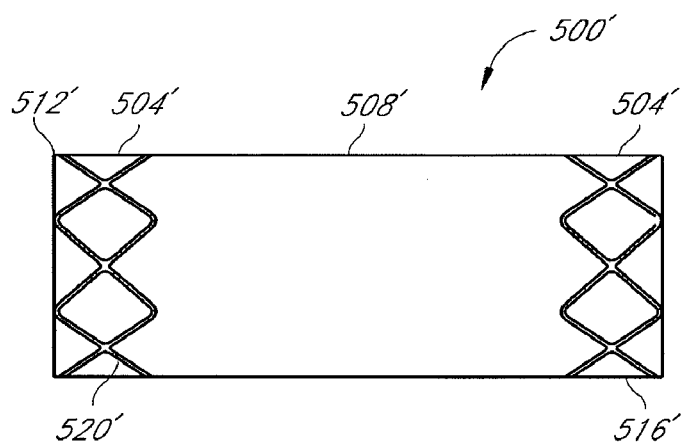
FIG. 29H is a schematic cross-sectional view of an attenuation device mounted to an expandable/collapsible attachment structure.
Figure 29I:
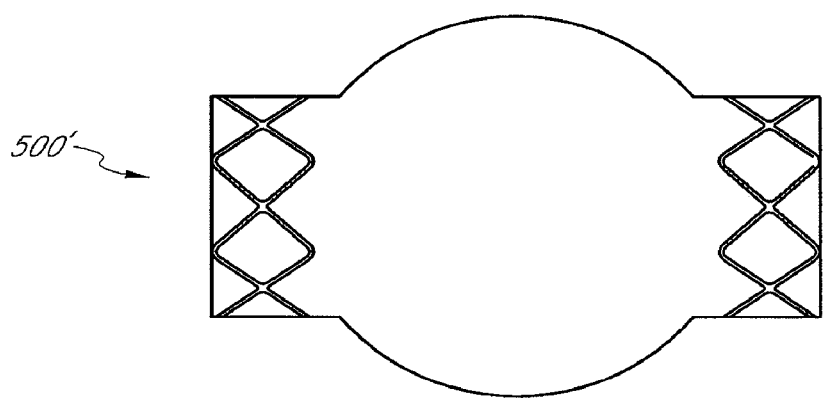
FIG. 29I is a schematic cross-sectional view of an attenuation device mounted to an expandable/collapsible attachment structure, the device being in an expanded configuration.
Figure 29J:
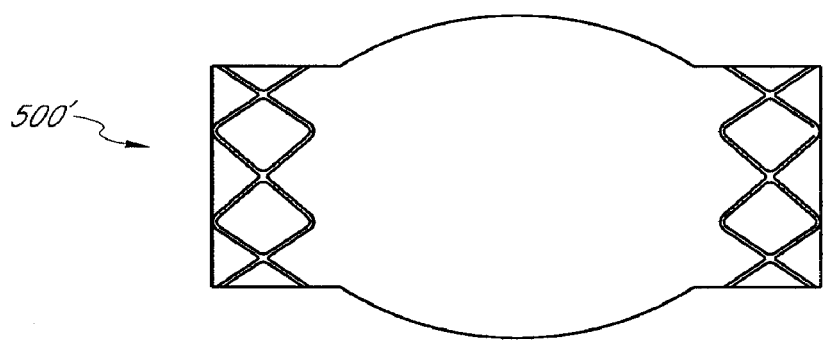
FIG. 29J is a schematic cross-sectional view of a, attenuation device mounted to an expandable/collapsible attachment structure, as it returns to a compressed configuration.

FIGS. 29H-J illustrate a pressure regulator 500' that is similar to the regulator 500 except as described differently hereinbelow. The regulator 500' can be a tubular attenuation device that includes a compliant attenuation zone. The regulator 500' includes at least one connection zone 504'. For an in line configuration, a connection zone 504' is provided on each end of the regulator 500'. The connection zone 504' can be configured with an engagement feature 520' that can be brought into engagement with portions of a body conduit, e.g., a blood vessel to secure the regulator 500' to the vessel. The engagement feature 520' is an expandable structure in one arrangement. For example, the engagement feature 520' can be a self expandable or balloon expandable stent or similar support frame that can be expanded to bring the connection zone(s) into engagement with an inner surface of a blood vessel. In one arrangement, the engagement feature 520' is disposed on an inside surface of a compliant tubular member that extends between first and second ends 512', 516' of the pressure regulator 500'. The engagement feature 520' can be an expandable and collapsible means in some embodiments such that the pressure regulator 500' can be applied and removed from the patient as needed. The response of the device 500' to pressure variations within a blood vessel is similar to that described above in connection with the regulator 500.

Figure 29K:
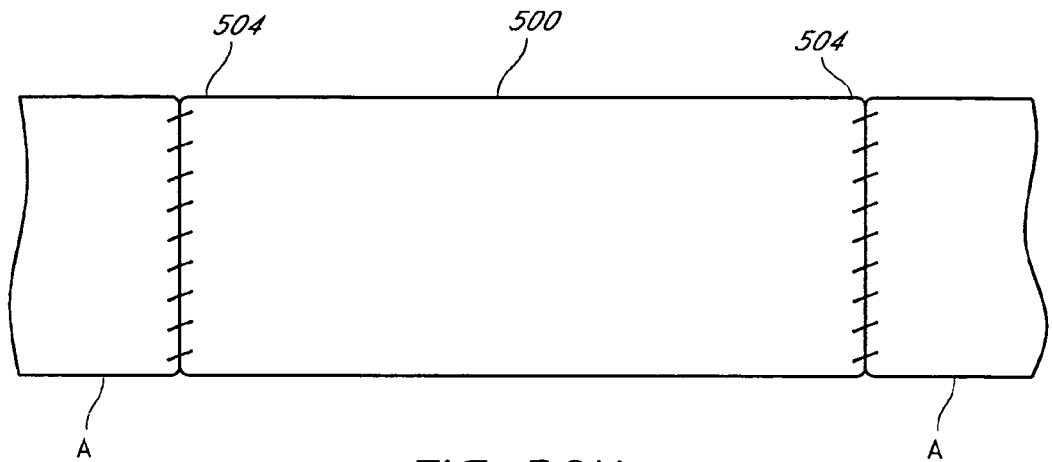
FIG. 29K is a schematic cross-sectional view through a vessel, illustrating an attenuation device anastamosed in series in the vessel.

FIG. 29K illustrate that the pressure regulators described herein, e.g., the pressure regulator 500 can be spliced into a blood vessel. It can be spliced in using any method including but not limited to suturing. For example, sutures can be threaded through the connection zone(s) 504 at one or both ends of the regulator 500 and through portions of a blood vessel A into which the regulator is inserted, in accordance with vascular anastomosis techniques that are understood in the art.

Figure 29L:
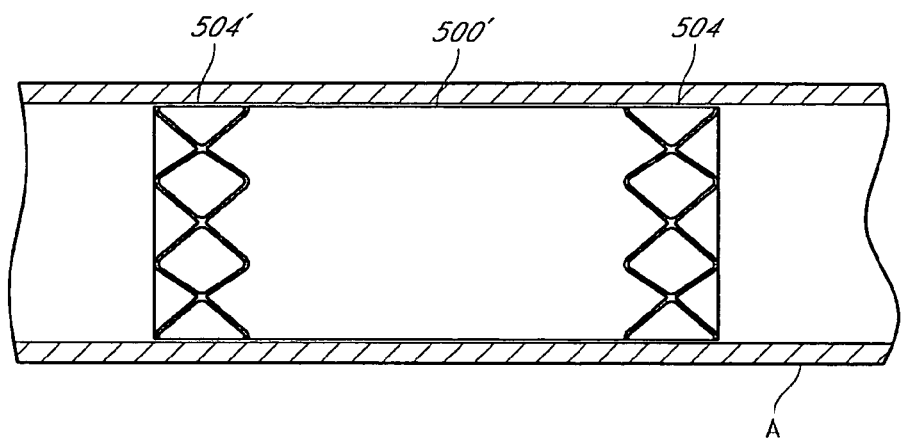
FIG. 29L is a schematic cross-sectional view through a vessel, illustrating an attenuation device mounted to an expandable support deployed within a vessel.

FIG. 29L depicts the pressure regulator 500' deployed in a vessel A. The pressure regulator 500' includes an expandable/collapsible means, such as that depicted in FIGS. 29H-J, for mounting in the vessel A. The connection zone(s) 504' can be expanded into engagement with an interior wall of the vessel A. This technique is beneficial in that a vascular segment need not be removed, as would be likely in a splice. This technique can be used where the portion of the vessel A remains relatively compliant and thus the attenuation zone 508' can expand to regulate physiologic pressure spikes.

Figure 29M:
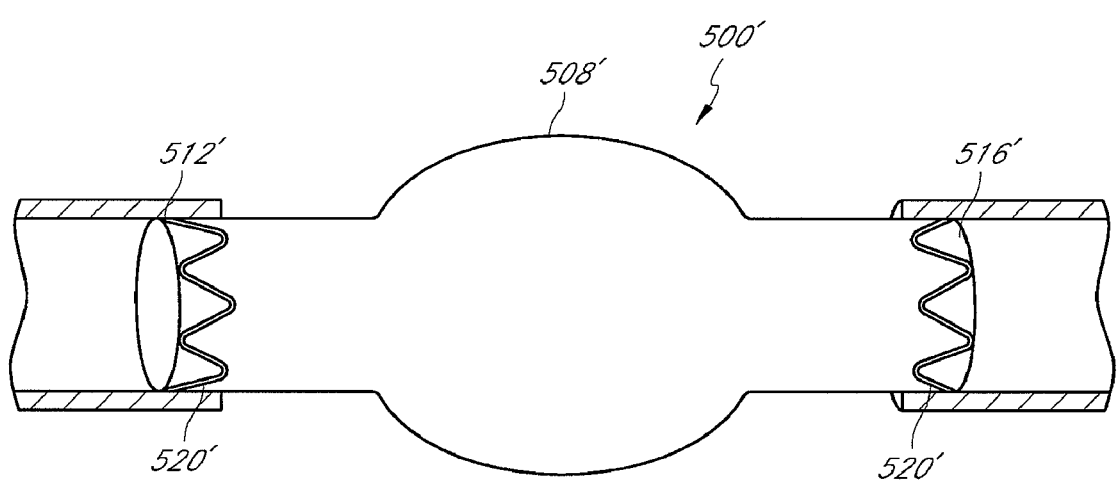
FIG. 29M is a schematic cross-sectional view through a vessel, illustrating a pressure regulator replacing a removed portion of a blood vessel.

FIG. 29M shows the pressure regulator 500' with upstream and downstream anastamotic connections for replacing a portion of a blood vessel A that has been removed. The blood vessel portion can be severed and/or removed using any suitable technique. Thereafter, the first end 512' can be inserted into an upstream portion of the vasculature and the second end 516' can be inserted into a downstream portion of the vasculature. After the first and second ends 512', 516' have been inserted, the engagement features 520' can be expanded to bring the ends of the pressure regulator into engagement with an inside surface of upstream and downstream portions of the vasculature. The anastomosis may be augmented with structures, adhesives or other techniques as desired. In the illustration, the attenuation zone 508' is shown in an expanded state, which can be induced by increased pressure, as discussed above.

Figure 29N:
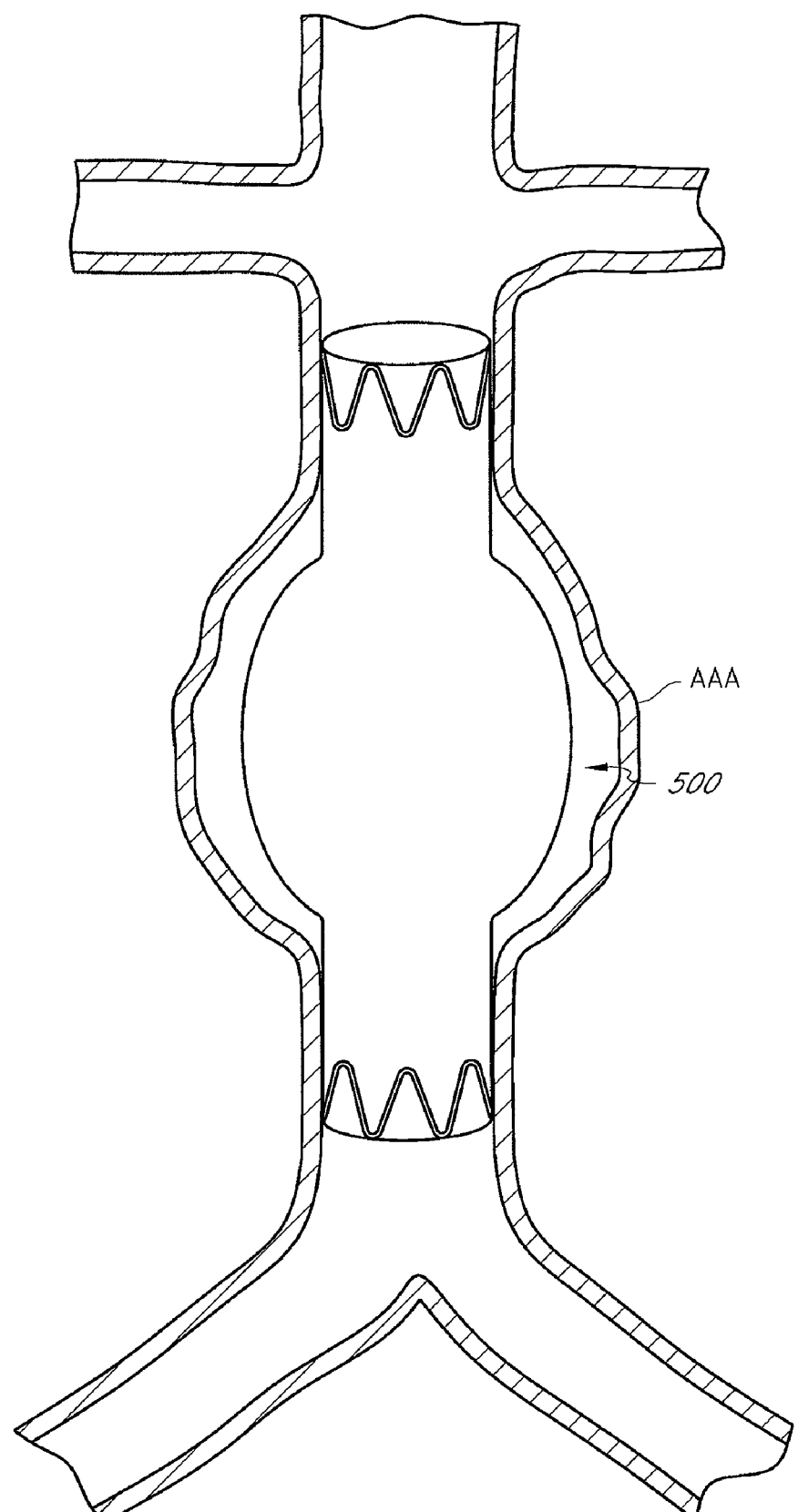
FIG. 29N is a schematic cross-sectional view through a vessel, illustrating a pressure regulator deployed within an abdominal aortic aneurysm.

FIG. 29N is a schematic cross-sectional view through a vessel, illustrating the pressure regulator 500' deployed within an abdominal aortic aneurysm AAA. The enlarged aneurysmal sac of the vessel provides a space into which the attenuation zone 508' can expand to attenuate pressure. The pressure regulator 500' can be deployed in other types of aneurysms as well and other vascular structures where sufficient space or vascular compliance is present to allow the attenuation zone 508' to expand and contract.

Figure 30A:
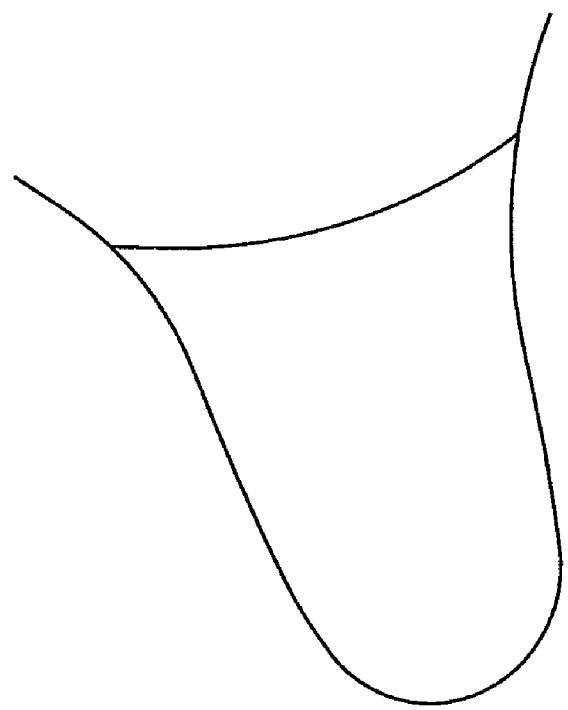
FIG. 30A is a schematic cross-section of a left atrial appendage of the heart, having an attenuation device positioned therein.
Figure 30B:
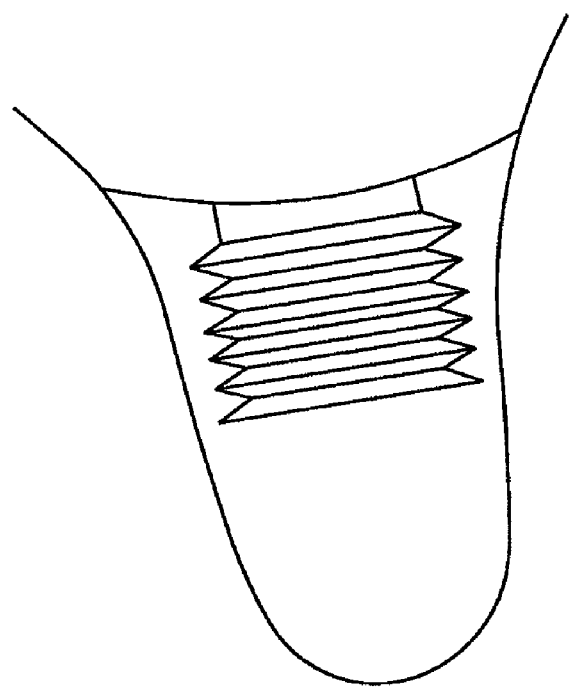
FIG. 30B is a schematic cross-section as in 30A, showing a bellows-type attenuation device positioned in the left atrial appendage.

An attenuation device or pressure regulator, such as those described herein, can be placed within the heart, such as in or on a wall of the heart, within a major artery, or within the left atrial appendage of the heart (see FIGS. 30A and 30B). Such placement can facilitate reduction in risk of a cardiovascular malady including, but not limited to renal failure, stroke, heart attack, blindness. With reference to FIG. 30A, in one embodiment, an air cell attenuation device 66 is positioned in the left atrial appendage of the heart. With reference to FIG. 30B, in one embodiment, a bellows-type attenuation device 66 is positioned in the left atrial appendage.

An attenuation device can be placed on or within the right side of the heart or in a pulmonary artery to reduce symptoms of primary permanent hypertension. An attenuation device can also be placed on the venous side of the vasculature system, such as within the wall of the vena cava or attached to a Greenfield filter within the vena cava to prevent portal hypertension and/or esophageal varicies. An attenuation device, such as an air cell, can be attached to or encompass a stent for placement within the vasculature.

Figure 31:
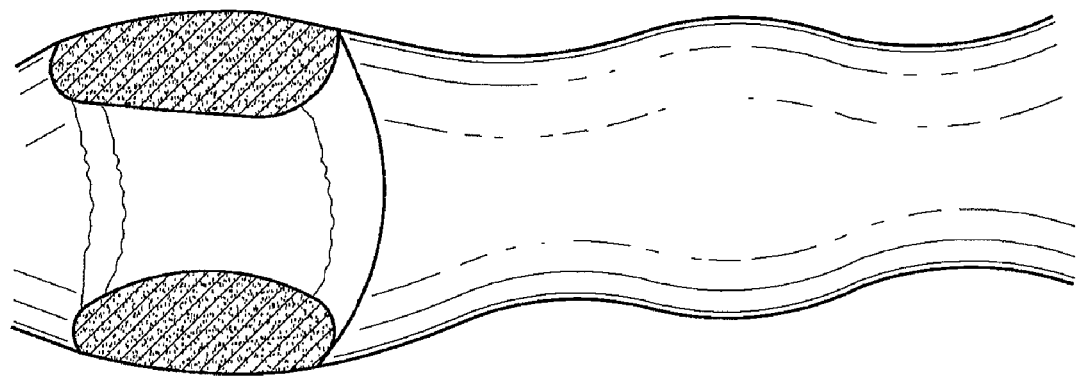
FIG. 31 is a schematic cross-section of a tubular attenuation device positioned within the colon.

In another embodiment, the attenuation device can be used in the gall bladder to modulate pressure contained therein. Pressure in the gall bladder may lead to undesired events such as the formation of stones or pain for the patient. An attenuation device can also be placed in the esophagus on the end of an NG tube to limit spasm. With reference to FIG. 31, an attenuation device 66 can be placed in the bowel 364 to treat irritable bowel syndrome, minimize Crons disease, cramping, or any other disorder resulting from peristalsis.

In another embodiment, the attenuation device is used in the field of ophthalmology to support cranio-facial tissue during healing after a traumatic event or intraoptically as therapy for acute angle closure glaucoma. In yet another embodiment, the attenuation device is used in the field of orthopedics as an implantable or external system to protect against pressure waves and control the location of a healing bone after a traumatic event. In still another embodiment, the attenuation device is used in the field of otorhinolaryngology for the management of pressure waves in the sinus cavities, including in and around the ears, the nose and the throat. In another embodiment, an attenuation device is placed in the lung to treat disorders such as, for example, asthma, bronchio spasms or prevent damage from coughing in fragile lung tissues in emphysema sufferers, etc. In yet still another embodiment, an attenuation device is used to prevent Central Nervous System ("CNS") problems such as, for example, head trauma, cerebral edema, hydrocephalus, etc. Here, the attenuation device can be placed in the epidural pocket under the skull.

In accordance with one aspect of the present invention, there are provided air cell-like attenuation devices that are placed in the bladder and/or other organs of the body and filled with or comprise one or more compressible substances to provide pressure compensation. Additionally, active, programmable pressure compensators or generators are envisioned to monitor pressure events, respond in a predetermined fashion, and record or transmit that information outside the body. Additionally, a reliable, maintenance-free therapeutic delivery system is described to programmatically release or distribute an agent into an organ of the body using an erodable or deformable support matrix or material of construction, and/or a programmable or responsive valving system.

Figure 36:
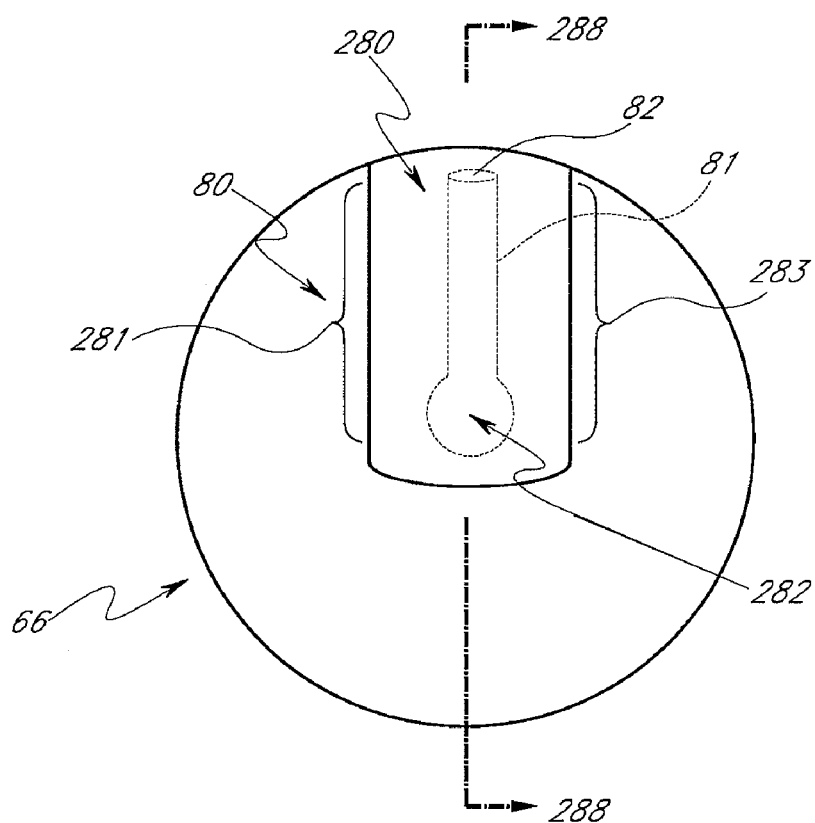
FIG. 36 is a schematic top plan view of an inflatable attenuation device with a valve that prevents the influx and/or efflux of media to from the attenuation device.
Figure 37:
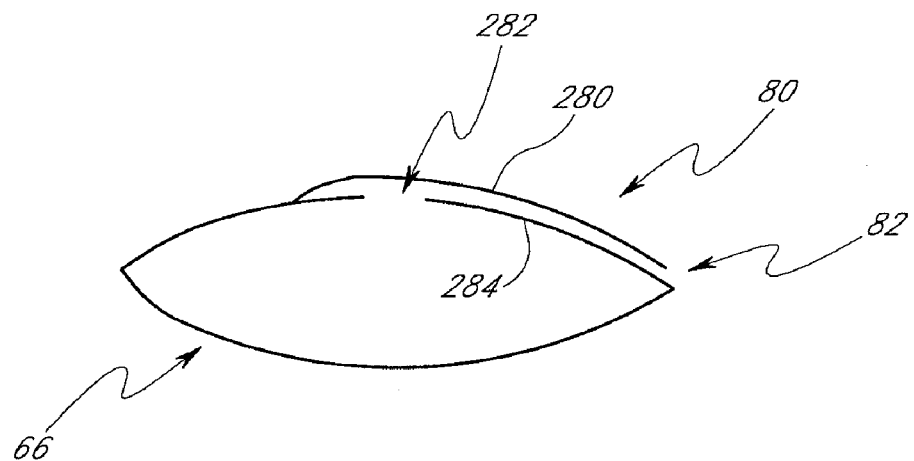
FIG. 37 is a cross-section through the line 288-288 in FIG. 36.

In accordance with one aspect of the present invention, there is provided a compressible attenuation device having a valve that permits filling of the attenuation device through a filling device and yet resists deflation and/or additional filling of the attenuation device after the filling device is removed. In one embodiment, illustrated in FIGS. 36 and 37, the valve 80 is formed by two parallel welds 281, 283 at the interface between two complimentary surfaces—namely, the outer cover 280 and the underlying layer 284. The valve 80 is in effect a collapsible airflow passageway that remains in the collapsed position when the filling device is removed, thereby preventing deflation when the pressure within the attenuation device 66 is greater than the pressure immediately outside the attenuation device and preventing the additional filling of the attenuation device 66 when external pressure is greater than the pressure within the attenuation device 66. The outer cover 280 and the underlying layer 284 function as two flat sheets that stick together regardless of the relationship between the internal attenuation device pressure and the immediate external pressure. In one embodiment (not shown), one or more adhesive materials or general locking mechanisms known in the art of medical device design can be used to shut the value 80 upon removal of the filling device. It should be noted that once the filling device enters the valve at the entry point 82, the attenuation device can be released and/or filled at any point inside of the entry point 82, including but not limited to the interface 282 between the valve 80 and the inside of the attenuation device 66. The valve of the present embodiment can be constructed according to the disclosure provided by U.S. Pat. No. 5,144,708, titled check valve for fluid bladders, issued Sep. 8, 1992, the disclosure of which is incorporated in its entirety herein by reference.

Figure 38:
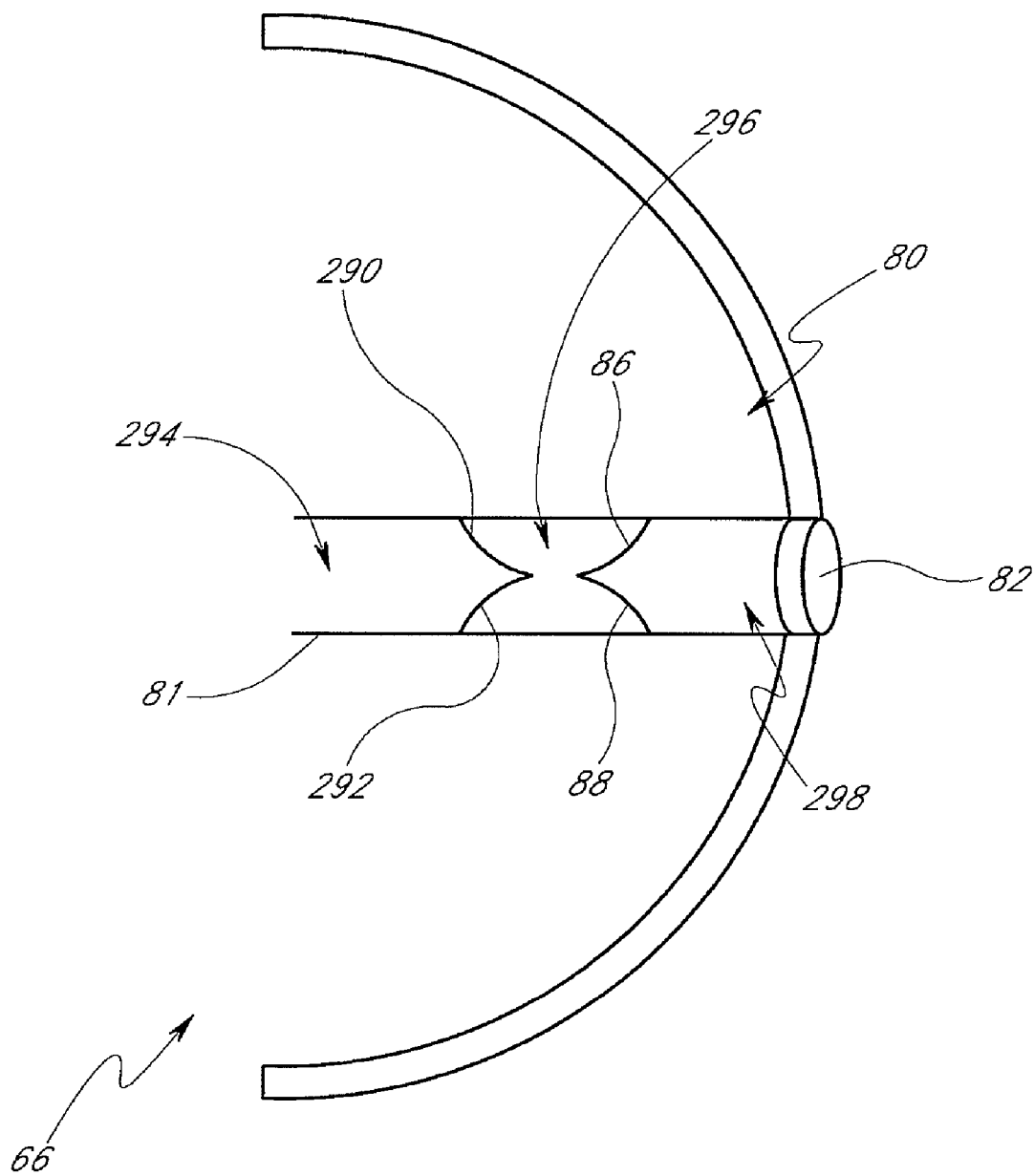
FIG. 38 is a schematic top plan view of a valve with two duckbill structures that prevent the flow of media in both directions.

In another embodiment, illustrated in FIG. 38, the valve 80 includes two duckbill structures that face opposite each other, thereby permitting filling of the attenuation device through a filling device while resisting deflation and/or additional filling of the attenuation device after the filling device is removed. The valve 80 generally comprises a tubular wall 81, having an aperture 82 in communication with a flow path 298. The valve has two sets of first and a second duck bill valve leaflets 86, 88, 290, 292 that are attached to the tubular wall 81. Upon removal of the inflation media source, the inflation media within attenuation device 66 in combination with natural bias of the leaflets 86 and 88 cause the leaflets to coapt, thereby preventing effluent flow of inflation media through the flow path 83. In addition, the natural bias of the leaflets 290 and 292 cause the leaflets to coapt, thereby preventing the additional influx of media. It should be noted that the internal section 294 of the tube will have a pressure equal to the internal pressure of the attenuation device, whereas the external portion or flow path 298 will have a pressure equal to the immediate external pressure. A middle or neutral section 296 of the tube is defined by the tubular wall and the two oppositely facing duckbill structures defined by leaflets 86, 88, 290, 292.

In accordance with another aspect of the present invention, there is provided an implantable self-inflating pressure attenuation device that can inflate from a first, deflated configuration to a second, at least partially inflated configuration. Various transformable mediums can be used to inflate the housing of the attenuation device from a deflated configuration to at least a partially inflated configuration.

Figure 47A:
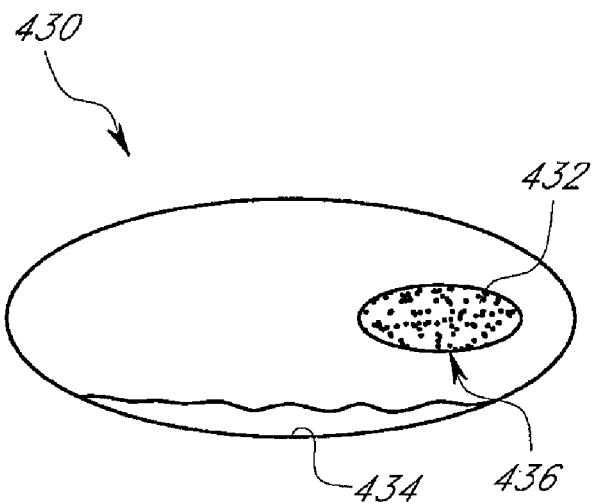
FIG. 47A is a schematic cross-sectional view through one embodiment of an implantable self-inflating attenuation device.
Figure 47B:
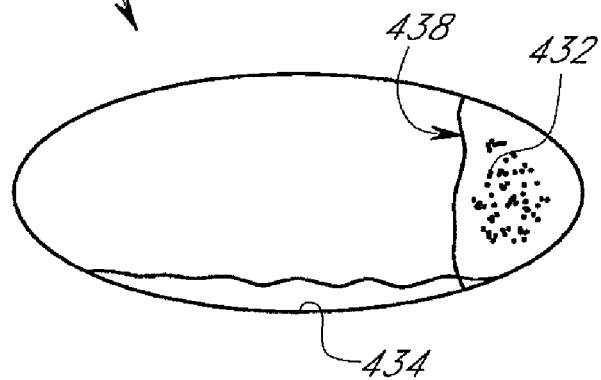
FIG. 47B is a schematic cross-sectional view through one embodiment of an implantable self-inflating attenuation device.
Figure 47C:
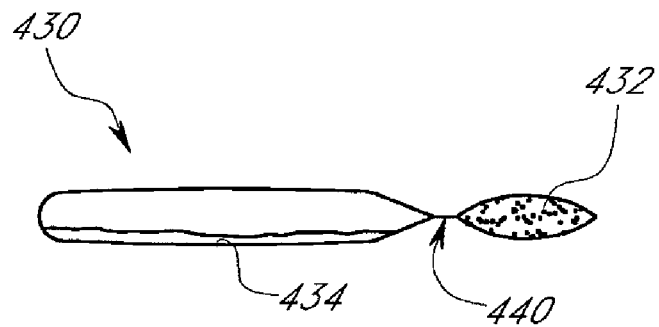
FIG. 47C is a schematic cross-sectional view through one embodiment of an implantable self-inflating attenuation device.
Figure 48A:
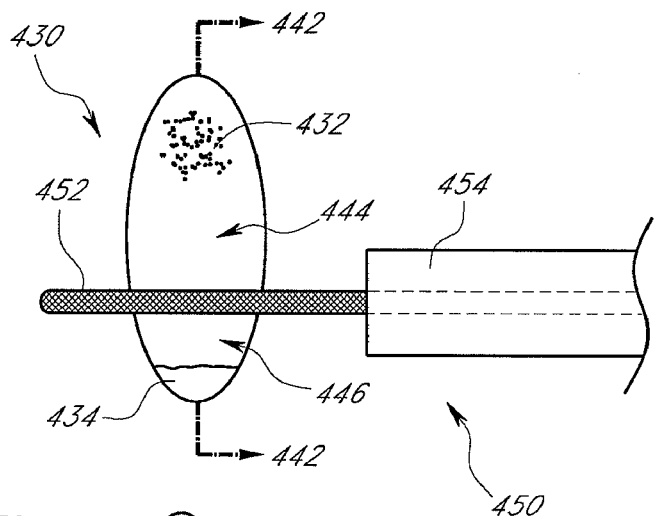
FIG. 48A is side elevational schematic view of a delivery system for deploying an implantable self-inflating attenuation device in accordance with one aspect of the present invention.
Figure 48B:
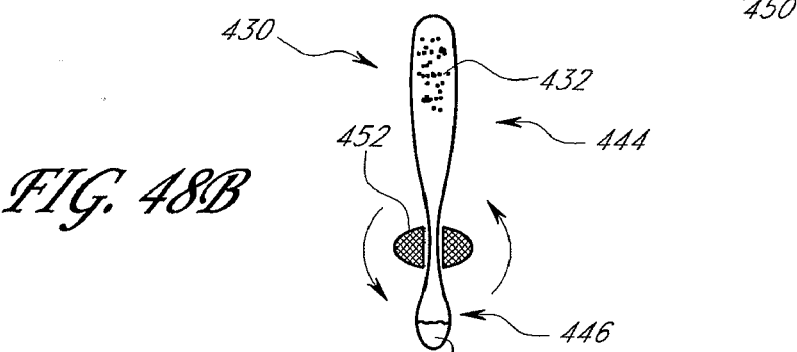
FIG. 48B is a cross-section through the line 442-442 in FIG. 48A.
Figure 48C:
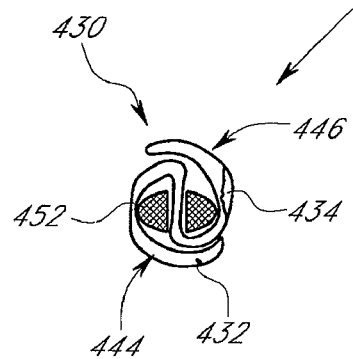
FIG. 48C is a schematic cross-sectional view through one embodiment of an implantable self-inflating attenuation device.
Figure 48D:
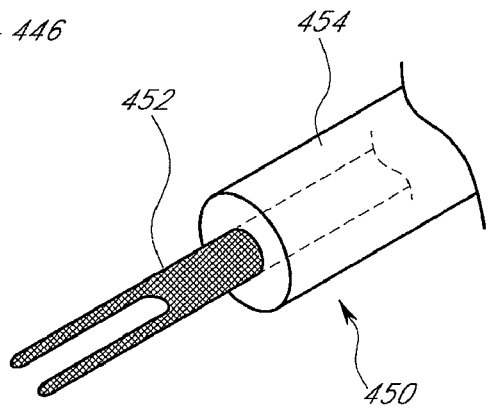
FIG. 48D is an elevated schematic view of a delivery system for deploying an implantable self-inflating attenuation device in accordance with one aspect of the present invention.

With reference to FIGS. 47A-47C, in one embodiment, the transformable medium comprises a first reactant 432 and a second reactant 434. Here, the implantable self-inflating pressure attenuation device 430 (shown in its first, deflated configuration) generally comprises a first reactant 432 and a second reactant 434, which are physically separated from each other. When the first reactant 432 comes into contact the second reactant 434, a chemical reaction occurs within the attenuation device 430, thereby causing the device attenuation 430 to transform into at least a partially inflated configuration (not illustrated).

With reference to FIG. 47A, in one embodiment, the first reactant 432 is contained within a balloon or container 436 that is entirely contained within and free to move within the attenuation device 430. The container 436 is generally impermeable to reactants 432, 434, and can comprise any suitable material known to those skilled in the art. The suitability of a material for the container 436 will depend on the chemical characteristics of the reactants 432, 434. In another embodiment, illustrated in FIG. 47B, the reactants 432, 434 are compartmentalized and separated within the attenuation device 430 by a wall 438. The wall 438 is generally impermeable to reactants 432, 434, and can comprise any suitable material known to those skilled in the art. The suitability of a material for the wall 438 will depend on the chemical characteristics of the reactants 432, 434. In yet another embodiment, shown in FIG. 47C, the attenuation device 430 has a crease 440. The crease 440 separates the reactants 432, 434, and thereby prevents the inflation/expansion reaction from occurring until such inflation/expansion is desired and triggered by the user. In still another embodiment (not illustrated), the reactants 432, 434 are separated within the attenuation device 430 by a peelable bond, fold, and/or the like, known to those skilled in the art.

In one embodiment, the medium capable of transformation comprises gas generating compositions. Various compositions can be used to generate gas in accordance with this invention. One class of compositions is the combination of a base and an acid to produce carbon dioxide. The acid and base are combined in dry form and rendered reactive only when co-dissolved in water. Examples of suitable bases are water-soluble carbonate and bicarbonate salts, nonlimiting examples of which are sodium bicarbonate, heat treated sodium bicarbonate, sodium carbonate, magnesium carbonate, potassium carbonate, and ammonium carbonate. Non-limiting examples of suitable acids are citric acid, tartaric acid, acetic acid, and fumaric acid. One presently preferred composition is a dry mixture of sodium bicarbonate and citric acid. Compositions containing more than one acid component or base component can also be used.

Gas generation can be initiated various ways, such as, for example, contact with a fluid, temperature change, ignition, pH change, etc. In one embodiment, the amount of gas generated is equal to the amount of volume dissipated through the air cell, thereby allowing for constant volume device until the gas generating materials are exhausted.

The amount and rate of gas production can be controlled by certain factors, such as, for example, the amount of reactive materials or reactants, the amount of gas entrapped in the structure, or the solubility of one or both of the chemicals in water, etc. In one embodiment comprising a wick and tablet systems, the available water as delivered by the wick to the tablet dissolves only a limited amount of the reactants and resulting reaction product(s). The reaction is thus limited by the solubility of the chemicals in the limited amount of available water. The rate of water delivery thereby controls the reaction rate. Some examples of the solubility of suitable reaction chemicals per 100 grams of water are as follows: sodium bicarbonate, about 10 g; citric acid, about 200 g;

tartaric acid, about 20 g; and fumaric acid, about 0.7 g. The limited solubility and limited water delivery rate through the wick make it unnecessary to keep the acid and base separated either before or during use of the infusion device.

It is further understood that a catalyst, another chemical species or one of the byproducts of the reaction can propagate the reaction and increase its speed. In the case of sodium bicarbonate and citric acid, the byproducts are carbon dioxide, sodium citrate, and water. A very small amount of water, such as, for example, 0.1 to 0.5 ml, can be used to start the reaction by dissolving the sodium carbonate and citric acid. Since water is produced in the reaction, the reaction speed increases until all of the reactants are exhausted.

As a manufacturing aid, it may be desirable to add inert agent(s) to the reactant composition to aid in the tableting process and to keep the tablet intact during and after use. Examples of suitable tableting aids include but are not limited to polyvinyl pyrrolidone and anhydrous dibasic calcium phosphate, sold by Edward Medell Co. (Patterson, N.J., USA) as EMCOMPRESS.RTM. Tableting aids can be eliminated for certain compositions with no loss of performance. One such composition is the mixture of sodium bicarbonate and citric acid.

Chemical compositions that produce oxygen or other gases can also be used. A composition to generate oxygen in the presence of water is disclosed in U.S. Pat. No. 4,405,486, titled Method for Preparing granulated perborate salts containing a polymeric fluorocarbon, issued Sep. 20, 1983, the disclosure of which is incorporated in its entirety herein by reference. The controlled rate of wicking water into such a tablet, and the limited solubility of the constituents can control the rate of oxygen release in a manner similar to that of carbon dioxide in the systems described above.

In another embodiment, the medium capable of transformation comprises peroxide and/or superoxide chemical systems. In certain embodiments, gas is generated by drawing an aqueous solution of a peroxide or superoxide into an absorbent tablet that contains an enzyme or catalyst which promotes the decomposition of the peroxide or superoxide to decomposition products including oxygen gas. In another embodiment, a solid peroxide or superoxide can be incorporated into the tablet, with oxygen generation being initiated by contact of the peroxide or superoxide with water. Hydrogen peroxide, for example, decomposes into water and oxygen, providing no hazardous reaction products after infusion of the liquid has been completed. Metal peroxides, such as, for example, lithium peroxide, sodium peroxide, magnesium peroxide, calcium peroxide, and zinc peroxide, etc., react with water to produce the metal hydroxide and hydrogen peroxide, which then decomposes into water and oxygen. Superoxides, such as, for example, sodium superoxide, potassium superoxide, rubidium superoxide, cesium superoxide, calcium superoxide, tetramethylammonium superoxide, etc., react with water to produce the metal hydroxide and oxygen gas directly. It will be noted that the production of hydrogen peroxide itself is particularly preferred.

In one embodiment, a suitable tablet contains a water absorbent material to facilitate the wicking action, and the enzyme or catalyst in systems where enzymes or catalysts are used. Examples of water absorbents useful for this purpose include superabsorbent polymers, reconstituted cellulosic materials, compressed zeolite powder (Types 13X and 4A, both unactivated), etc.

One example of a suitable enzyme is catalase. Lyophilized catalases are generally preferred. Catalysts effective for the decomposition include metals deposited on high surface area substrates, such as, for example, alumina, activated carbon, etc. Examples of suitable catalysts include platinum, palladium, silver, etc.

Chemical reactants can also be used rather than enzymes or catalysts to decompose hydrogen peroxide. Examples of such reactants include but are not limited to potassium permanganate, sodium hydroxide, etc. It should be noted, however, that there are safety concerns associated with potassium permanganate and sodium hydroxide.

As between enzymes and catalysts, enzymes provide a cost benefit for single-use systems. For reusable systems, however, catalysts are generally preferred. One significant advantage to the use of a hydrogen peroxide system with a catalyst is the ability to regenerate the system by drying out the tablet and adding more hydrogen peroxide solution to the water reservoir. Regeneration in this type of system is thus easier than regeneration of an absorbent tablet for a system that requires adsorbed gas.

In another embodiment, the medium capable of transformation comprises chemical reactants that are used effectively to generate a gas to push a fluid from an infusion pump. In order to generate carbon dioxide, two or more reactive chemicals are mixed that, upon reaction, generate a gas. Preferably, one of the reactants is provided in liquid form, i.e., a liquid chemical, a solution, or the like, and another one of the reactants is provided as a solid. Either the liquid or the solid may comprise more than one reactive chemical. However, in one preferred embodiment, each of the liquid and the solid contain only one reactive species.

Carbon dioxide is generally quite inert and safe at low concentrations. However, other gases could also be used, provided they are relatively inert and safe. For the purposes of the following discussion, it will be assumed that carbon dioxide is to be generated. As mentioned above, to generate the gas, at least two reactants are caused to come into contact. For ease of reference, the reactants will be referred to herein as a first reactant and a second reactant or a solid reactant and a liquid reactant, and particular sets of reactants will be referred to as reactant sets.

First Reactant: Preferably, the first reactant is selected from a group consisting of carbonates and bicarbonates, particularly, Group I and II metal carbonates and bicarbonates (the "carbonate"). For example, in one embodiment, preferred carbonates include sodium bicarbonate, sodium carbonate, magnesium carbonate, and calcium carbonate. However, sodium bicarbonate, sodium carbonate and calcium carbonate are highly preferred, with sodium carbonate (or soda ash) being the most highly preferred. One desirable feature of sodium carbonate is that it is easily sterilizable. For example, sodium carbonate can be sterilized with heat, such as through autoclaving. This is preferable, since the infusion devices for use with the invention are designed for human use and it is safer to ensure that all of the components are sterile whether it is expected that they will come into contact with the patient or not. Other reactants that are sterilizable with heat, ethylene exposure, or exposure to ionizing radiation are equally useful.

The carbonate can be either used as a solid reactant or can be dissolved in a solution to form a liquid reactant. In one preferred embodiment, the carbonate is used as a solid. The reason for this choice is that the carbonates are all solids and some are only sparingly soluble in water.

Second Reactant: The second reactant is preferably an acid. Preferably, the acid is selected from the group consisting of acids, acid anhydrides, and acid salts. Preferably, the second reactive chemical is citric acid, acetic acid, acetic anhydride, or sodium bisulfate. Usually the second reactant is used as the liquid reactant. However, in the case of citric acid and sodium bisulfate, for example, the second reactant can also be the solid reactant. Nevertheless, the second reactant is generally more soluble in water than the first reactant and is, therefore, used to form the liquid reactant.

Reactant Sets: A reactant set is based upon a variety of considerations. For example, the solubility of the first and second reactants are considered to determine which reactant should be used as the solid or liquid reactant. Also considered is the product of the reaction and its solubility. It is preferred that the products be $CO_2$ gas and a soluble inert compound. Once these factors are considered, appropriate reactant sets can be contructed. For instance, in one embodiment, reaction sets such as those shown in Table I are preferred.

TABLE I

| Solid Reactant | Liquid Reactant |
| --- | --- |
| Sodium Carbonate | Citric Acid |
| Calcium Carbonate | Acetic Acid |
| Magnesium Carbonate | Citric Acid |

Additional details may be found in U.S. Pat. No. 5,992,700, titled controlled gas generation for gas-driven infusion devices, issued Nov. 30, 1999, and U.S. Pat. No. 5,588,556, titled method for generating gas to deliver liquid from a container, issued Dec. 31, 1996. Both of these patents are hereby incorporated by reference herein and made a part of this specification.

In another embodiment, the method of producing gas is entrapped pressurized gas in a sugar or a porous molecular sieve. Generally, gas is liberated when the structure comes in contact with a fluid.

In accordance with another aspect of the present invention, there is provided a method of delivering the implantable self-inflating pressure attenuation device 430 into the treatment site, such as, for example, the bladder. With reference to FIGS. 48A-48D, in one embodiment, the delivery system 450 includes a bifurcated delivery tool 452 and a delivery cannula 454. The tool 452 has a fork-like shape and can be extended out and retracted into the cannula 454. As illustrated, the bifurcations of the tool 452 are spaced so as to squeeze or pinch the device 430, thereby separating a first portion 444 of the attenuation device 430 from a second portion 446, and thereby separating a first reactant 432 from a second reactant 434. Because the reactants 432, 434 do not come into contact with each other, the device remains in its deflated state, thereby facilitating the procedure of delivering the attenuation device 430 to the treatment site, such as, for example, the bladder. In one embodiment, shown in FIGS. 48B and 48C, first and second portions 444, 446 of the deflated attenuation device are wound about itself along the axis of the tool 452, thereby minimizing the volume of the attenuation device 430, and thereby facilitating the delivery of the attenuation device 430 into the treatment site.

In accordance with another aspect of the present invention, there is provided a method of improving the dynamic compliance and/or contractility of the bladder.

Figure 40A:
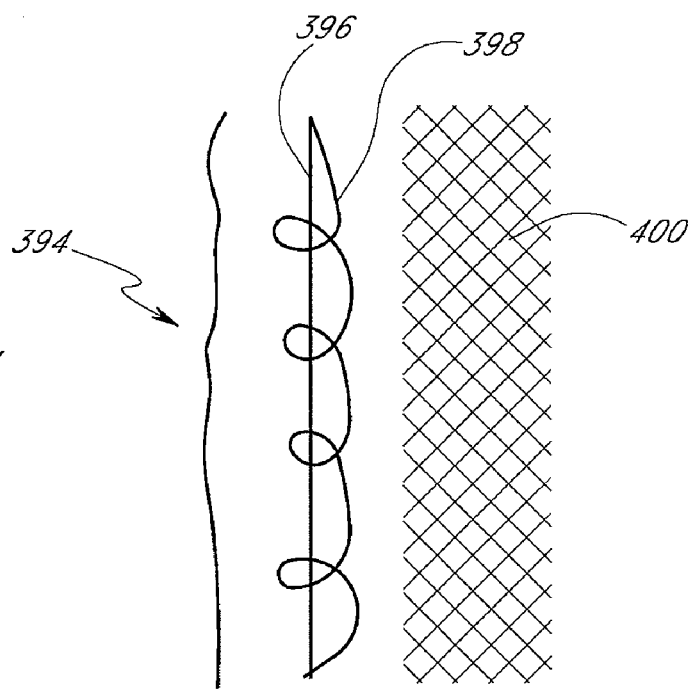
FIGS. 40A and 40B illustrate the connective and elastic tissues in the submucosal layer of the bladder.
Figure 40B:
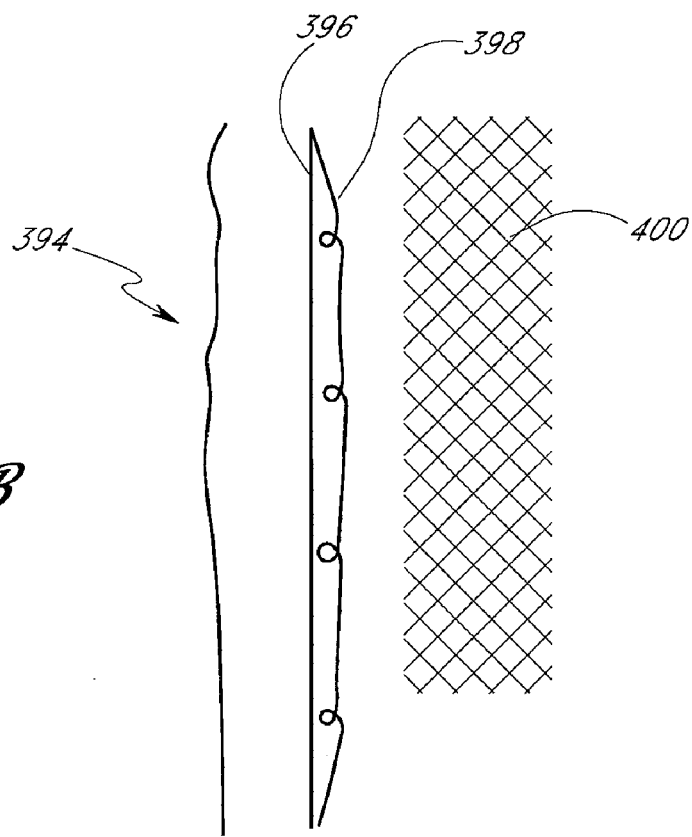

Histology: The muscoa of the bladder is composed of transitional epithelium. Beneath it is a well-developed submucosal layer formed largely of connective and elastic tissues. With reference to FIGS. 40A and 40B, the connective and elastic tissues of the bladder wall generally comprise mucosa 394, elastin 396, collagen 398, and muscle 400.

With reference to FIG. 40A, as in most tissues, collagen 398 is arranged as a coiled or complex helical material within the bladder wall. While collagen 398 itself is not very elastic (distensible), the coiled configuration allows expansion of the collagen bundle. When the bundle is extended (see FIG. 40B), the uncoiled collagen length becomes the limiting size. It is at this point that tension rises rapidly, analogous to the twisting of several strands of rope. When twisted, the combined strands shorten. The combined strands can be lengthened by untwisting without stretching any individual strand. As in other tissues, as the patient ages the elastin 396 converts to collagen 398, reducing the compliance of the bladder 63. External to the submucosa is the detrusor muscle 400, which is made up of a mixture of smooth muscle fibers arranged in a random, longitudinal, circular, and spiral manner.

Figure 41:
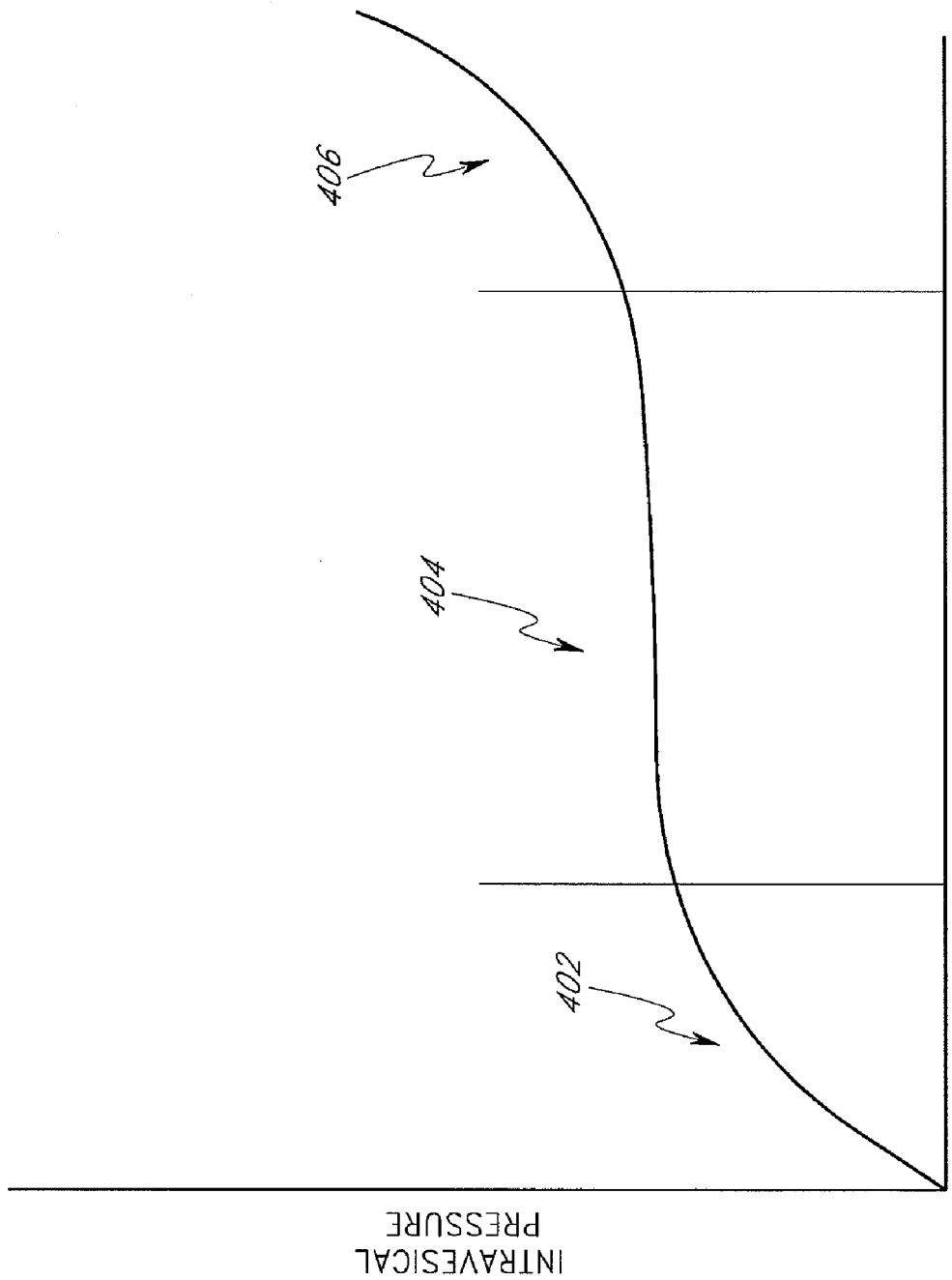
FIG. 41 shows a typical cystometrogram.

Physiology: The functioning of the bladder includes contributions from each of the layers of the bladder 63 described above. One method of understanding the properties of the bladder over time is to evaluate a cystometrogram, which, in one embodiment, is generated by reasonably slow continuous filling of the bladder 63. FIG. 41 illustrates a typical cystometrogram. Initially, during Phase I 402 when the bladder 63 is empty, elastic elements are not stretched. Here, the bladder is in a collapsed state and none of the materials within the wall are expanded. Accordingly, there will be no tension within the wall and pressure within the bladder will be relatively low. During Phase II 404, as fluid fills the bladder, the walls unfold and elastic structures start to stretch. Now there is some tension and bladder pressure rises. As the bladder continues to fill, and the elastic tension continues to increase, the radius increases as well. From the Law of Laplace for a sphere, ($P=2T/R$), it will be noted that in order for pressure to remain constant, the proportion between tension and radius must remain constant. During Phase III 406, as the bladder capacity is reached, collagen and/or other less elastic materials have become unfolded and are themselves subject to stress. Since their modulus of elasticity is less than that for elastin and for the other elements on stress up to this point, the wall tension rises quickly and bladder fluid pressure rises steeply. A slight increase in volume or radius will now produce a rapid change in pressure. As this stretch occurs, neurological factors apply as afferent impulses from the bladder in response to stretch begin to occur with a significant frequency.

Therapeutic Benefits, Methods of Improving the Dynamic Compliance of the Bladder, Methods of Improving the Contractility of the Bladder: Based on demonstrations by Solace, Inc. it is believed that the removal of high frequency, repetitious insults to the bladder wall for a 5 day to 180 day period of time increases the dynamic compliance of the bladder and reduces symptoms of incontinence by: precluding/reducing the stretch of elastin fibers; reducing of the conversion of elastin fibers into collagen; allowing the "stretched" muscles of the bladder wall to shorten, thereby improving compliance and bladder wall contractility; removing pressures exerted on the pelvic floor and connective tissues, allowing retraining and healing, increasing urethral resistance; placing the attenuation device in the bladder provides passive resistance to the bladder neck and bladder wall, allowing the muscles to strengthen. These and other therapeutic benefits could last up to about 30 days to about one year. One additional benefit of attenuation and/or improving bladder compliance includes improved flow during voiding (i.e. method of improving flow during voiding by "smoothing" the pressure within the bladder). Abdominal straining, resulting in a raised abdominal pressure $P_{abd}$ and, therefore, an increased intravesical pressure is not often employed in normal voiding, nor is it usually as efficient as detrusor contraction in producing voiding. If, however, the detrusor contraction is weak or absent abdominal straining may be the only available way of voiding and may then become of primary importance.

The detrusor pressure is not by itself a measure of the strength of the detrusor contraction. A satisfactorily contracting detrusor can produce either a high detrusor pressure and a low flow-rate, or a low pressure and a high flow-rate. The tradeoff between the pressure generated and the flow produced results from the force/velocity relationship characteristic of any contracting muscle. Consequently, for patients with low dynamic bladder compliance, any pressure changes during flow can significantly decrease flow rates. For patients that have weak detrusor contractions and/or those that "bear down" for force urine out of the bladder, sometimes referred to "Val Salva voiders," there is great pressure fluctuations within the bladder during voiding, resulting in reduced flow rates. By attenuating pressures within these patients via an attenuation device, improved flow can be achieved.

Another benefit of attenuation and/or improving bladder compliance includes improved urethral closure pressures. Changes in abdominal pressure affect not only the intravesical pressure but also the urethra, proximally by direct mechanical action. The result is that when the abdominal pressure rises, as during straining or a cough, the urethral pressure discussed above also rises. The maximum urethral closure pressure therefore does not diminish, and may even increase. This represents a natural defense against leakage during stress. This process is enhanced by the attenuation of intravesical pressures within the bladder, with full exposure of the urethra to increased abdominal pressures.

Another benefit of attenuation and/or improving bladder compliance includes improving the symptoms of benign prostatic hypertrophy ("BPH"). As the prostate enlarges, flow rates are reduced and residual volumes increase. The symptoms of low flow are increased as the increased intravesical pressure causes a decrease in the compliance of the bladder wall, bladder muscles elongate, elastin converts to collagen in the most severe cases), making it even more difficult for the bladder to "push" the urine through the restricted opening of the prostate. As this cascade continues, the symptoms of benign prostate hyperplasia increase. Placement of an attenuation device in the bladder reduces symptoms of BPH by improving flow, increasing the compliance of the bladder wall, removing high pressure insults to the bladder wall, and allowing the bladder wall muscles to shorten, all permitting the bladder to more effectively "push" the urine through the urethra and prostate. In one embodiment, the attenuation device in the bladder reduces the symptom of BPH by attenuating increases in pressure within the bladder by reversibly reducing its volume in response to the pressure increases. For example, in one embodiment, the attenuation device reduces its volume by at least 5%. In another embodiment, the attenuation device reduces its volume by at least 10%. In yet another embodiment, the attenuation device reduces its volume by at least 25%.

Figure 42:
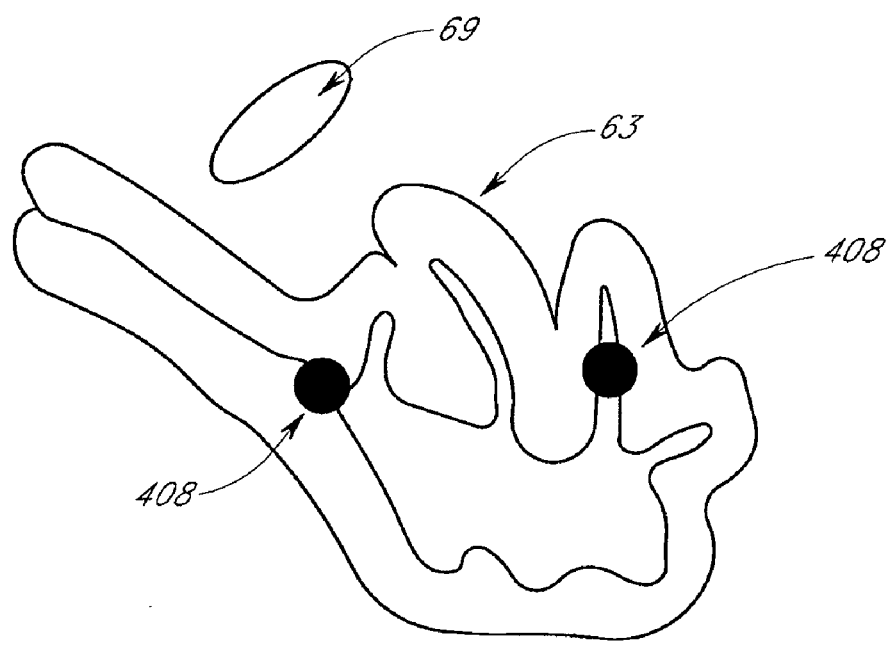
FIGS. 42 and 43 provide side elevational cross-sectional views of a partially collapsed bladder.

Conformable Device: Patients generally experience pain and irritation when any foreign object is either wholly or partially in the bladder or bladder neck. With reference to FIG. 42, this pain can occur when the bladder or bladder neck has collapsed onto the foreign object 408, perhaps within a fold of the bladder; the pressure exerted on the bladder wall by focal points on the device creates pain and irritation. This pain is typically more acute when the patient is in the horizontal position.

Figure 43:
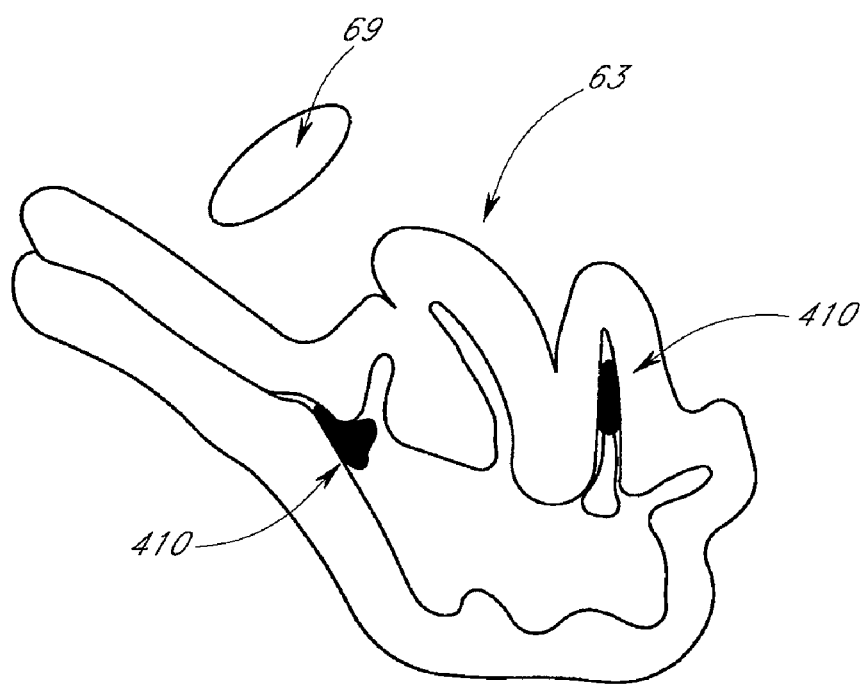

With reference to FIG. 43, to eliminate pain and irritation of the bladder and bladder neck when the bladder collapses on to any device (wholly or partially in the bladder and bladder neck), the shape of the attenuation device 410 can change to conform to the bladder wall in order to maximize the surface area of the attenuation device in contact with the bladder wall so as to dissipate the pressure over as large a surface area of the bladder wall as possible, and thereby prevent the focal points that cause trauma, pain, or irritation to the bladder. In one embodiment, the attenuation device has a compressible wall, thereby resulting in a conformable device where the medium (e.g., gas) within the device can move out of a fold in the bladder wall to reduce trauma. Examples of such attenuation devices 410 include but are not limited to: attenuation device having 15 cc of air in a container that is capable of holding 30 cc of volume; Foley catheter or other catheter having an inflatable anchoring balloon; drug delivery infuser; J stent; etc.

Figure 39A:
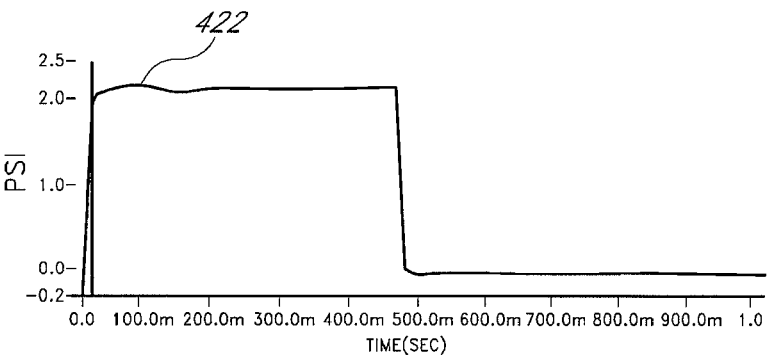
FIGS. 39A-D presents graphs of attenuation/pressure reduction vs. time for various attenuation device air volumes.
Figure 39B:
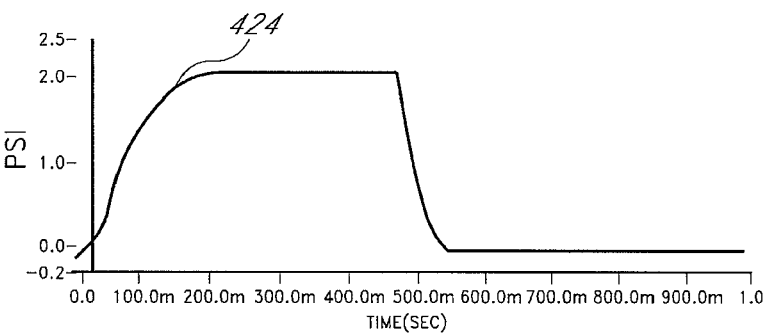
Figure 39C:
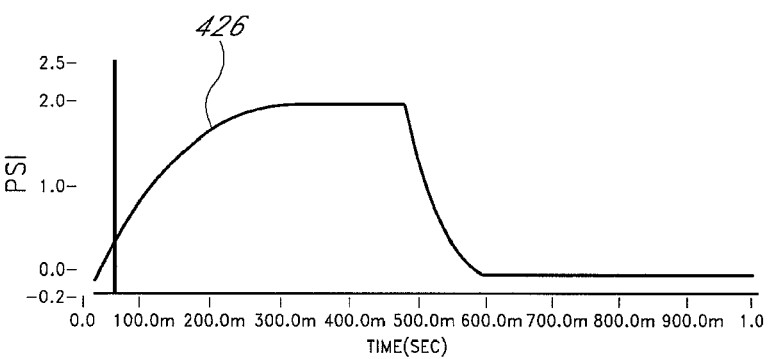
Figure 39D:
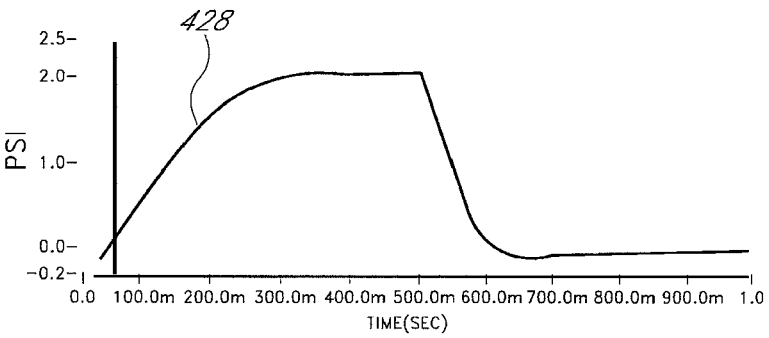

FIGS. 39A-D illustrates attenuation (i.e. pressure reduction) with various attenuation device air volumes. The data for these graphs were generated using a bench top bladder simulation program. Here, the maximum spike pressure is 2.0 psi. The spike event duration is approximately 40 mS, which is approximately equivalent to the duration of a coughing or sneezing event. With reference to FIG. 39A, a test was conducted with a 250 mL rigid plastic container filled with synthetic urine. A regulated pressure of 2.0 psi was introduced into the container via a controlled solenoid valve. A pressure transducer detected the pressure rise. Here, the pressure rise time (Tr) of the container pressure 422 to reach 2.0 psi was approximately 40 msec. With reference to FIG. 39B, a similar test was conducted on a 250 mL rigid plastic container. Here, an attenuation device filled with 15 mL of air was placed inside the container willed with synthetic urine. Here, the Tr of the container pressure 424 to reach 2.0 psi was approximately 195 msec. Thus the attenuation device slowed the rise time by 4.8×. During the spike event (i.e. when time equaled 40 msec), the pressure inside the container reached 0.7 psi (vs. 2 psi), resulting in a 65% reduction of pressure vs. baseline. With reference to FIG. 39C, a similar test was conducted; the only difference being that the attenuation device was filled with 25 mL of air. Here, the Tr of the container pressure 426 to reach 2.0 psi was approximately 290 msec. Thus the attenuation device slowed the rise time by 7.25×. During the spike event (i.e. when time equaled 40 msec), the pressure inside the container reached 0.5 psi (vs. 2 psi), resulting in a 75% reduction of pressure vs. baseline. With reference to FIG. 39D, a similar test was conducted; the only difference being that the attenuation device was filled with 30 mL of air. Here, the Tr of the container pressure 428 to reach 2.0 psi was approximately 340 msec. Thus the attenuation device slowed the rise time by 8.5×. During the spike event (i.e. when time equaled 40 msec), the pressure inside the container reached 0.4 psi (vs. 2 psi), resulting in a 80% reduction of pressure vs. baseline.

Figure 44A:
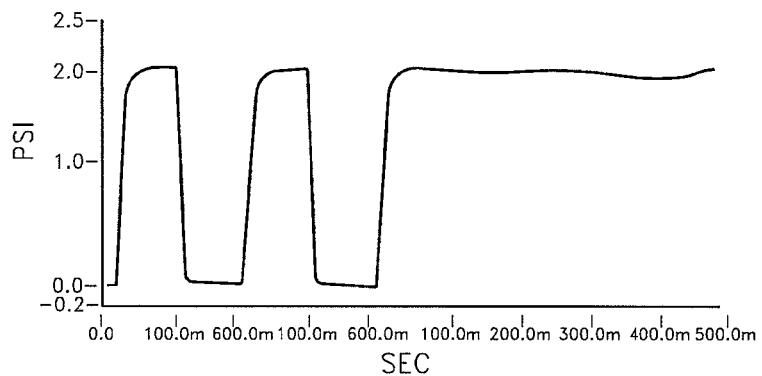
FIGS. 44A-D shows pressure vs. time curves generated by a bench top bladder simulator.
Figure 44B:
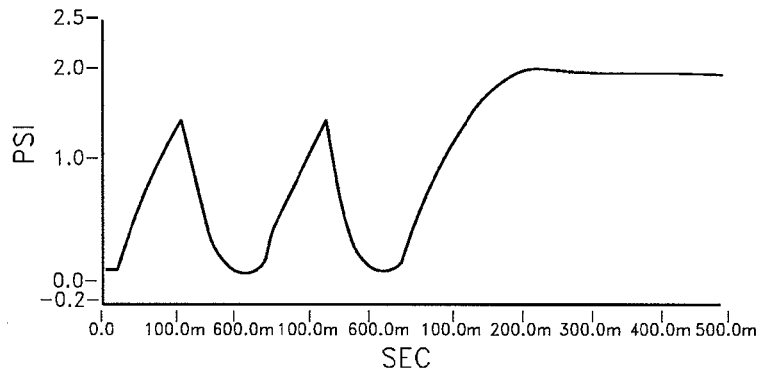
Figure 44C:
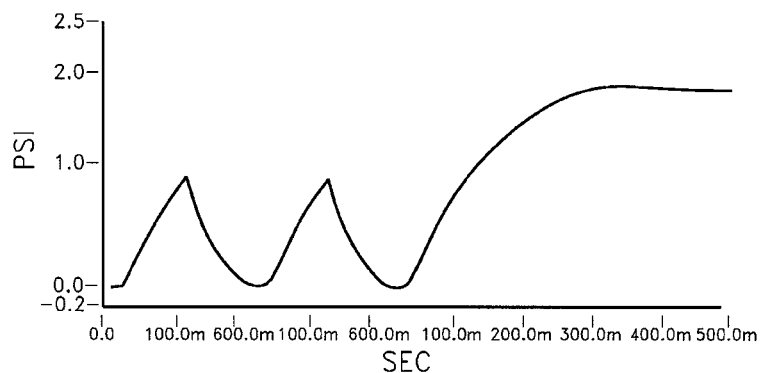
Figure 44D:
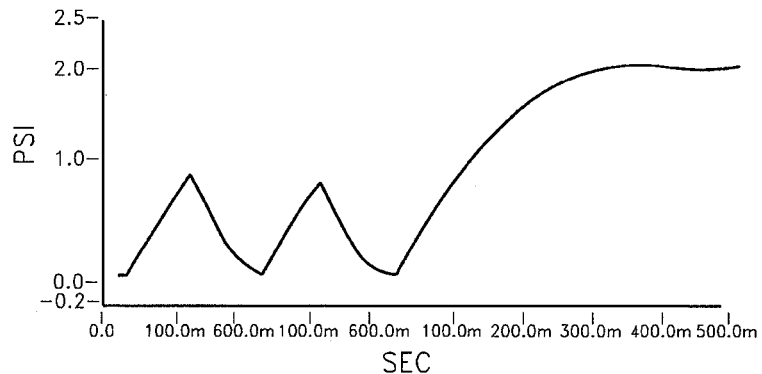

FIGS. 44A-D show pressure vs. time curves generated by a bench top bladder simulator. FIG. 44A shows the baseline pressure-time curve without an attenuation device. FIG. 44B shows the pressure-time curve with an attenuation device having a 15 cc air volume. FIG. 44C shows the pressure-time curve with an attenuation device having a 25 cc air volume. FIG. 44D shows the pressure-time curve with an attenuation device having a 30 cc air volume.

Algorithm(s) for Measuring Leak Point Pressures: Typical measurement of a patients leak point pressure is taken with pressure catheters in the bladder and in the rectum. The patient tightens the abdominal and pelvic muscles (valsalva) to increase the external pressure exerted on the bladder. At the time when the test administrator identifies visually that leakage has occurred, a button is pressed, and the most recent pressure data points are recorded. Typical urodynamic equipment in use today measures 2 to 35 data points per second. Given the time delay from when leakage occurs and when leakage is evident to the test administrator, and the fact that pressure decreases when leakage occurs, one embodiment of a more accurate method of measuring leak point pressure involves measuring pressure at the rate of 1000 pts per second, and programming or setting a computer to look at the prior 5/3/2/1 second(s) and to look for the peak-generated pressures when the clinician presses the "leak" button (i.e. a button on or in communication with the computer that the clinician pushes upon seeing or detecting leakage).

Figure 49:
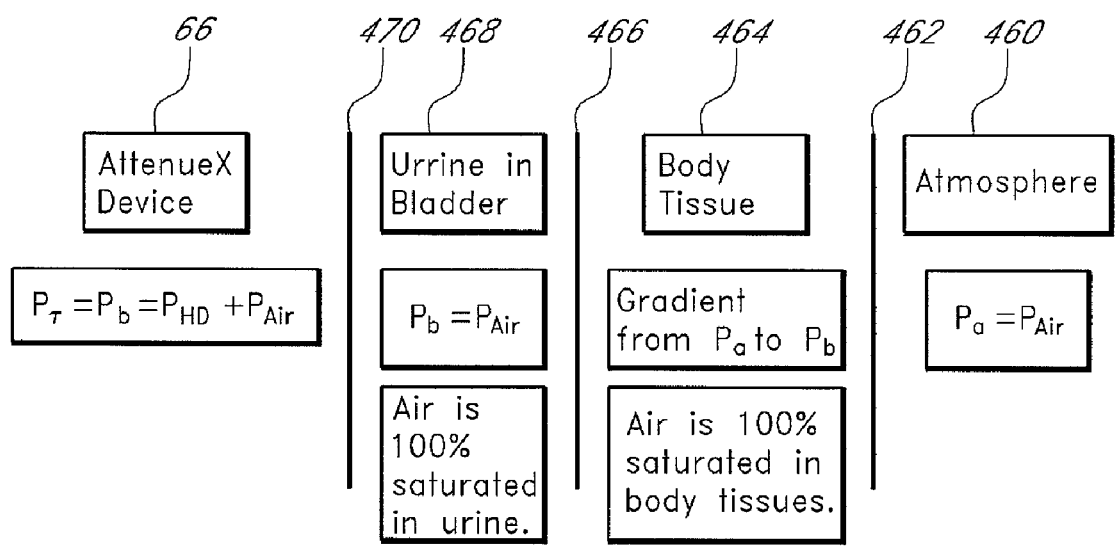
FIG. 49 is a schematic representation of an attenuation device with high vapor pressure media in accordance with one aspect of the present invention.

In accordance with another aspect of the present invention, there is provided a method of attenuating pressure changes in the bladder by introducing one or more low permeability gases and/or fluids with higher vapor pressures into an attenuation device. A lower permeability and higher vapor pressure gas or fluid usually has a higher density than air or water, respectively. The solubility of the gas or fluid in urine is commonly very low. With reference to FIG. 49, the illustrative embodiments described herein show an attenuation device 66 with one high vapor pressure gas or fluid. However, it will be understood that the attenuation device 66 can have one or more high vapor pressure media (i.e. gases and/or fluids, or combinations thereof). Outside the body, the atmospheric pressure ($P_a$) is equal to the partial pressure of air ($P_{Air}$). The pressure within the bladder ($P_b$) is approximately equal to $P_a$; however, in practice, $P_b$ is slightly higher $P_a$. For example, if $P_a$ is 14.7 psi or 1 atm, then $P_b$ can be approximately 14.85 psi (i.e. 14.7 psi+0.15 psi). There is a usually a pressure gradient from $P_b$ to $P_a$ within the tissues 464 of the body moving from the walls 466 of an individual's bladder 468 to the surrounding atmosphere 460 outside the skin 462. Since $P_b$ is greater than $P_a$, the pressure gradient results in the transfer of gases from the inside the body, such as, for example, from within the bladder outward through the pores in the skin 462 of an individual. The total pressure within the attenuation device ($P_T$) (i.e. within the outer wall 470 of the attenuation device 66) is equal to the sum of partial or vapor pressures of the high vapor pressure gas or fluid ($P_{HD}$) and $P_{Air}$.

With reference to FIG. 49, in one embodiment, the attenuation device 66 comprises an outer wall 470 and a high vapor pressure gas or fluid that generally has low permeability through the outer wall 470. In one embodiment, the wall 470 comprises a material, such as, for example, polyurethane, that is characterized by low permeability for the high vapor pressure media and moderate to high permeability for air. Examples of suitable high vapor pressure media include, but are not limited to: sulfur hexafluoride hexafluoroethane; perfluorocarbons ranging from perfluoropropane, perfluorobutane, perfluoropentane, perfluorohexane, perfluorohepane, perfluorooctane, perfluorodecalin, octafluoropropane, decafluoro-n-butane, perfluorooctylbromide to perfluoroperhydrophenanthrene; and inhaler propellants like heptafluoropropane and tetrafluoroethane.

With continued reference to FIG. 49, air is dissolved in the urine in the bladder. As explained above, $P_b$ is slightly greater than $P_{Air}$. Here, $P_T = P_b = P_{HD} + P_{Air}$. In one embodiment, if the material of the attenuation device 66 does not allow the higher vapor pressure gas to permeate through the device 66, air is driven into the attenuation device until the partial pressure of air in the urine matches the partial pressure of air in the attenuation device. In another embodiment, if a high vapor pressure fluid with a vapor pressure ($P_{HD}$) greater than the bladder pressure and a low permeability rate through the attenuation device wall were put into the attenuation device 66, air would be driven into the device 66 until the partial pressures of air are equal in the attenuation device 66 and in the urine. With a reservoir of fluid in the attenuation device 66 more vapor could be evaporated when $P_b$ decreases and vapor would condense when the $P_b$ increases, thereby resulting in a constant pressure system.

In one embodiment, where the average $P_b$ is known, a constant volume system is achieved by using a wall material that is generally taut and rigid in structure, such as, for example, silicone, polyurethane or any derivative thereof, that allows permeability to air but not to the selected high vapor pressure gas or fluid/vapor. Here, the attenuation device 66 is placed deflated into the bladder. A mixture of air and higher vapor pressure gas or fluid are injected into the attenuation device 66 so that the $P_{HD}$ matches the average pressure of the bladder ($P_b$) minus the atmospheric pressure ($P_a$). If there is no loss of the higher vapor pressure gas or fluid/vapor through the attenuation device wall, an equilibrium point is reached when the partial pressure of air in the attenuation device matches the partial pressure of air in urine. If the volume of gas in the attenuation device 66 puts no tension on the wall of the attenuation device, then the vapor or partial pressure of the higher vapor pressure gas or vapor equals the average bladder pressure minus the atmospheric pressure and the partial pressure of air in the attenuation device equals the partial pressure of air in the urine.

It will be noted that the pressure in the bladder typically ranges from 0 to 2 psi and is a function of the lifestyle of the individual. In one embodiment, comprising a constant pressure system, the wall of the attenuation device 66 can be designed to provide tension to control volume changes due to pressure variations in the bladder. For example, in one embodiment, if the attenuation device 66 were designed to match an average bladder pressure of 0.15 psi but the individual's bladder pressure is higher, air would be forced out of the attenuation device 66 until the partial pressure of air balances between the attenuation device and the urine or all of the air is forced out of the attenuation device. If the bladder pressure were lower, air would be driven into the attenuation device until the tension on the walls of the attenuation device results in the internal partial pressure of air equaling the bladder partial pressure of air.

Figure 50A:
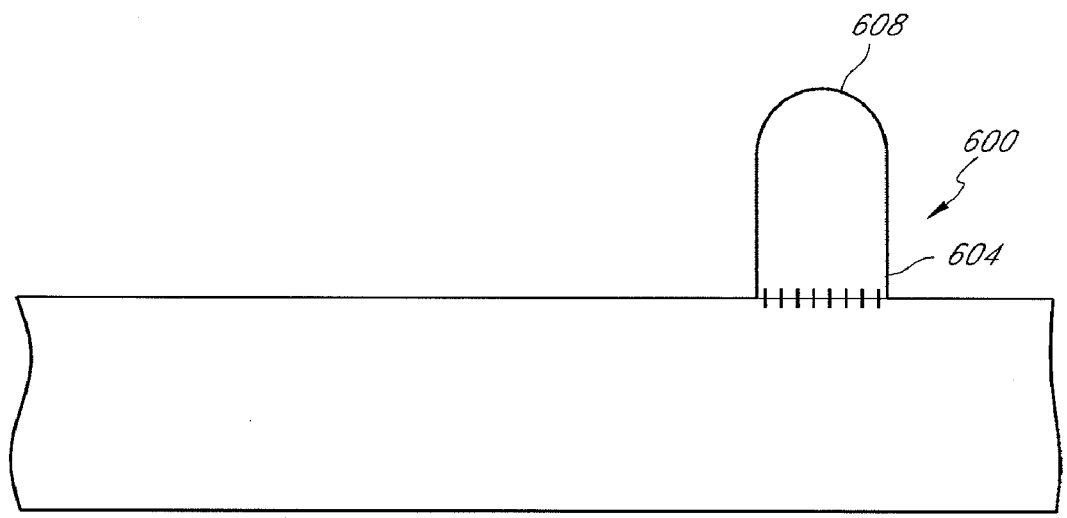
FIG. 50A is a schematic cross-sectional view through a vessel, illustrating an attenuation device in fluid communication with the vessel, the attenuation device being in a collapsed state.
Figure 50B:
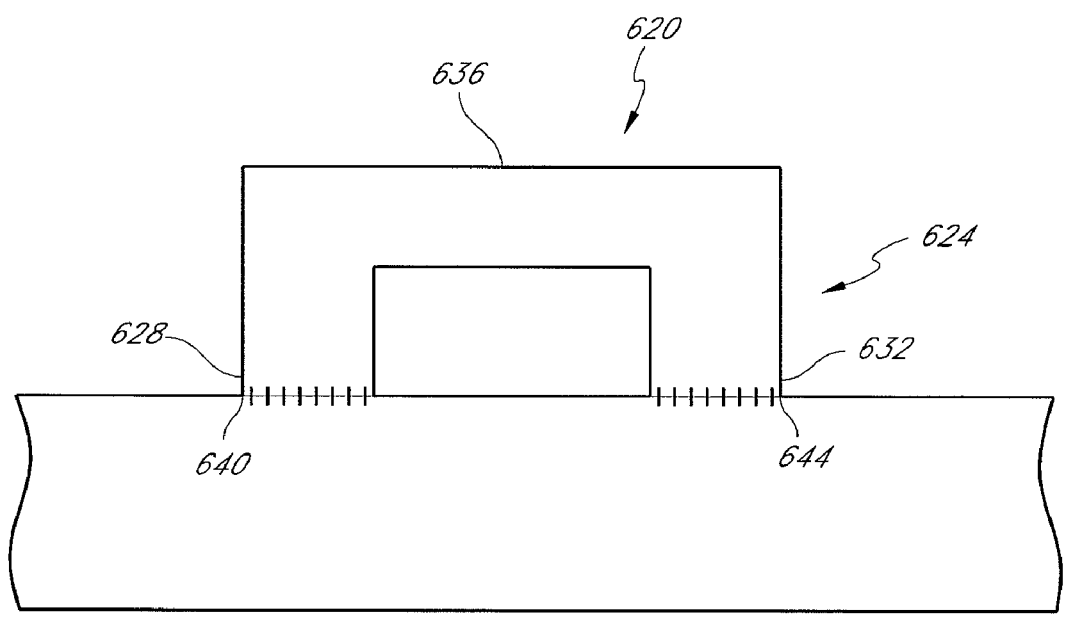
FIG. 50B is a schematic cross-sectional view through a vessel, illustrating an attenuation device in proximity to a vessel with more than one point of pressure communication with the vessel.
Figure 50C:
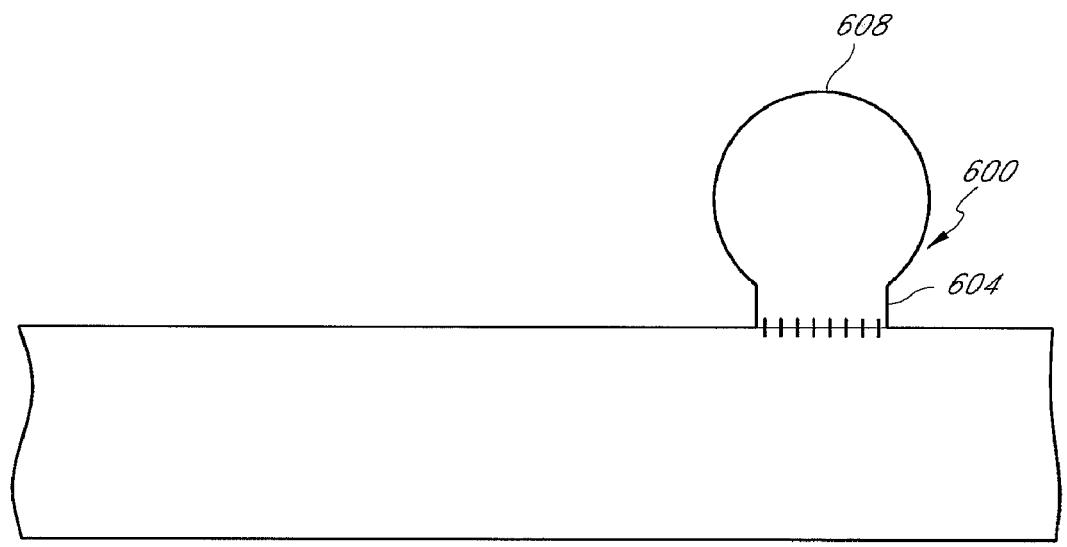
FIG. 50C is a schematic cross-sectional view through a vessel, illustrating the attenuation device of FIG. 50A in proximity to the vessel in an expanded state.

FIGS. 50A and 50C illustrate a pressure regulator or attenuation device 600 that includes a connection zone 604 for connecting to a body conduit and an attenuation zone 608. The connection zone 604 is configured to be placed in pressure communication with or proximity to the cardiovascular system. For example, the connection zone 604 can be sutured or otherwise affixed to the cardiovascular system. The attenuation zone can comprise a compliant material or a variable volume structure configured to have compliant properties. The pressure regulator 600 can be coupled with the vessel A with or without creating an opening or portal in the vessel.

FIG. 50A depicts the pressure regulator 600 in fluid communication with a vessel through connection zone 604 and corresponding opening the vessel wall during a relatively low pressure phase, such as diastole. FIG. 50C depicts the pressure regulator 600 during a relatively high pressure phase, e.g., during systole or a random high pressure event.

Figure 50D:
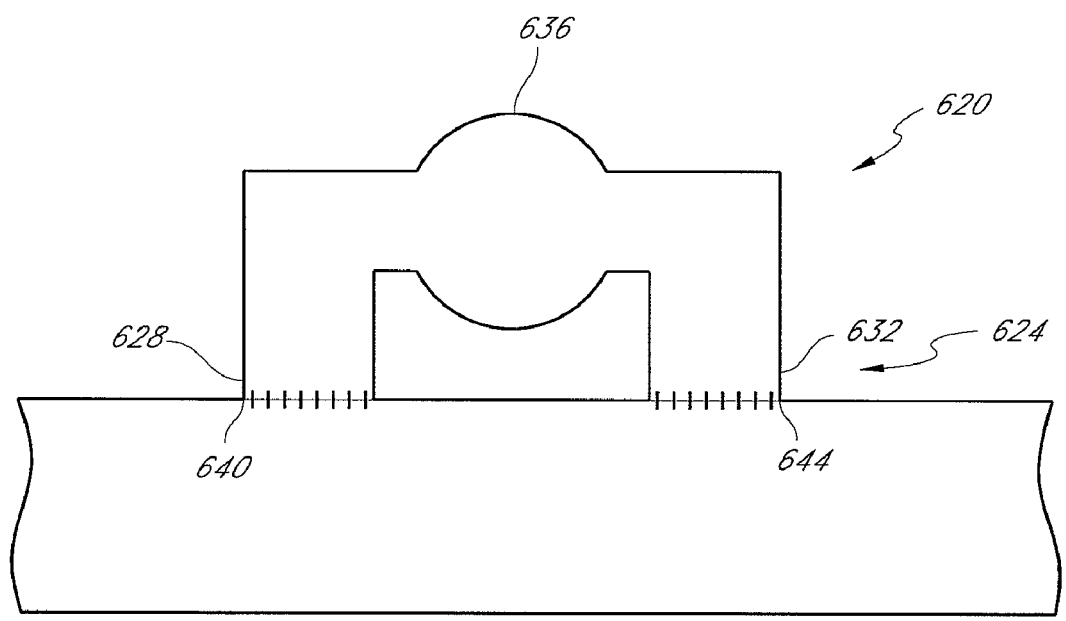
FIG. 50D is a schematic cross-sectional view through a vessel, illustrating the attenuation device of FIG. 50B in proximity to the vessel, the device being in an expanded state.

FIGS. 50B and 50D illustrate another pressure regulator 620 that can be implanted within a patient. The pressure regulator 620 includes a connection zone 624 that can include connection portions at first and second ends 628, 632. An attenuation zone 636 can be disposed between the first and second ends 628, 632. The attenuation zone 636 can be formed of a compliant material, such as is discussed above. The connection zone 624 can be affixed to the cardiovascular system at first and second locations 640, 644. The pressure regulator 620 can be affixed with or without creating one or more portals or openings into the vessel A.

FIG. 50B depicts the pressure regulator attenuation 620 during a relatively low pressure phase, such as diastole. FIG. 50D depicts the pressure regulator attenuation 620 during a relatively high pressure phase, e.g., during systole or a random high pressure event.

In the embodiment illustrated in FIG. 50C, connection zone 604 is illustrated as attached via a side anastomosis to the parent vessel and leading directly to the expandable reservoir or attenuation zone 608. However, the attenuation zone 608 may be positioned remotely from the connection to the parent vessel. For example, the attenuation zone might be at least about 2 cm, in some embodiments at least about 10 cm, and, if desired, at least about 20 cm from the parent vessel access point, depending upon the access point and desired location of the attenuator. For example, the access point may be located on the aorta, subclavian artery, brachial artery, carotid artery, or other point in the vasculature. The vascular access point may be in fluid communication with the attenuator by an elongate flexible tubular body which extends subcutaneously to a remote attenuator, which may be positioned in the vicinity of the clavicle, in the abdomen, or elsewhere as may be desired. The elongate flexible tubular body may be a pressure line connecting the vascular access point to the attenuator. The pressure line may be filled with any of a variety of media such as a non-compressible liquid (e.g. saline) or a compressible gas such as carbon dioxide or air.

Similarly, the embodiment of FIG. 50D may be connected into the vasculature at a first point and a second point which are remote from the location of the attenuator. The first and second attachment points may be connected to the same parent vessel, as illustrated in FIG. 50D. Alternatively, the pressure regulator 620 may be connected such that it functions as a shunt between a first vessel and a second vessel. The first and second vessels might be two positions on the same artery, to different arteries, or an artery and a vein. A venous to venous shunt may also be accomplished with the in-line attenuators of the present invention, although purely venous side pressure attenuation may be less common than on the arterial side of the cardiovascular system. Pressure attenuating arterial vascular shunts may be utilized in any of a variety of locations within the body, such as in the intracranial vasculature, the coronary vasculature, and the peripheral vasculature as will be apparent to those of skill in the art in view of the disclosure herein.

Figure 51A:
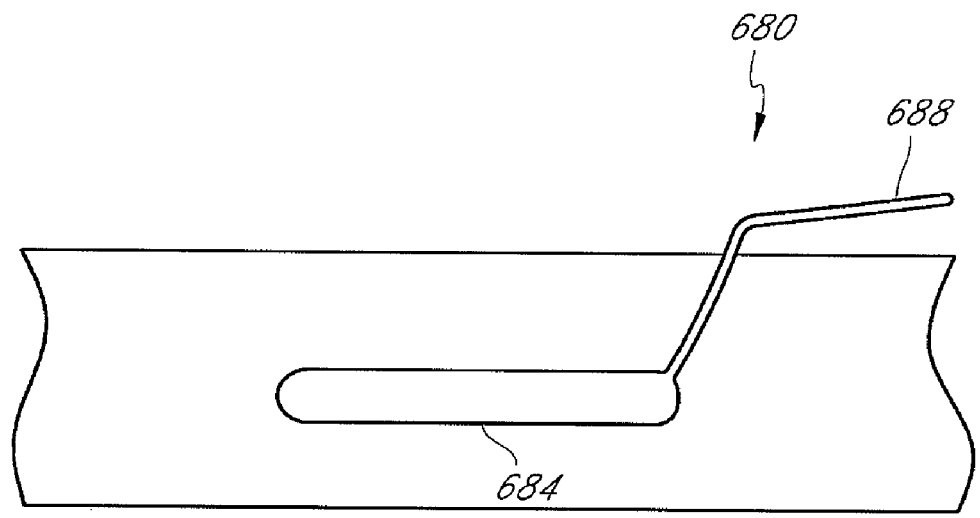
FIG. 51A is a schematic cross-sectional view through a vessel, illustrating an attenuation device that is partially within and partially outside of the vessel, with a portion of the device within the vessel expanded.
Figure 51B:
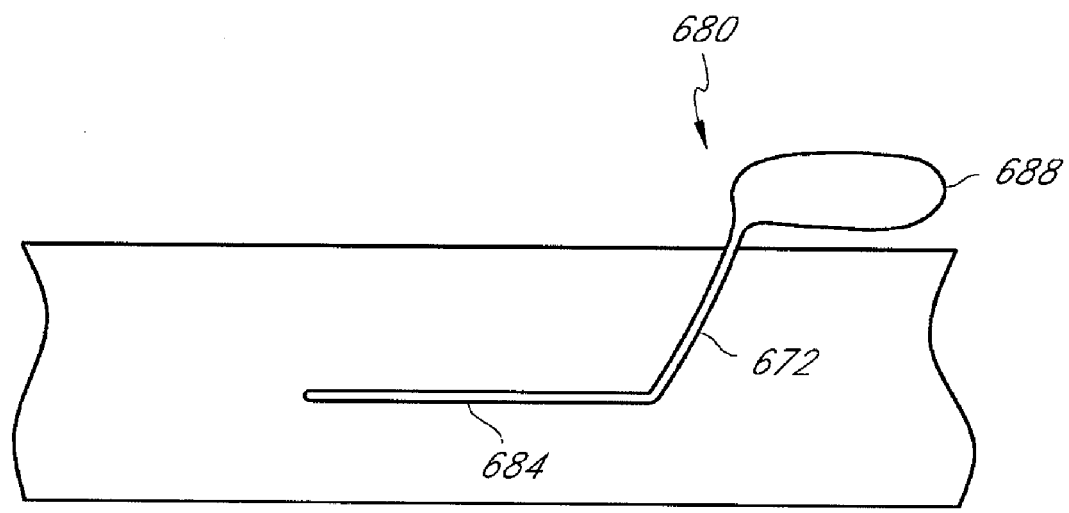
FIG. 51B is a schematic cross-sectional view through a vessel, illustrating the attenuation device of FIG. 51A partially within and partially outside of the vessel, with a portion of the device within the vessel in a compressed configuration attenuating a pressure spike.

FIGS. 51A-51B show another embodiment of a pressure regulator 680. The pressure regulator 680 includes an attenuation zone or device 684 that is placed partially within a body cavity or blood vessel and partially outside the body cavity or vessel. The regulator 680 can be applied partially within the body any partially outside the body. A partially implanted device could be used temporarily or permanently. In a temporary application it may be beneficial to mount the attenuator on an elongated means such as a catheter. A temporary system may be of benefit in a clinical scenario such as hypertensive crisis when the systolic blood pressure should be lowered quickly.

FIGS. 51A-51B show the pressure regulator partially in the cardiovascular system and partially outside the cardiovascular system. FIG. 51A shows that the pressure regulator 680 includes a first portion 684 that can be enlarged and a second portion 688 that also can be enlarged. The first portion 684 can include a cavity in which a fluid can reside. The second portion 688 also can include a cavity in which a fluid can reside. In one embodiment, a fluid flow path 672 is provided to convey a fluid between cavities in the first and second portion 684, 688. The pressure regulator 680 preferably is configured such that at least some of the fluid is urged into a first cavity in the first portion 684 when a relatively low pressure exists in the cavity or vessel in which the pressure regulator 680 is disposed. Such a condition is illustrated in FIG. 51A and could correspond to diastole. The pressure regulator 680 preferably also is configured such that at least some of the fluid is urged into a second cavity in the second portion 688 when a relatively high pressure exists in the cavity or vessel in which the pressure regulator 680 is disposed. Such a condition is illustrated in FIG. 51B and could correspond to systole.

One technique for generally urging the fluid into a cavity associated with the first portion 684 is to control the wall thickness of the first and second portions 684, 688. In particular, by providing a relatively thin wall in the first portion 684, the first portion may expand under pressure of the fluid in the pressure regulator 680. This would tend to urge fluid into the first portion 684 absent a change in external conditions. In another arrangement, the first portion 684 can include a more compliant material than the second portion 688, which will tend to urge fluid into the first portion when the regulator 680 is at rest.

Preferably, a housing will be provided for surrounding the second portion 688, to prevent compression of the second portion 688 as resulted of outside forces. As with previous embodiments, the fluid flow path 672 may be as long as desired, to enable positioning the second portion 688 at a location in or adjacent the body independent of the vascular access point utilized for positioning the first portion 684 within the vasculature.

Having thus described certain embodiments of the present invention, various alterations, modifications and improvements will be apparent to those of ordinary skill in the art. Such alterations, variations and improvements are intended to be within the spirit and scope of the present invention. Accordingly, the foregoing description is by way of example and is not intended to be limiting. In addition, we have described a variety of pressure attenuators including but not limited to gas filled and mechanical. However, other attenuating pressure attenuating devices may be used, such as a device filled with a medium that phase changes at a particular pressure. In addition, any dimensions that appear in the foregoing description and/or the figures are intended to be exemplary and should not be construed to be limiting on the scope of the present invention described herein.

What is claimed is:

1. An implantable blood pressure regulator, comprising:
   at least one connection zone for connection to a body conduit; and
   an attenuation zone being movable from a first state to a second state in response to a physiological pressure spike within said body conduit;
   wherein the movement from the first state to the second state lowers a level of pressure in the body conduit.

2. The implantable blood pressure regulator of claim 1, wherein the attenuation zone occupies a greater volume in the body conduit when in the first state than the second state.

3. The implantable blood pressure regulator of claim 1, wherein the attenuation zone comprises an expandable material and wherein a cross-sectional area of the attenuation zone is greater in the second state than in the first state.

4. The implantable blood pressure regulator of claim 1, further comprising a first attachment zone configured to be coupled with an upstream vascular segment and a second attachment zone configured to be coupled with a downstream vascular segment.

5. A method of treating a patient, comprising:
providing a variable volume structure;
placing the variable volume structure in pressure communication with the patients' vasculature such that the volume of the structure is reduced from a first volume to a second volume in response to a pressure spike in the vessel to reduce the magnitude of the pressure spike.

6. A method of treating a patient, comprising:
providing a conduit having first and second ends and an attenuation zone disposed therebetween;
configuring the attenuation zone to expand from a first volume to a second volume in response to a pressure spike in the vessel; and
coupling at least one of the first and second ends of the conduit with the patient's vasculature.

7. The method of claim 6, wherein the first end and second ends are coupled with upstream and downstream portions of the patient's vasculature.

8. The method of claim 6 further comprising contacting an interior wall of the vessel with the first and second ends of the conduit.

9. The method of claim 8, wherein at least one of the first and second ends is expanded into contact with the interior wall of the vessel.

10. The method of claim 6, wherein the attenuation zone has a first enlarged volume state corresponding to diastolic pressure and a second reduced volume state corresponding to systolic pressure.

11. The method of claim 6, wherein said attenuation zone comprises a bellow having a first and second activation level.

12. The method of claim 6, wherein said attenuation zone is configured to expand in response to an activation pressure to provide a cross-sectional area at least 10 percent larger than when not expanded.

13. The method of claim 6, wherein said attenuation zone is configured to expand from a first resting volume to a second, expanded volume for carrying blood across a span of the attenuation zone.

14. The implantable blood pressure regulator of claim 1, wherein the connection zone is a tube configured to be in fluid communication with a vessel through an opening in a wall of the vessel.

15. The implantable blood pressure regulator of claim 1, wherein the attenuation zone is coupled to said connection zone with a pressure line and wherein said pressure line is filled with non-compressible liquid, saline, compressible gas, air, or carbon dioxide.

16. The implantable blood pressure regulator of claim 1, wherein the attenuation zone comprises a first portion and second portion connected by a fluid flow path wherein said first portion is comprised of a material more compliant than said second portion.

17. The implantable blood pressure regulator of claim 1, wherein the connection zone is expandable and operable to engage an interior wall of a vessel or organ.

18. The implantable blood pressure regulator of claim 1, further comprising an engagement feature for coupling said connection zone to a portion of a cardio vascular system.

19. The implantable blood pressure regulator of claim 1, wherein said attenuation zone has a first enlarged volume state corresponding to diastolic pressure and a second reduced volume state corresponding to systolic pressure.

20. The implantable blood pressure regulator of claim 1, wherein at least a portion of said regulator encircles a body conduit.

21. The implantable blood pressure regulator of claim 1, wherein said attenuation zone comprises a bellow having a first and second activation level.

22. The implantable blood pressure regulator of claim 1, wherein said attenuation zone is configured to expand in response to an activation pressure to provide a cross-sectional area at least 10 percent larger than available at a resting pressure.

23. The implantable blood pressure regulator of claim 1, wherein said attenuation zone is configured to expand from a first resting volume to a second, expanded volume for carrying blood across its length.

24. An implantable blood pressure regulator comprising:
at least one connection zone for connection to a body conduit; and
an attenuation zone being movable from a first state to a second state in response to a physiological pressure spike wherein the movement from the first state to the second state restricts the extent of the pressure increase due to said pressure spike.

* * * * *